US011737785B2

(12) United States Patent
Cortes Cubero et al.

(10) Patent No.: US 11,737,785 B2
(45) Date of Patent: Aug. 29, 2023

(54) HIP OR SHOULDER PROSTHESIS AND PLACEMENT INSTRUMENTS

(71) Applicant: Desarrollos Biomecanicos Innovasan S.L., Valencia (ES)

(72) Inventors: Javier Cortes Cubero, Valencia (ES); Carlos M. Atienza Vicente, Valencia (ES); Andres Penuelas Herraiz, Valencia (ES); Fernando Garcia Torres, Valencia (ES)

(73) Assignee: Desarrollos Biomecanicos Innovasan S.L., Valencia (ES)

( * ) Notice: Subject to any disclaimer, the term of this patent is extended or adjusted under 35 U.S.C. 154(b) by 658 days.

(21) Appl. No.: 16/883,086

(22) Filed: May 26, 2020

(65) Prior Publication Data
US 2020/0323575 A1    Oct. 15, 2020

Related U.S. Application Data

(63) Continuation of application No. 16/766,863, filed on May 26, 2020, which is a continuation-in-part of
(Continued)

(30) Foreign Application Priority Data

Jun. 11, 2018  (ES) ............................... 201830565A
Jun. 10, 2019  (ES) ................................. 2019238992
Dec. 10, 2019  (ES) .................................. 201931091

(51) Int. Cl.
*A61B 17/56*      (2006.01)
*A61B 17/74*      (2006.01)
(Continued)

(52) U.S. Cl.
CPC .............. *A61B 17/56* (2013.01); *A61B 17/74* (2013.01); *A61B 17/8872* (2013.01);
(Continued)

(58) Field of Classification Search
CPC ............ A61B 17/1668; A61B 17/1684; A61B 17/1721; A61B 17/175; A61B 17/1753;
(Continued)

(56) References Cited

U.S. PATENT DOCUMENTS 4,714,478 A * 12/1987 Fischer .............. A61B 17/1668
                                                         623/22.4
6,322,565 B1 * 11/2001 Garner ............... A61B 17/1668
                                                          606/101
(Continued)

*Primary Examiner* — Larry E Waggle, Jr.
(74) *Attorney, Agent, or Firm* — Thomas A. O'Rourke; BODNER & O'ROURKE, LLP

(57) ABSTRACT

A hip/shoulder prosthesis includes: a head component; a metaphyseal component; a diaphyseal nail, and a locking device. The head component includes: a front face and rear face; with a bore, and first and second shaped recesses in the rear face. The metaphyseal component includes: a central transverse aperture at an angle to the metaphyseal component's axis; a first end configured for threaded engagement within the bore of the head component; and a longitudinal hole that begins at the second end, transects the transverse aperture and reaches the first end, to receive the locking device. The diaphyseal nail is inserted in the femoral or humeral canal, and includes: fastening apertures that receive corresponding screws for fastening the diaphyseal nail to the femur or humerus; a portion configured to be received within, and engage, the transverse aperture of the metaphyseal component, and a transverse hole configured to receive the locking device.

2 Claims, 89 Drawing Sheets

Related U.S. Application Data application No. PCT/ES2019/070399, filed on Jun. 10, 2019.

(51) Int. Cl.

| | | |
|---|---|---|
| *A61B 17/88* | (2006.01) | |
| *A61F 2/46* | (2006.01) | |
| *A61F 2/36* | (2006.01) | |
| *A61F 2/40* | (2006.01) | |
| *A61B 90/00* | (2016.01) | |
| *A61B 17/72* | (2006.01) | |
| *A61B 17/00* | (2006.01) | |
| *A61B 17/84* | (2006.01) | |
| *A61B 17/90* | (2006.01) | |
| *A61B 17/16* | (2006.01) | |
| *A61B 17/17* | (2006.01) | |

(52) U.S. Cl.
CPC ............ *A61F 2/367* (2013.01); *A61F 2/3609* (2013.01); *A61F 2/3676* (2013.01); *A61F 2/4014* (2013.01); *A61F 2/4607* (2013.01); *A61F 2/4612* (2013.01); *A61B 17/1668* (2013.01); *A61B 17/1721* (2013.01); *A61B 17/1753* (2013.01); *A61B 17/72* (2013.01); *A61B 17/848* (2013.01); *A61B 17/90* (2021.08); *A61B 2017/0092* (2013.01); *A61B 2017/564* (2013.01); *A61B 2090/035* (2016.02); *A61F 2002/3654* (2013.01); *A61F 2002/4051* (2013.01); *A61F 2002/4062* (2013.01); *A61F 2002/4077* (2013.01); *A61F 2002/4619* (2013.01); *A61F 2002/4628* (2013.01); *A61F 2002/4629* (2013.01)

(58) Field of Classification Search
CPC ................ A61B 17/1778; A61B 17/56; A61B 2017/564; A61B 17/74; A61F 2/2609; A61F 2/367; A61F 2/4014; A61F 2002/4062; A61F 2/4607; A61F 2/4612
See application file for complete search history.

(56) References Cited

U.S. PATENT DOCUMENTS 10,456,145 B2 * 10/2019 Laviano ............ A61B 17/1617
10,499,932 B2 * 12/2019 Koogle, Jr. ........ A61B 17/1617

* cited by examiner

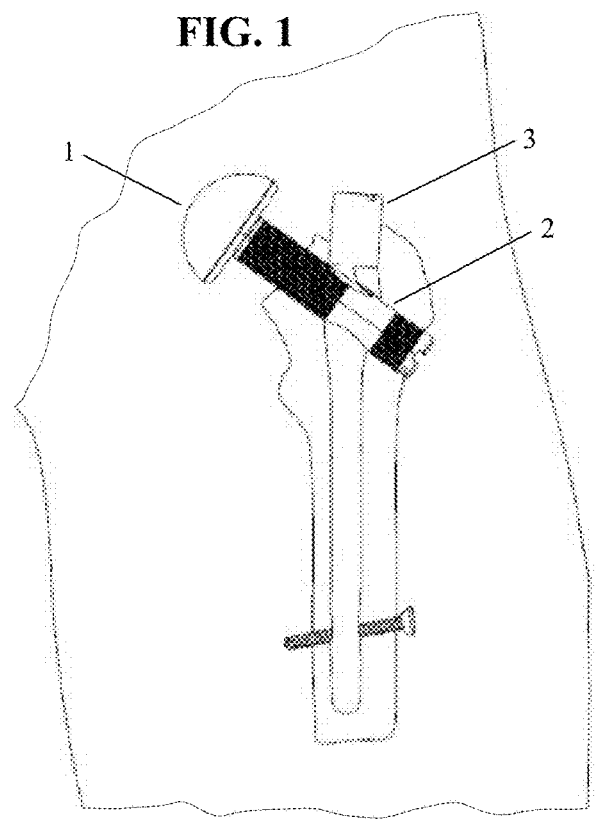
FIG. 1
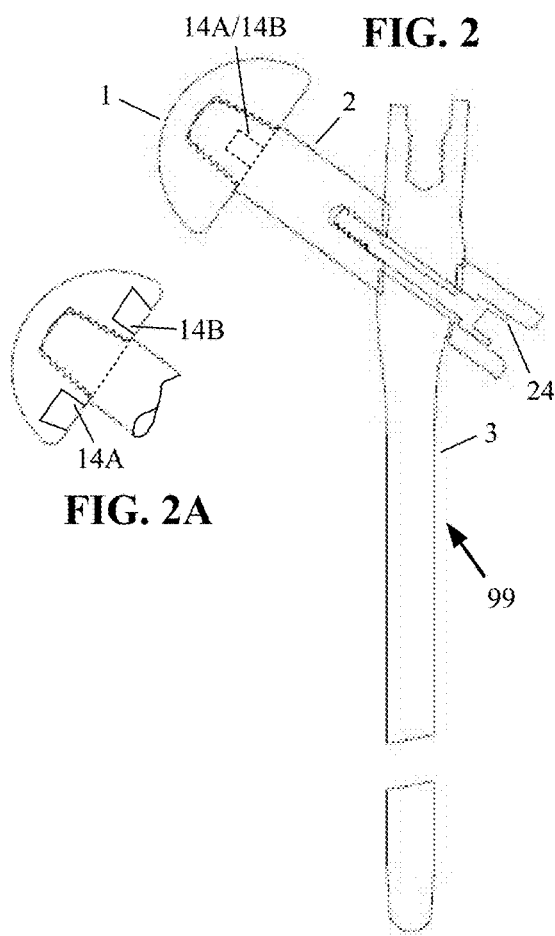
FIG. 2
FIG. 2A
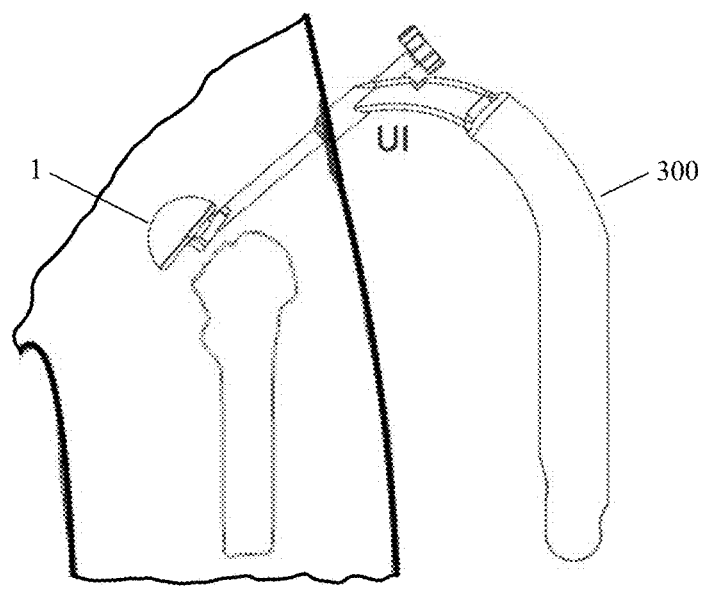
FIG. 3

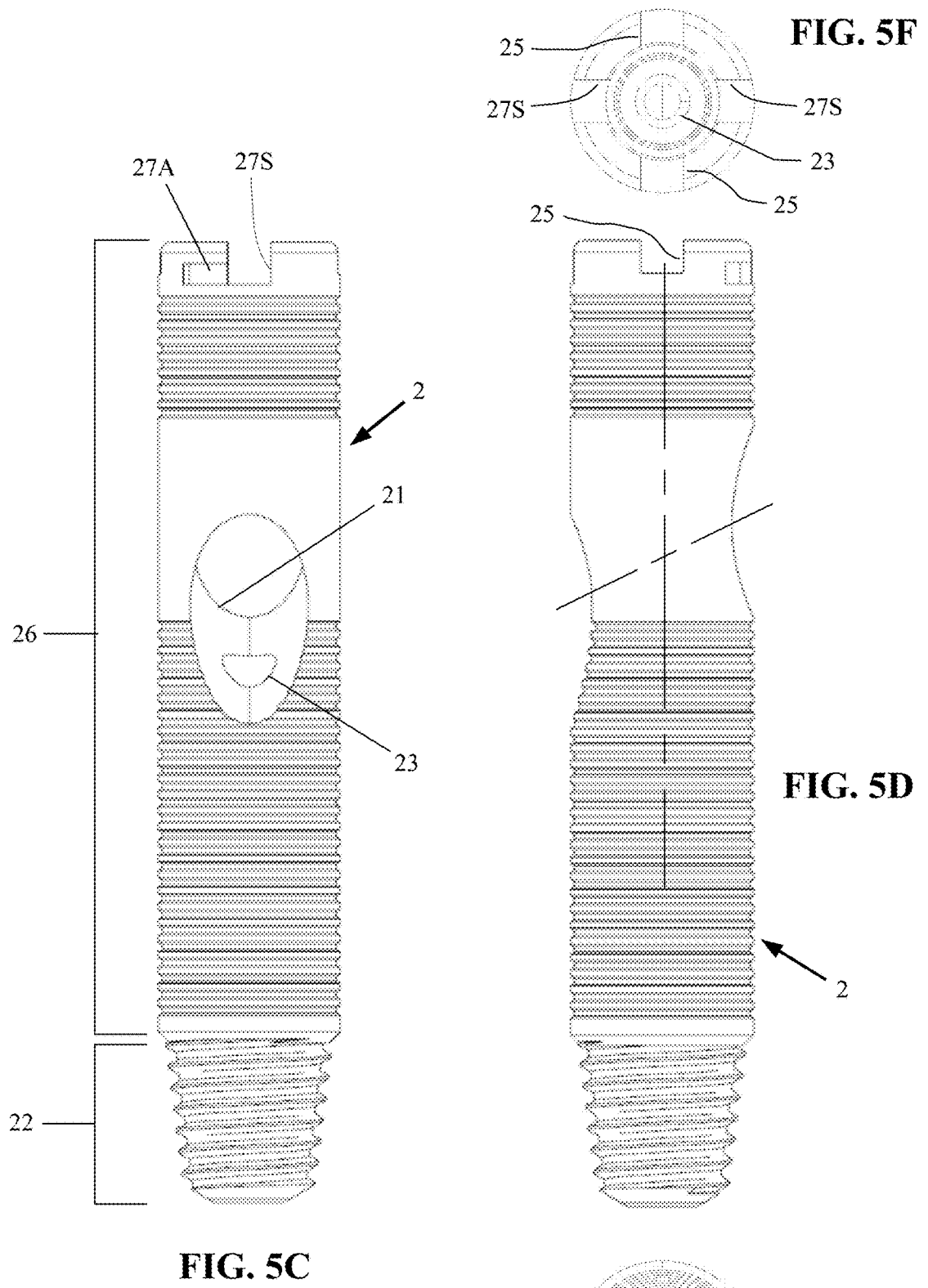

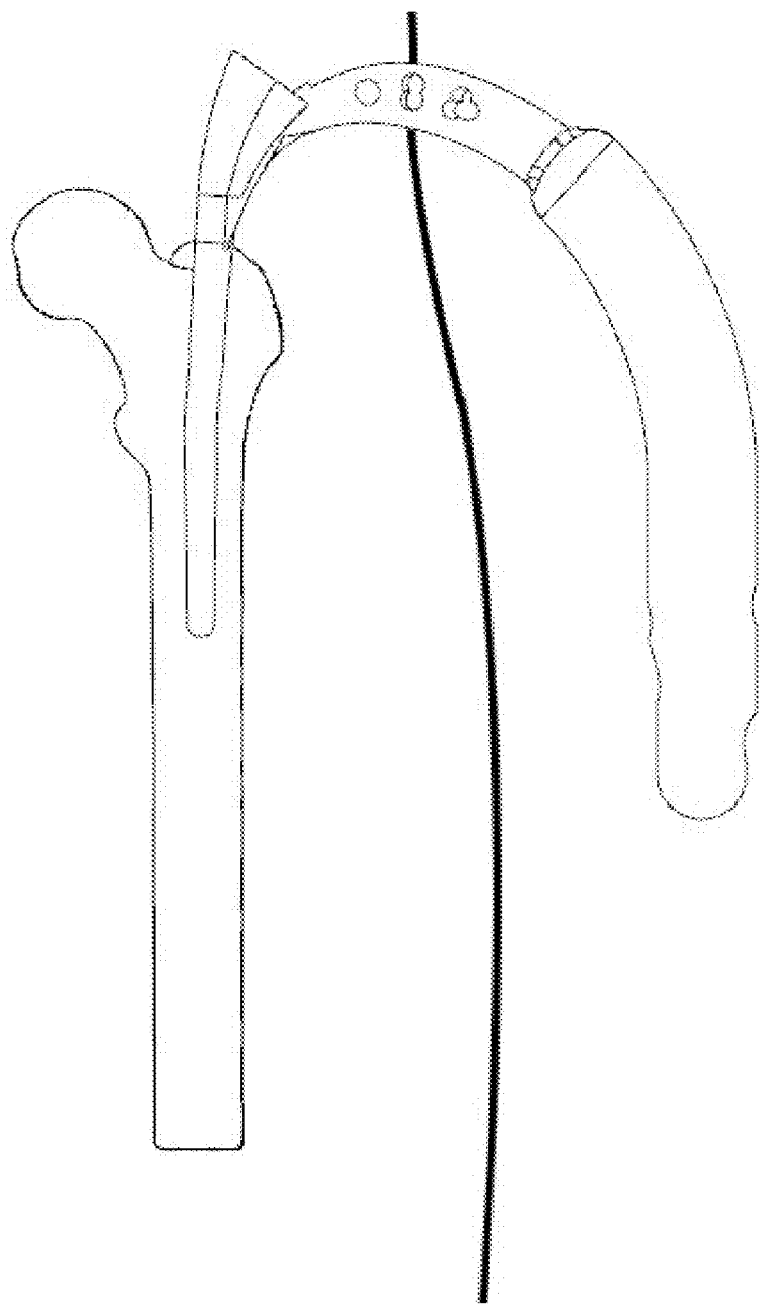
FIG. 12Aii

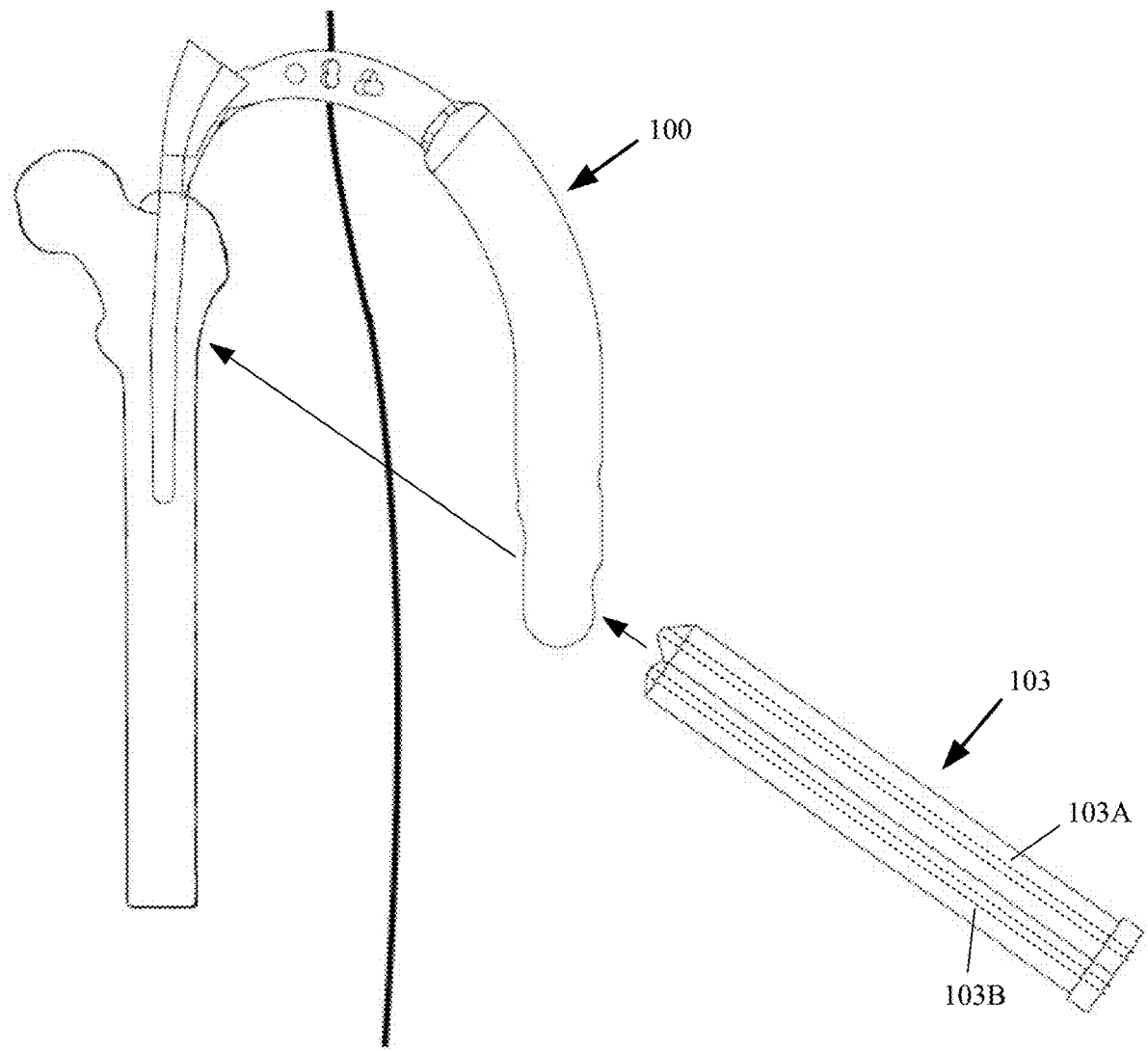
FIG. 12Aiii

FIG. 12Cii

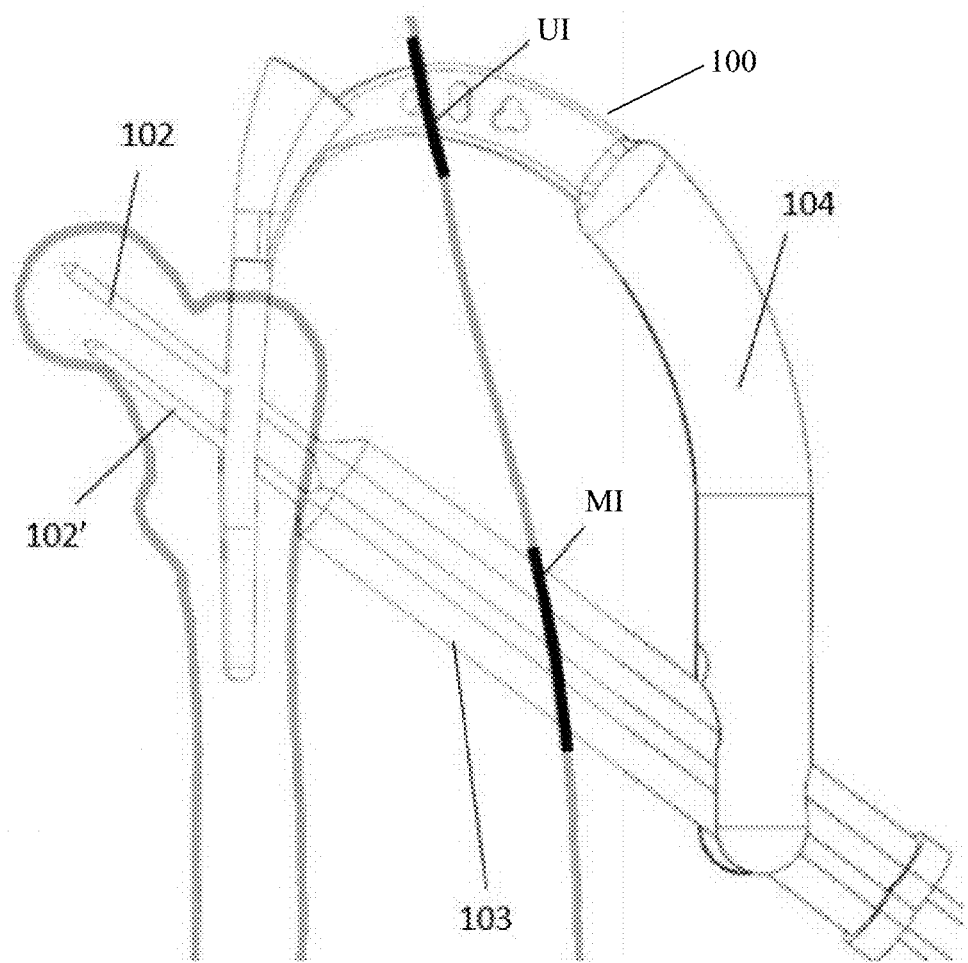
FIG. 12Ciii

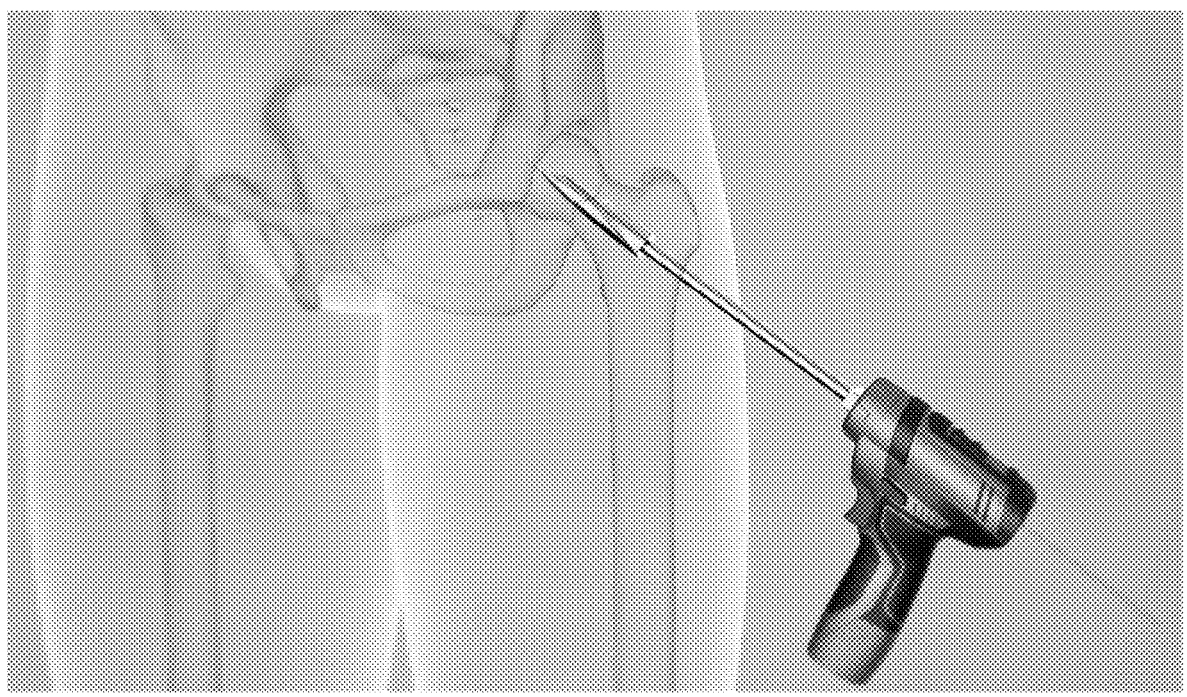
FIG. 12Eii

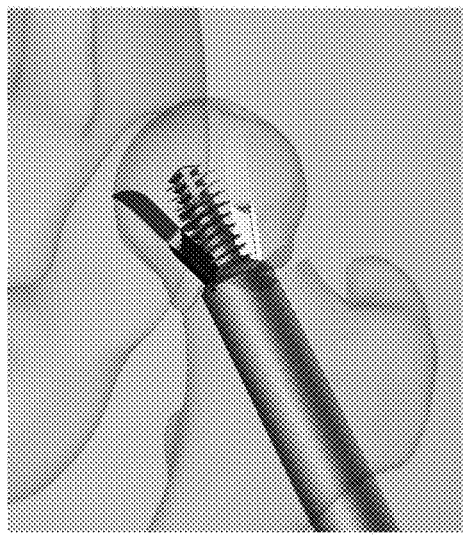
FIG. 12Hi
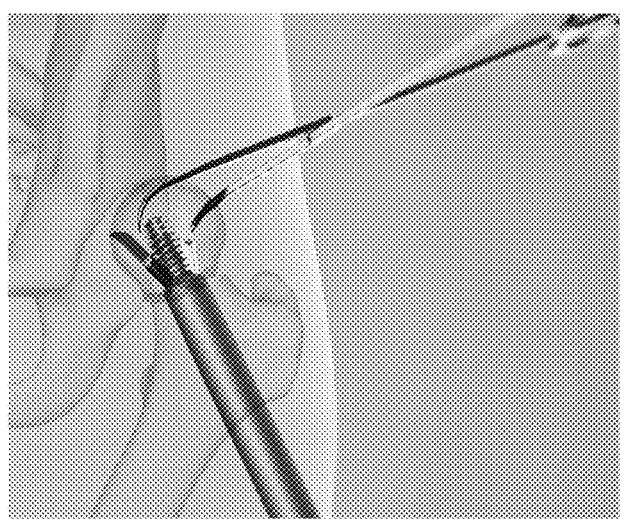
FIG. 12Hii
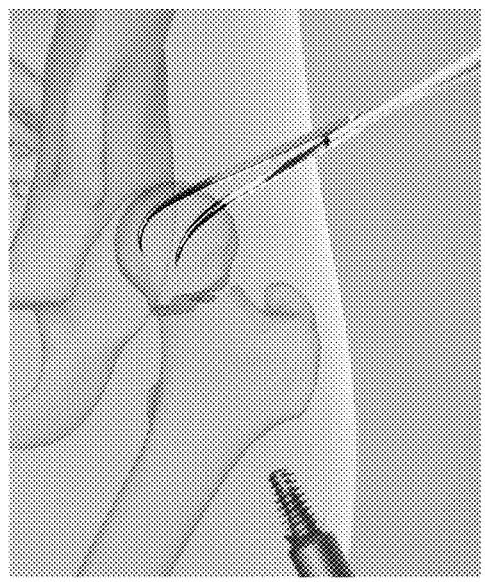
FIG. 12Hiii
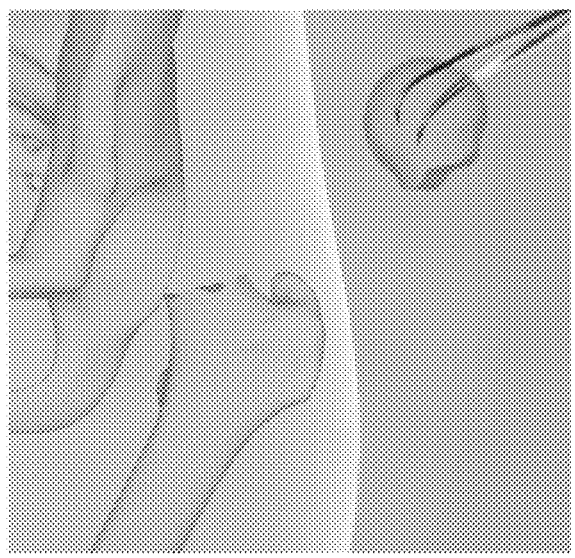
FIG. 12Hiv

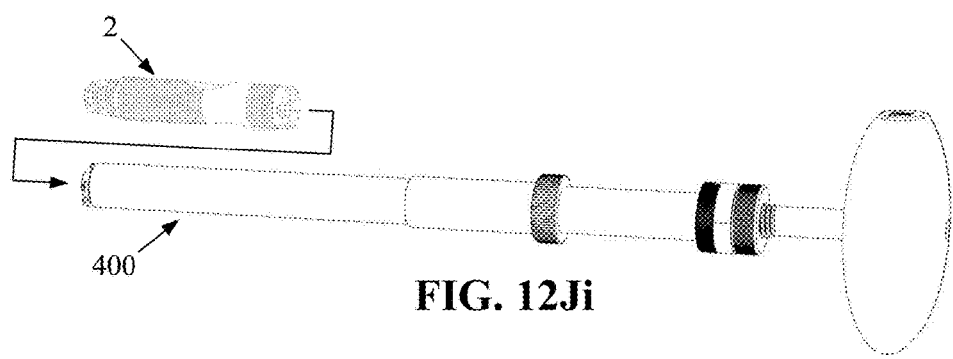
FIG. 12Ji
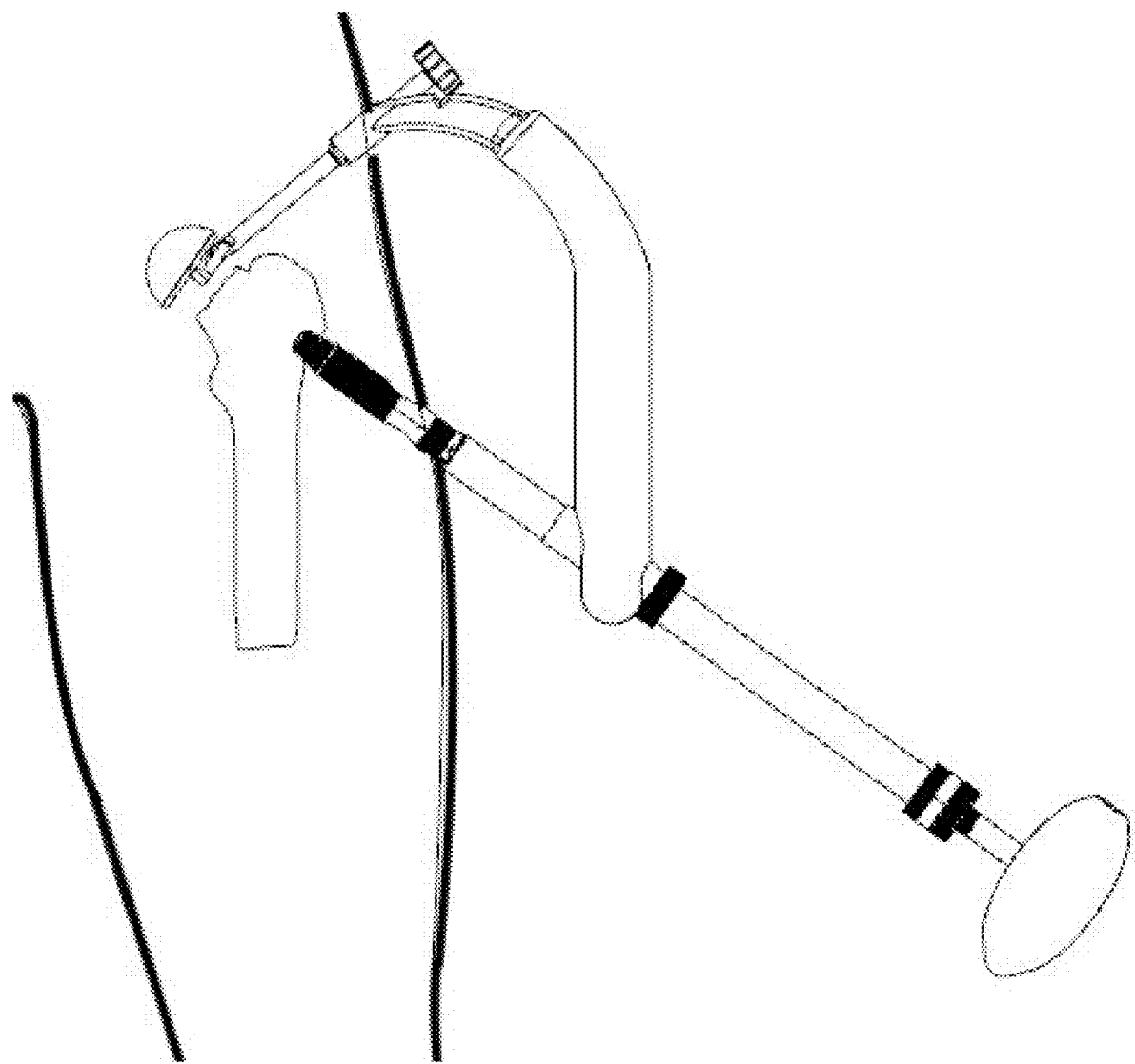
FIG. 12Jii

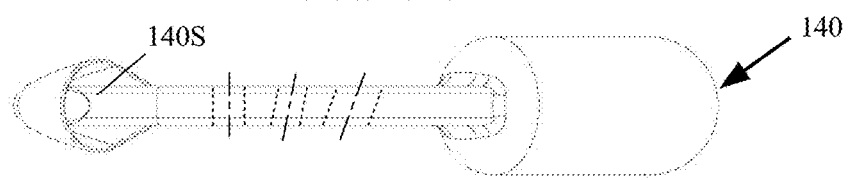
FIG. 13F
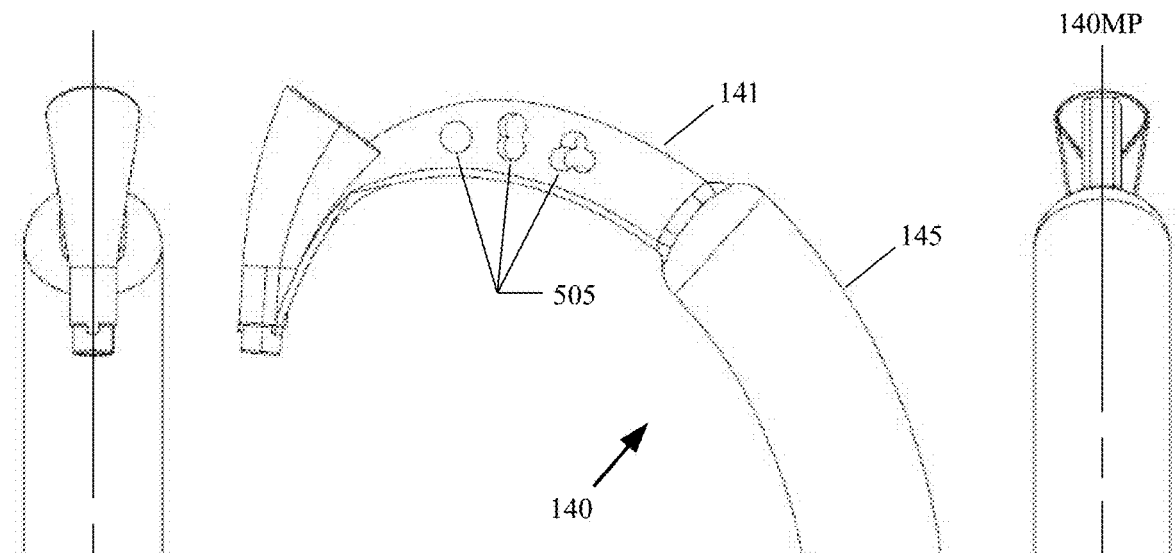
FIG. 13C
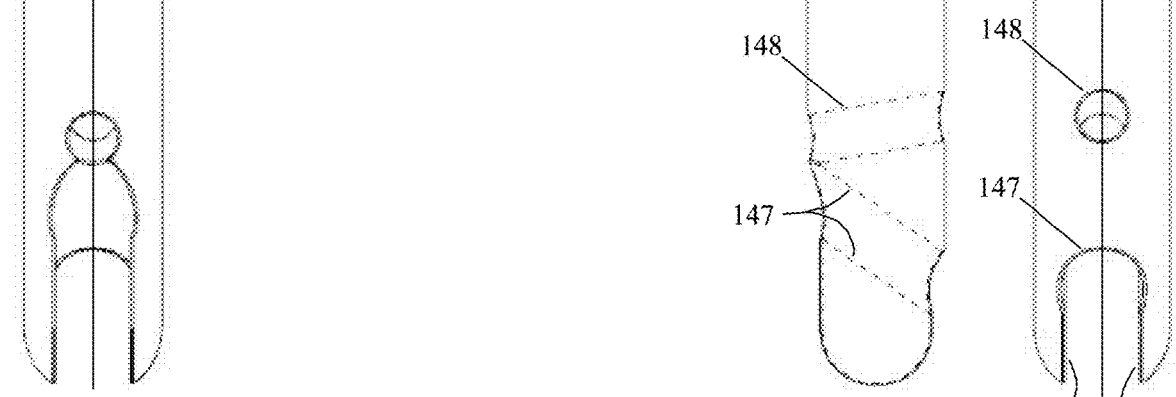
FIG. 13D
FIG. 13E
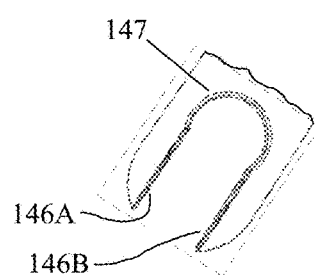
FIG. 13G

FIG. 13H
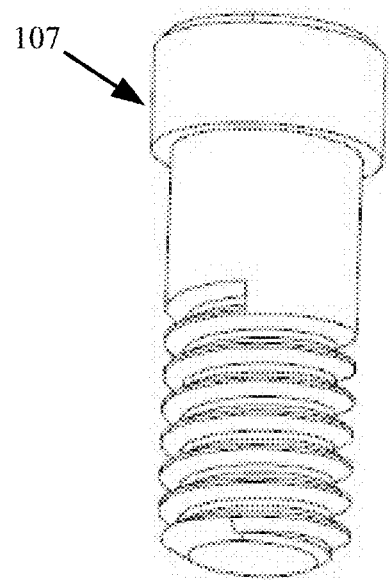
FIG. 13J
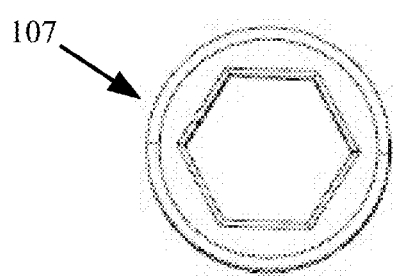
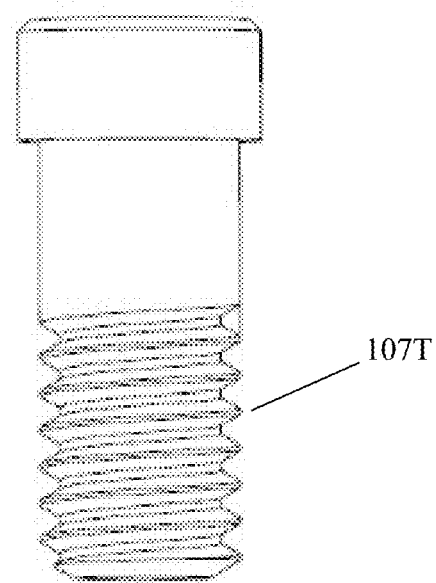
FIG. 13I

FIG. 16H
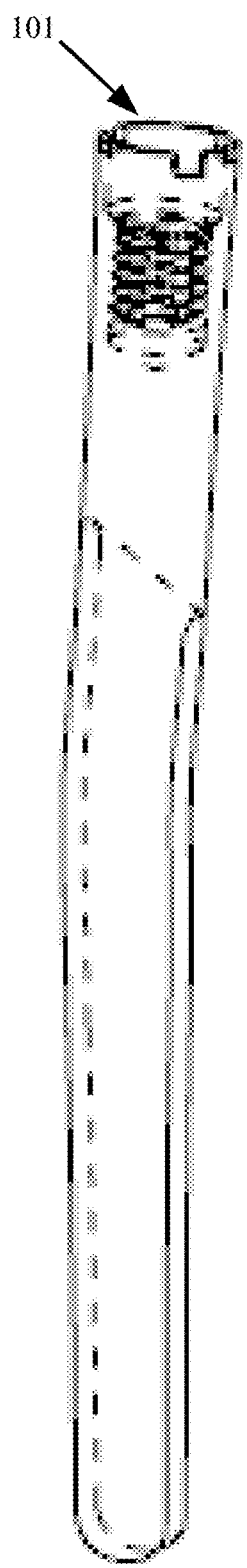
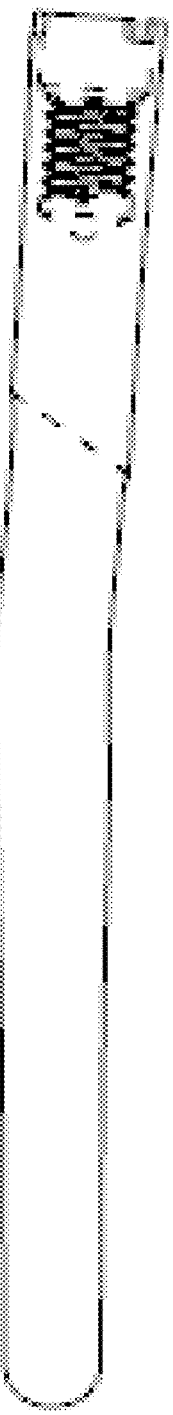
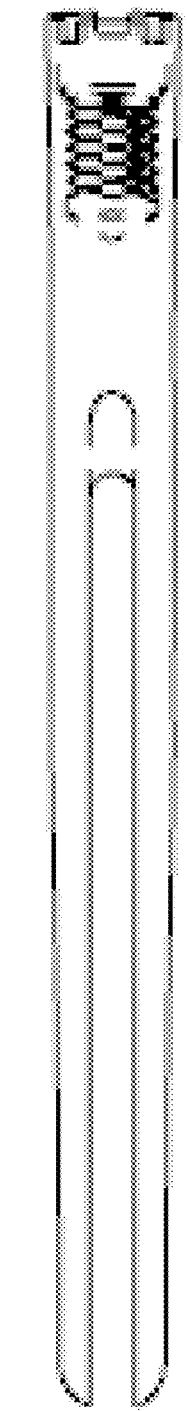
FIG. 16E
FIG. 16G    FIG. 16F

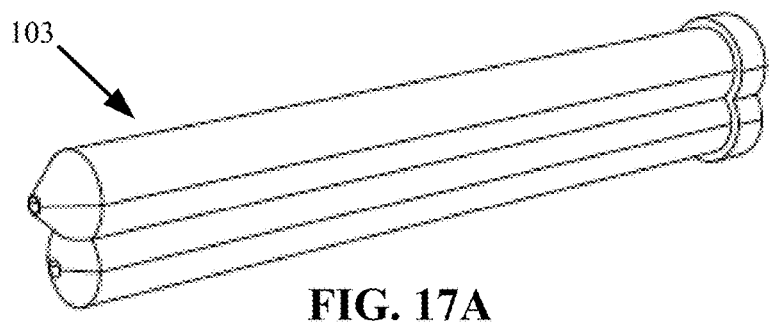
FIG. 17A
FIG. 17C
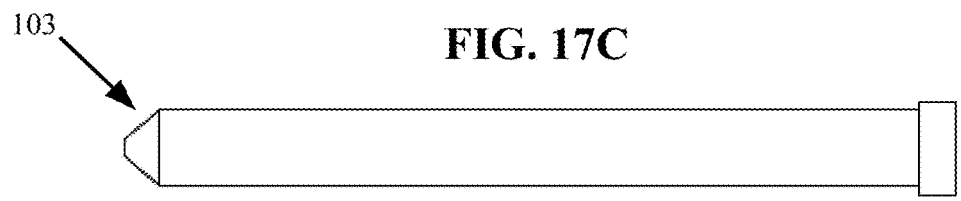
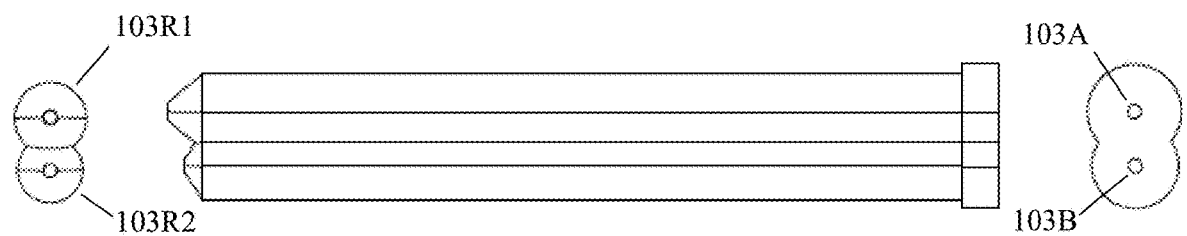
FIG. 17E
FIG. 17B
FIG. 17D

FIG. 18D
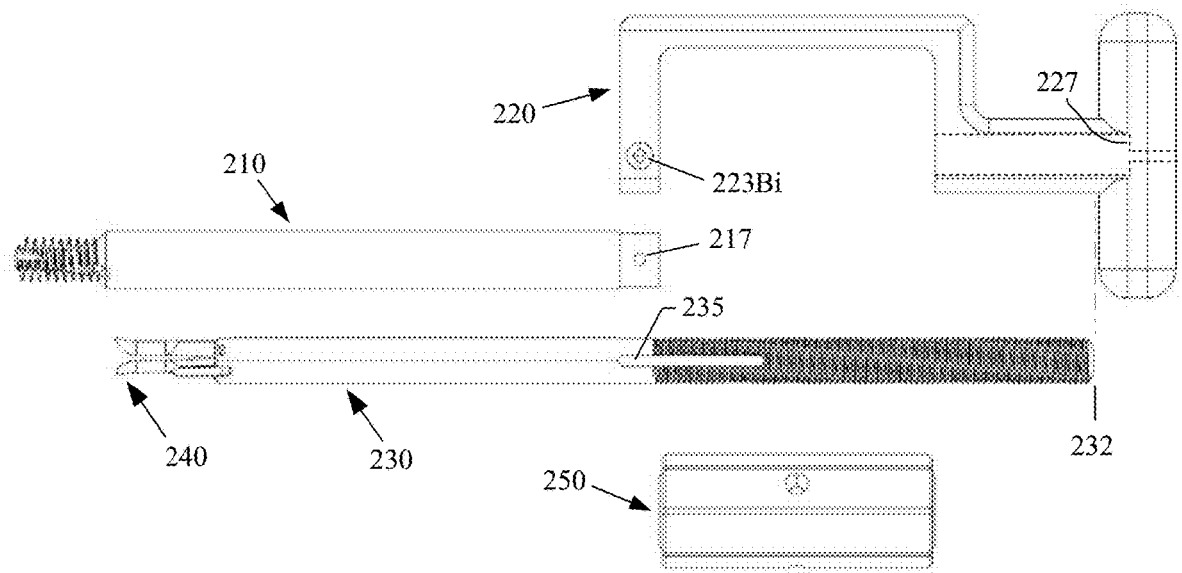
FIG. 18F
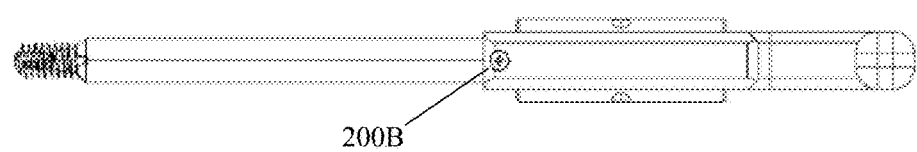
FIG. 18E
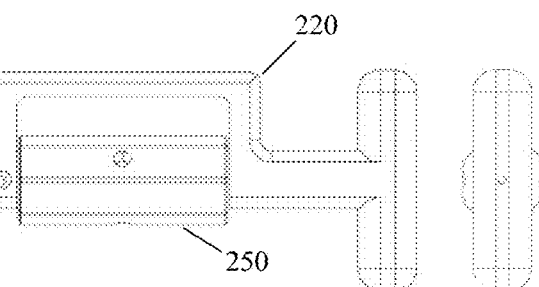
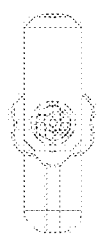
FIG. 18H
FIG. 18G

FIG. 20A
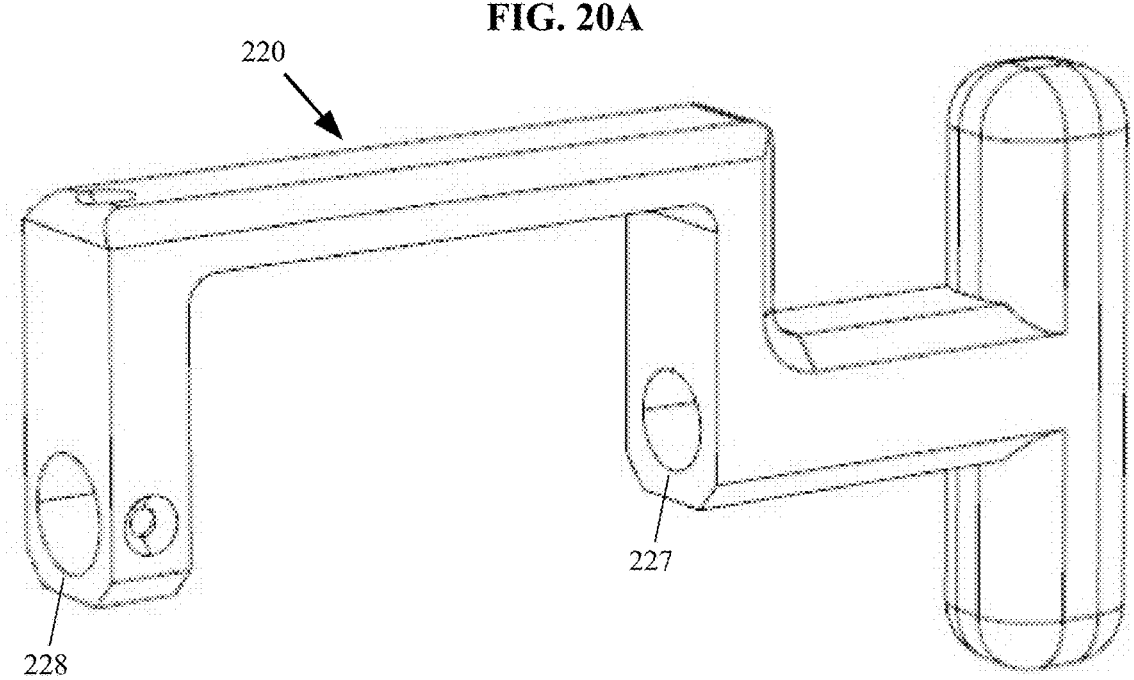
FIG. 20C
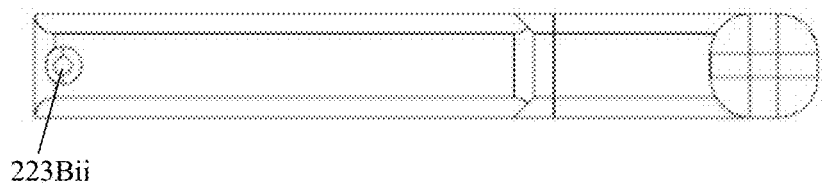
FIG. 20D
FIG. 20B
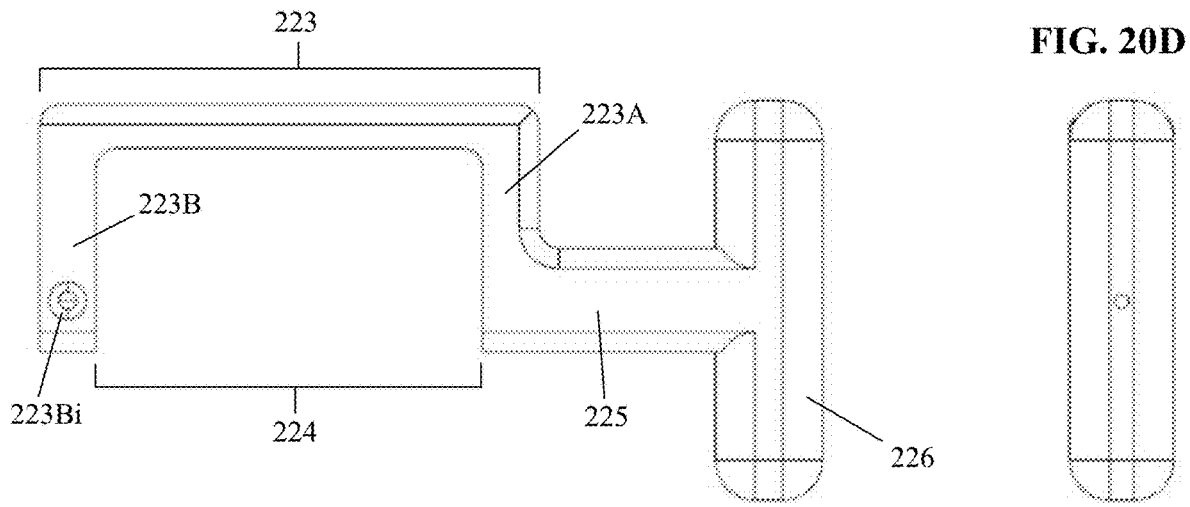

FIG. 22A
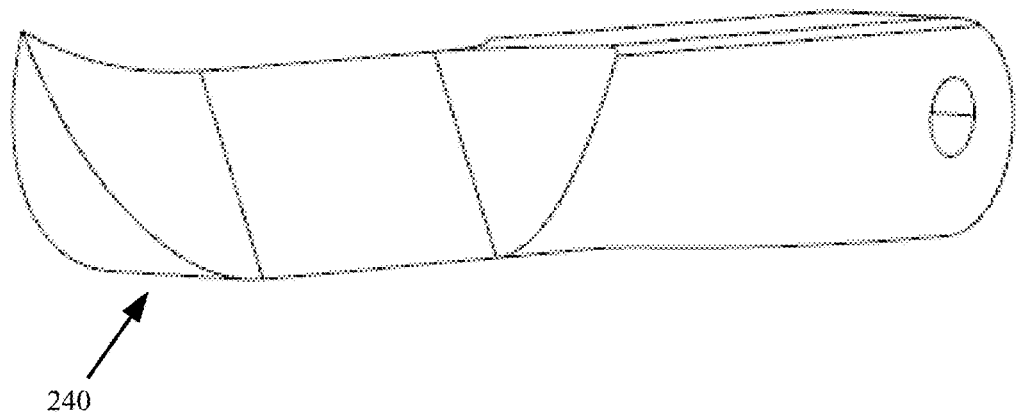
240
FIG. 22C
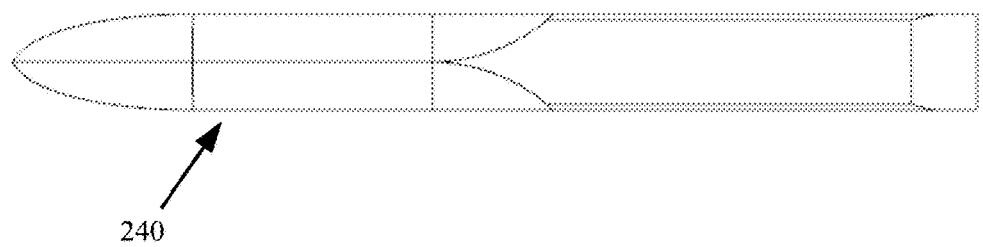
240
FIG. 22B
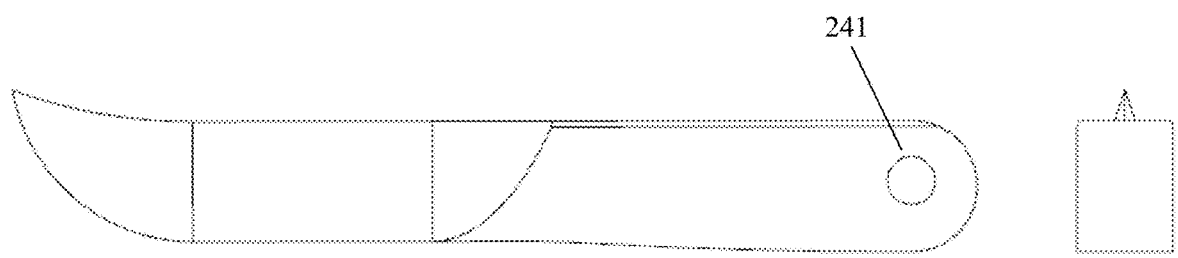
241
FIG. 22D

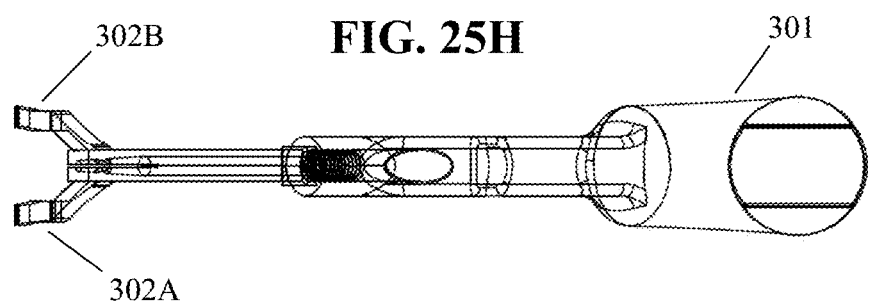
FIG. 25H
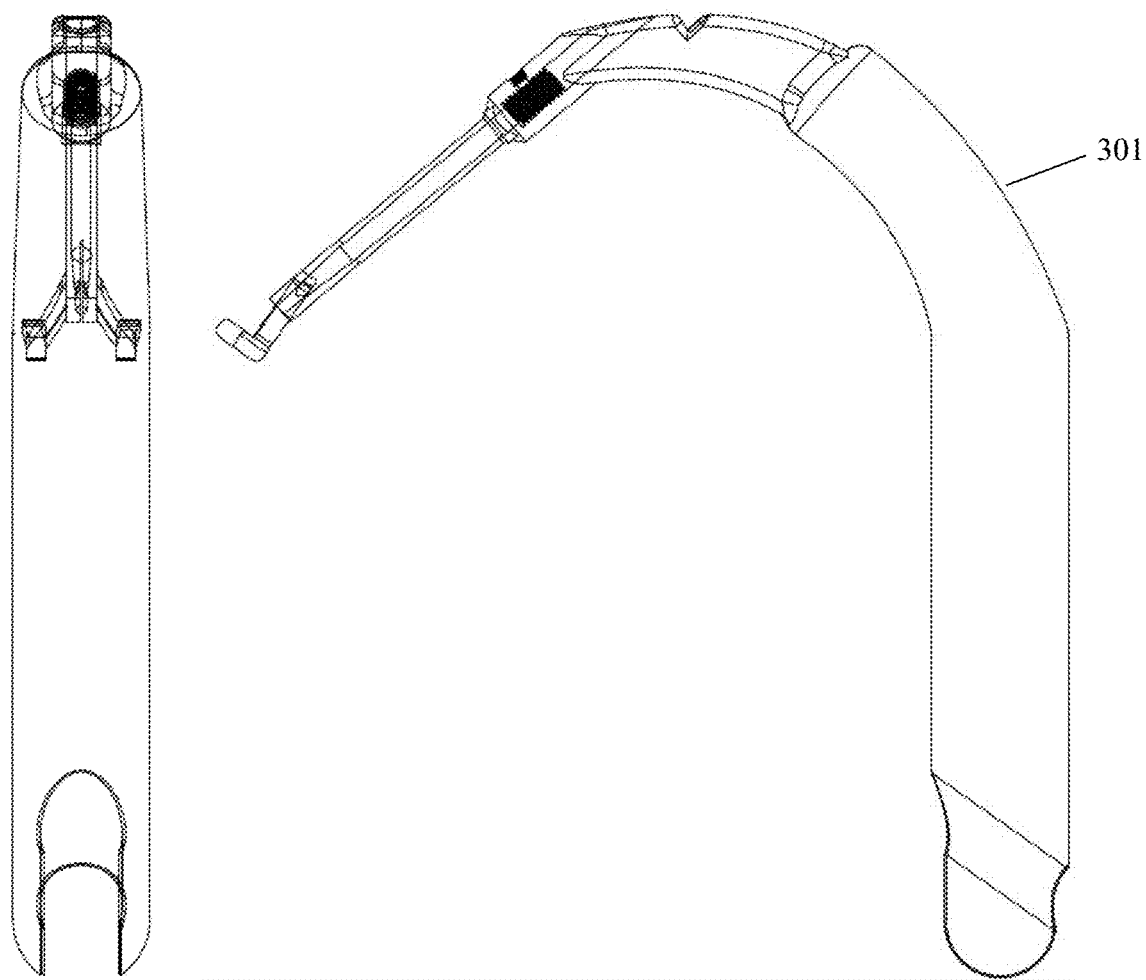
FIG. 25G
FIG. 25I

FIG. 26A
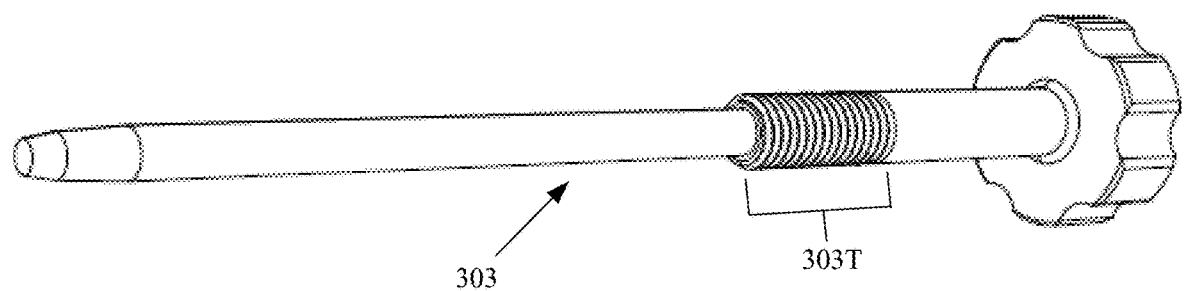
FIG. 26C
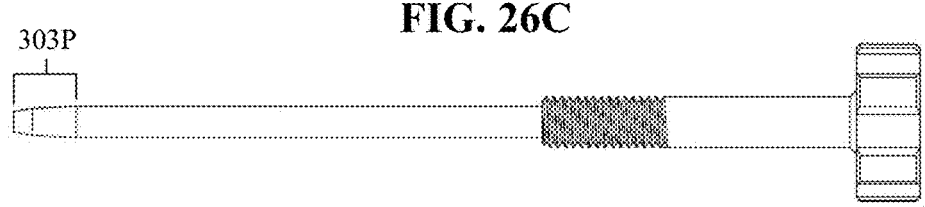
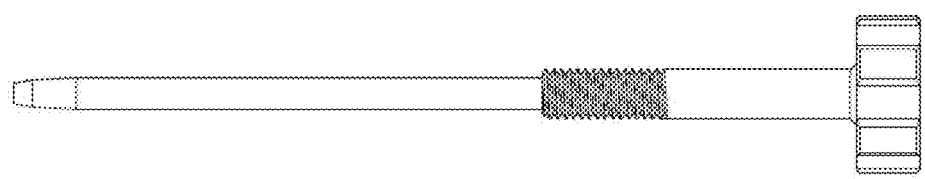
FIG. 26B
FIG. 26D

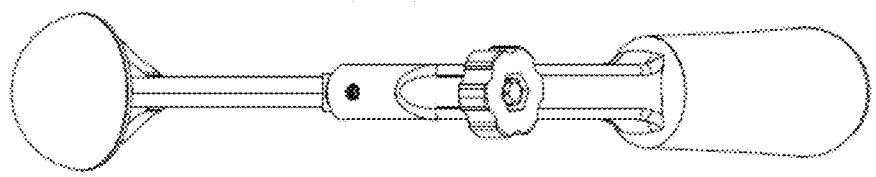
FIG. 28D
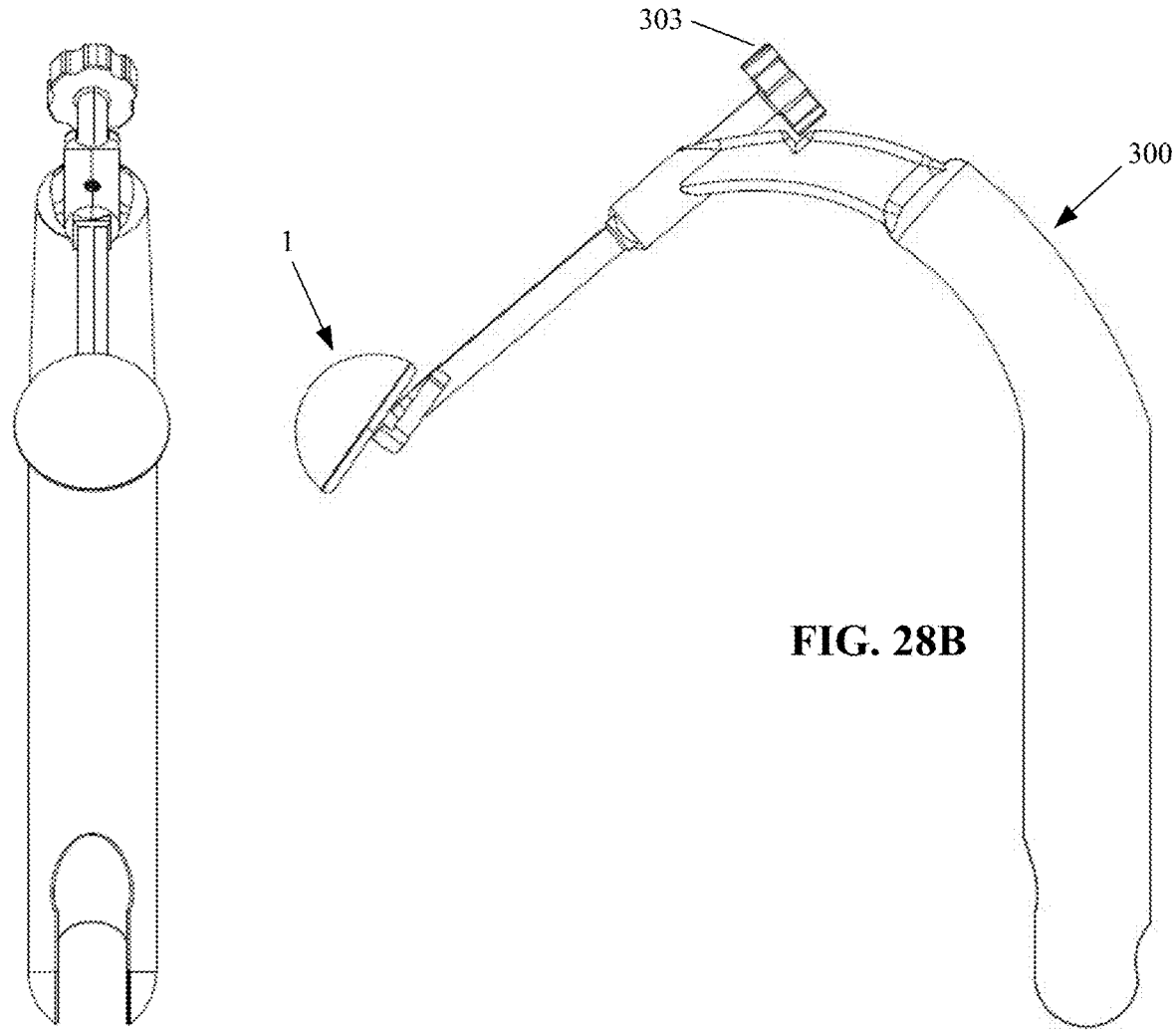
FIG. 28B
FIG. 28C

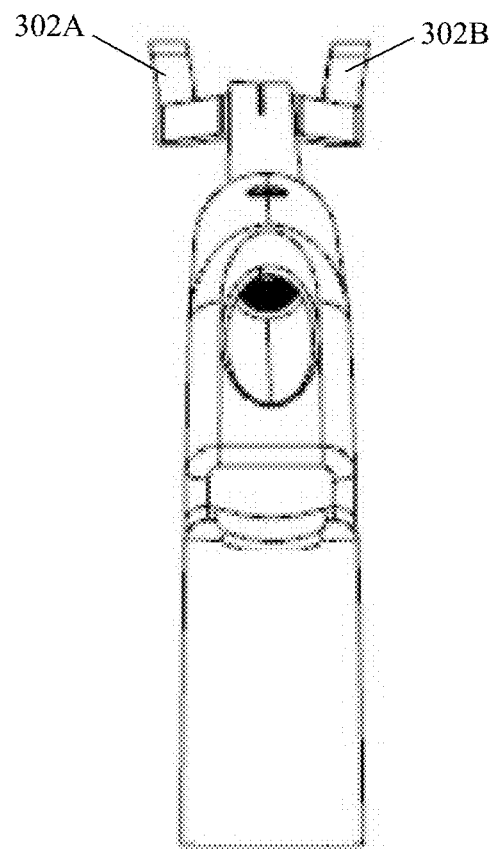
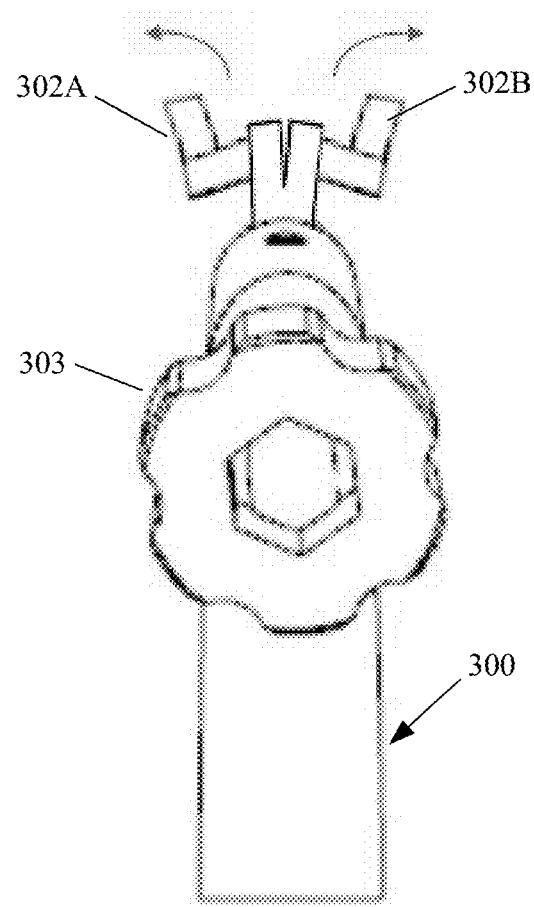
FIG. 28E
(Position of the prongs with no Actuation Member or being without its Knob being rotated)
FIG. 28F
(Prongs are driven to separate after Inserting and Rotating the knob of the Actuation Member)

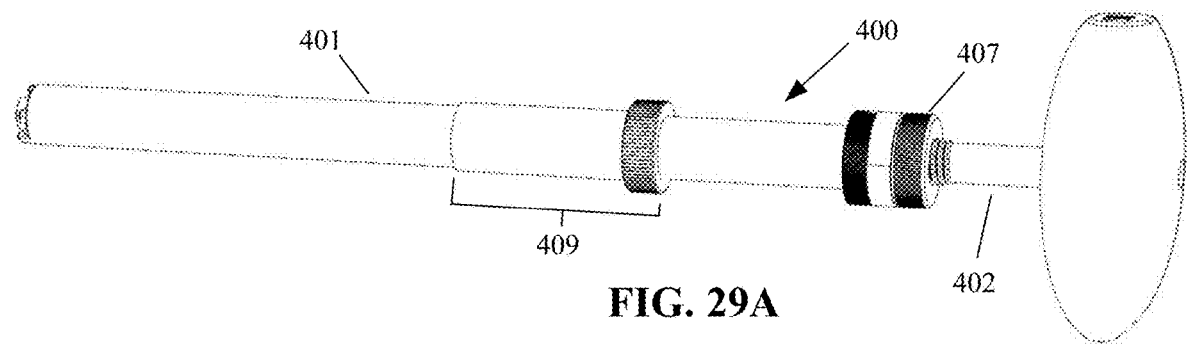
FIG. 29A
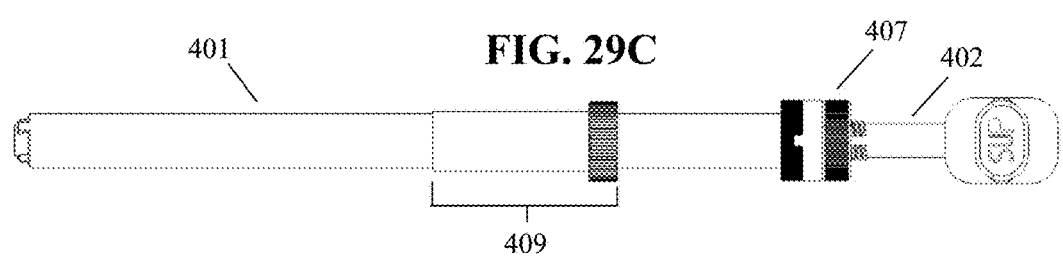
FIG. 29C
FIG. 29B
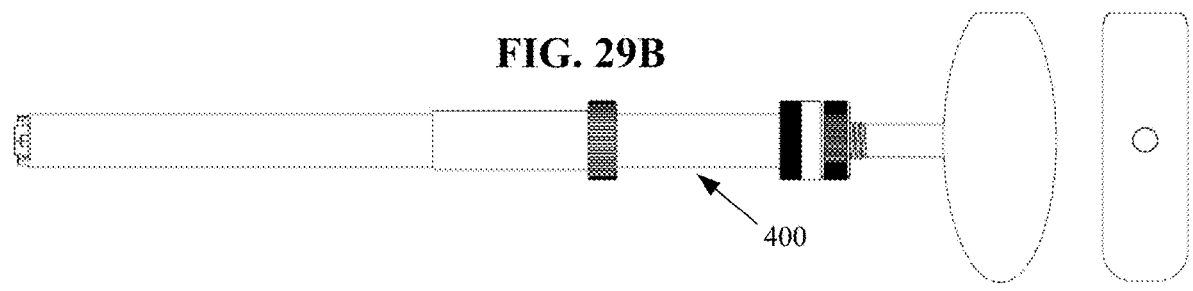
FIG. 29E
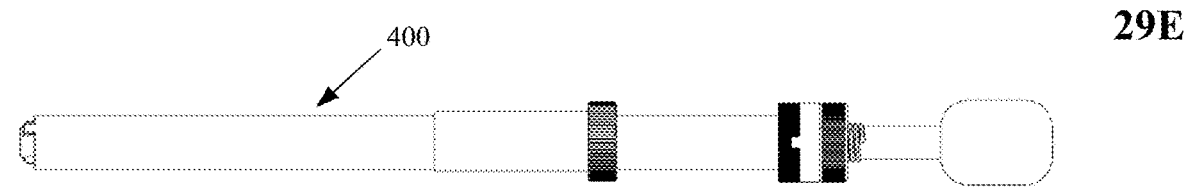
FIG. 29D

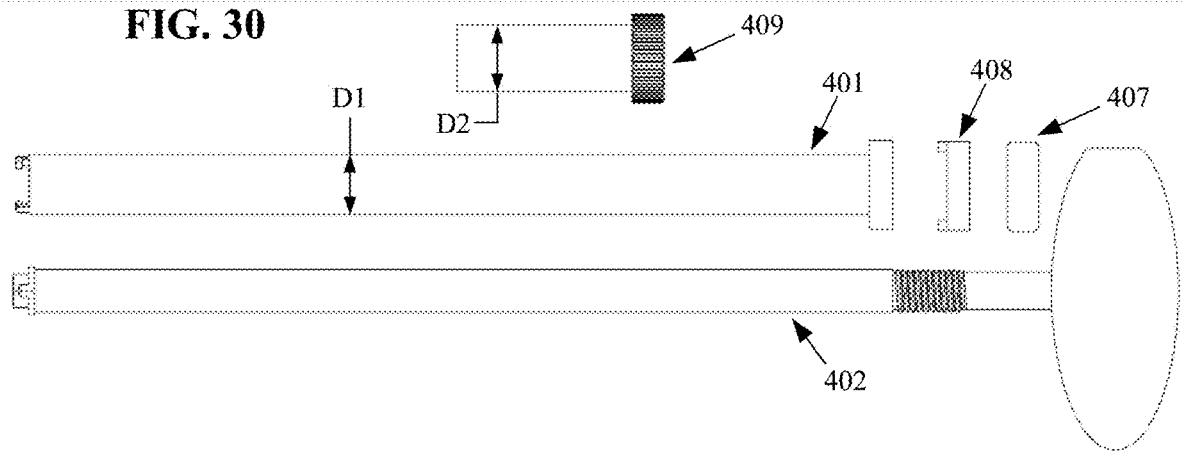
FIG. 30
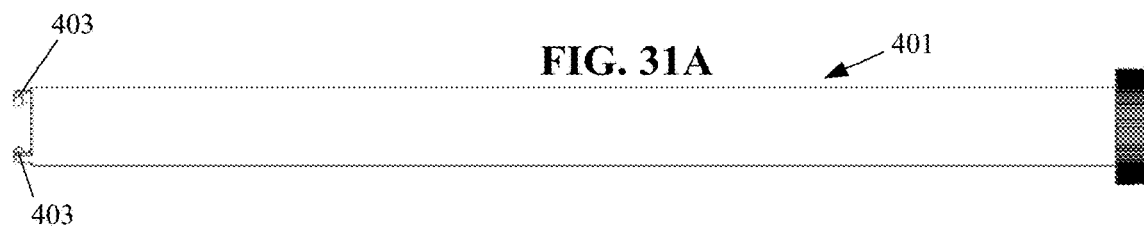
FIG. 31A
FIG. 31B
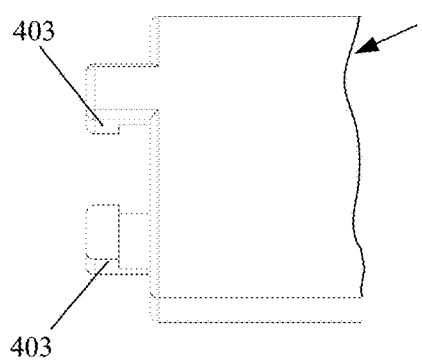
FIG. 31F
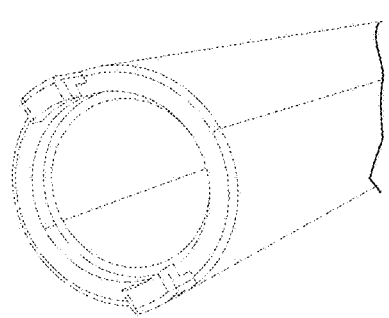
FIG. 31E

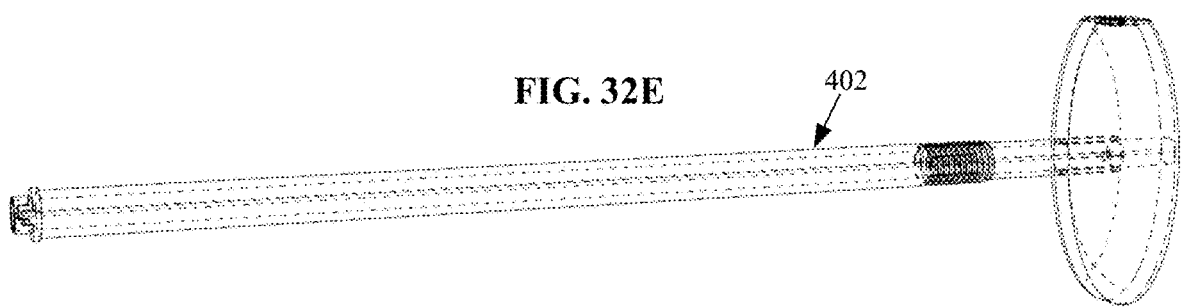
FIG. 32E
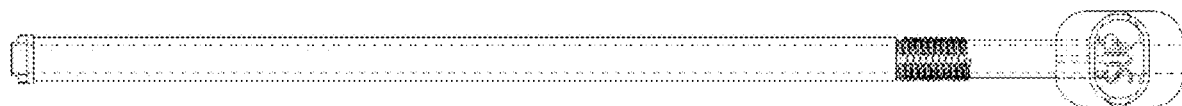
FIG. 32F
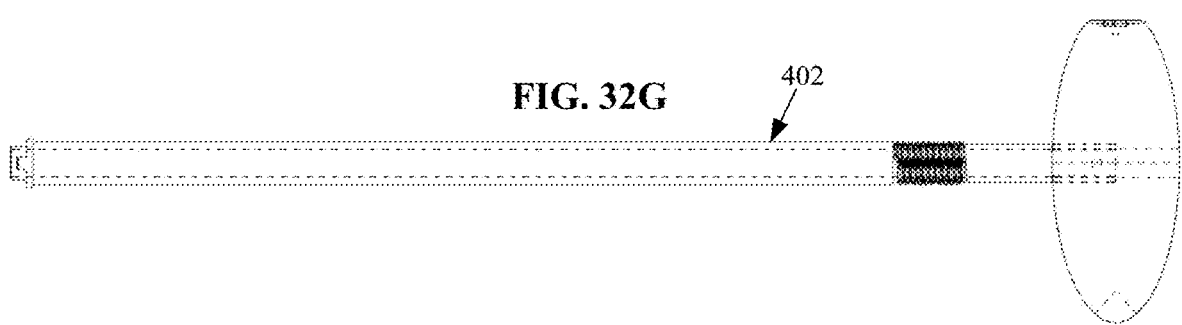
FIG. 32G
FIG. 34A
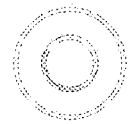
FIG. 33D
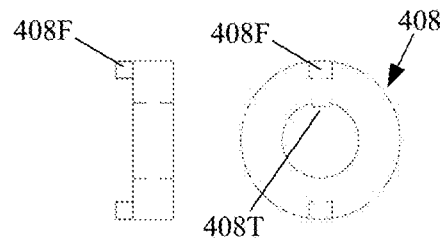
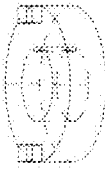
FIG. 34C   FIG. 34B
FIG. 33C   FIG. 33B   FIG. 33A
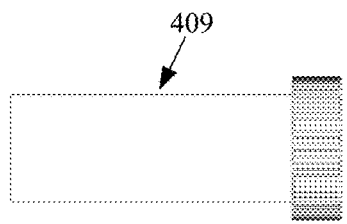
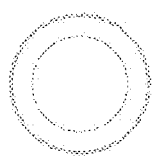
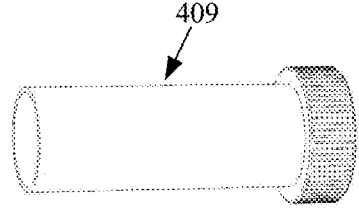
FIG. 35C   FIG. 35B   FIG. 35A

FIG. 36C
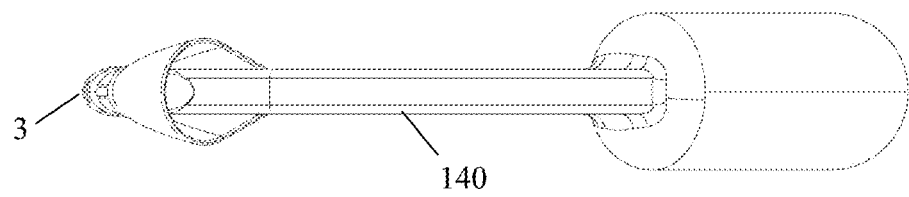
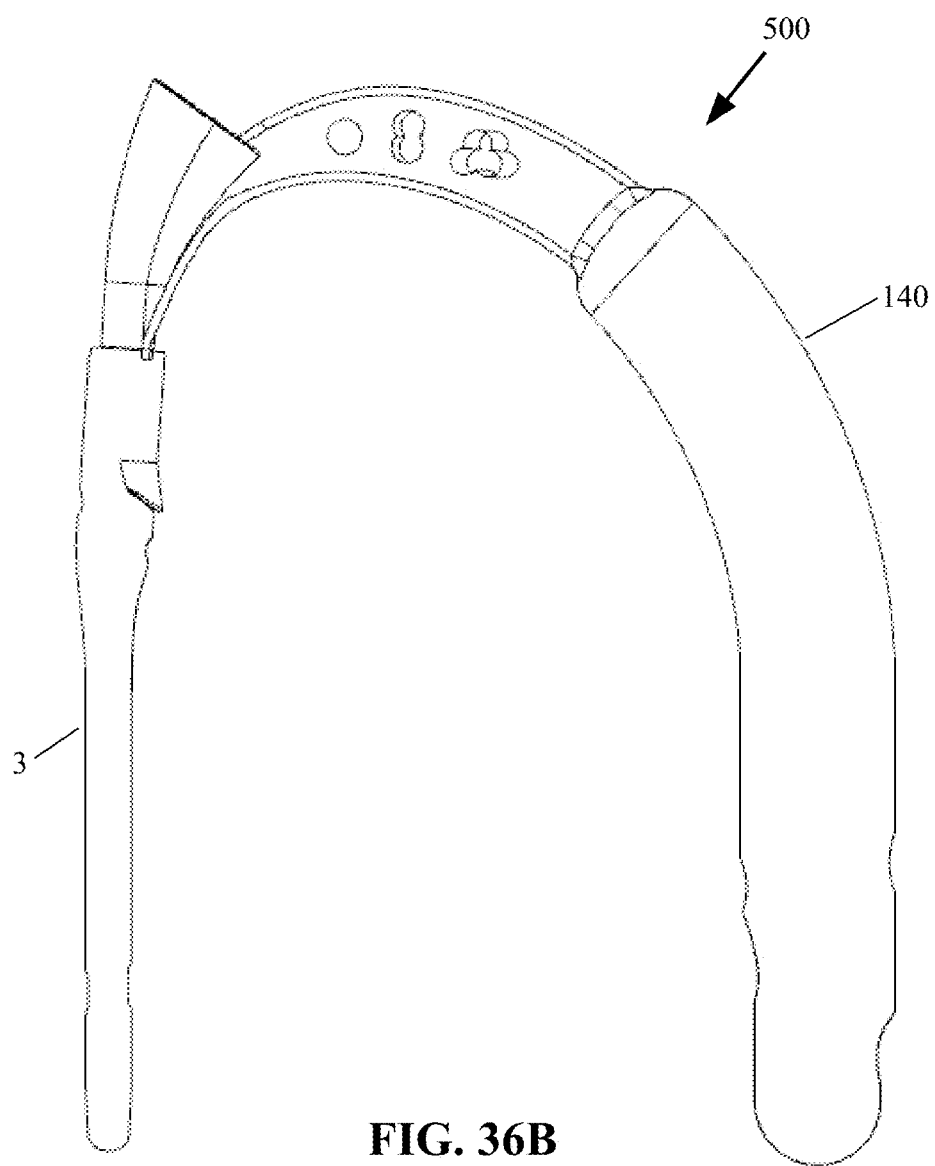
FIG. 36B

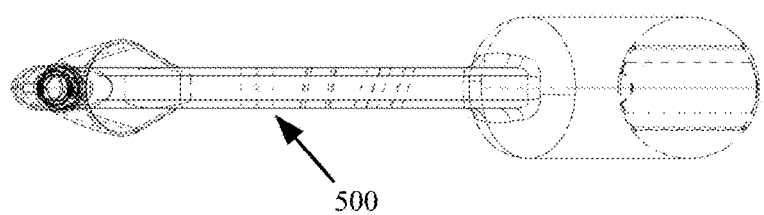
FIG. 36F
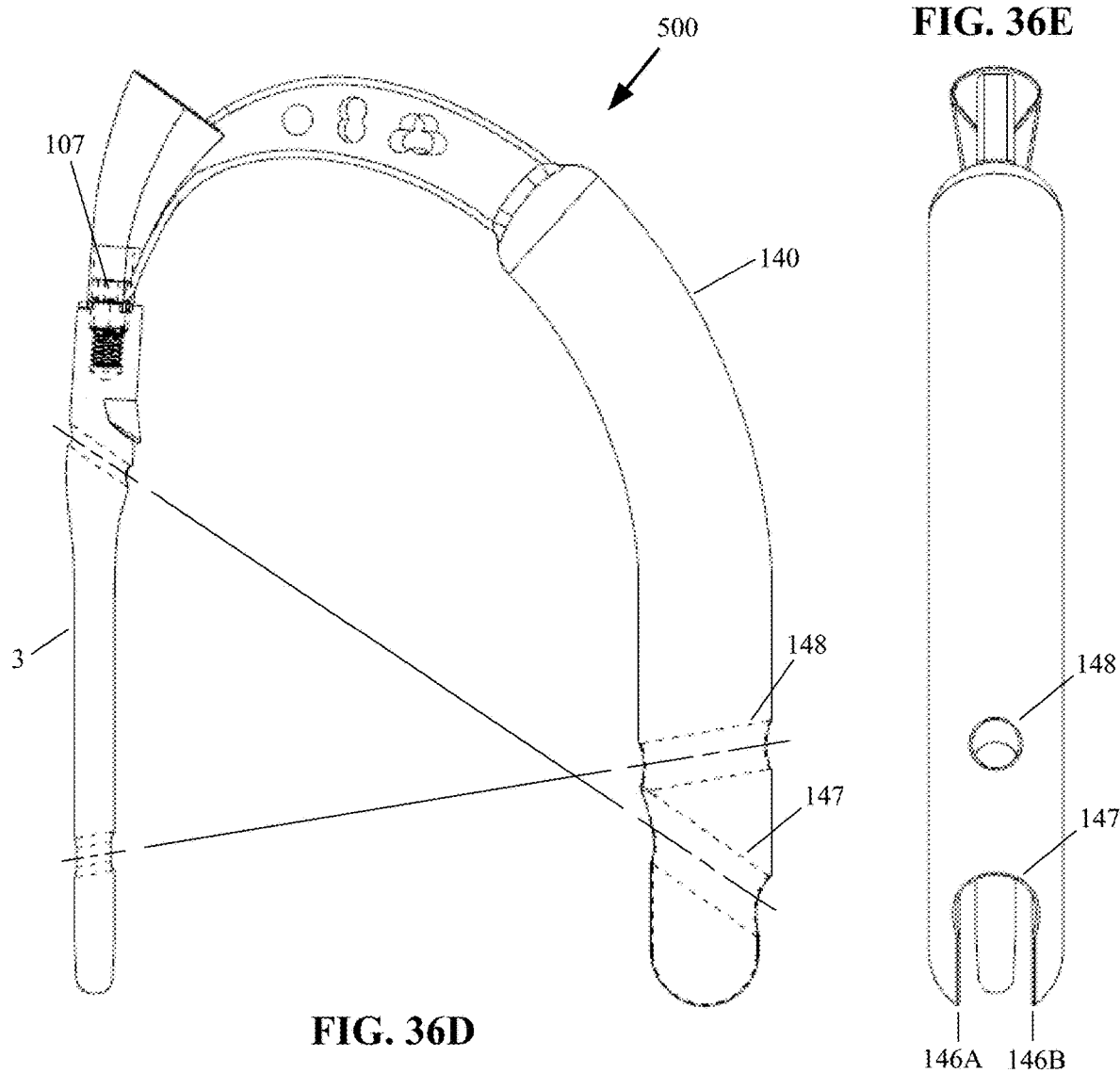
FIG. 36D
FIG. 36E

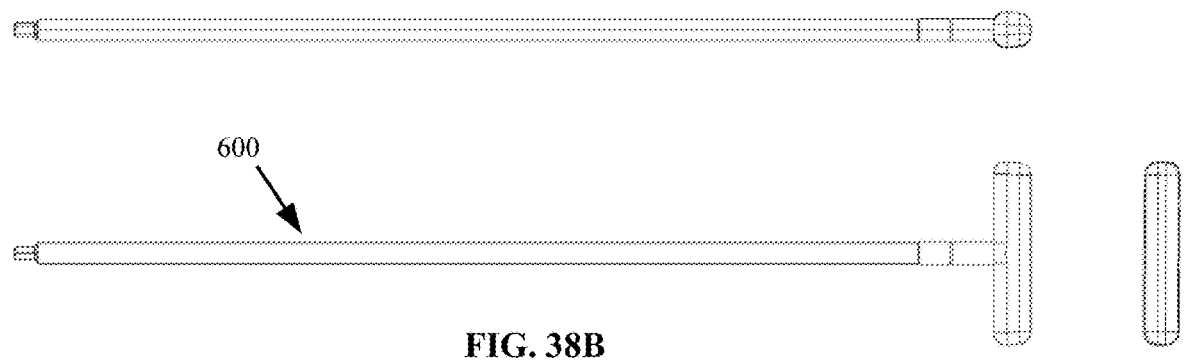
FIG. 38C
FIG. 38B
FIG. 38D
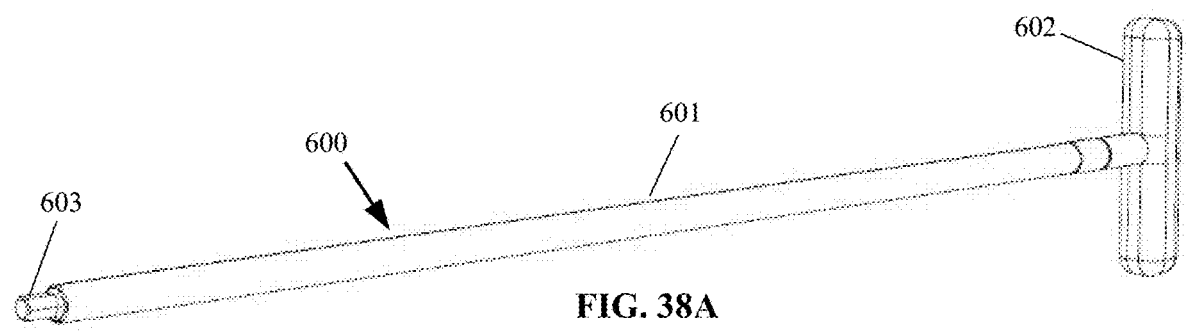
FIG. 38A

HIP OR SHOULDER PROSTHESIS AND PLACEMENT INSTRUMENTS

CROSS REFERENCES TO RELATED APPLICATIONS

This application is a continuation of U.S. application Ser. No. 16/766,863, filed on May 26, 2020, which is a continuation in part of, and claims priority on, PCT/ES2019/070399, filed on Jun. 10, 2019, which claims priority on Application Serial No. ES201830565A, filed in Spain on Jun. 11, 2018, all disclosures of which are incorporated herein by reference. The parent application Ser. No. 16/766,863 also claimed priority on Application Serial No. ES2019238992, filed in Spain on Jun. 10, 2019, and on Application Serial No. ES201931091, filed in Spain on Dec. 10, 2019, all disclosures of which are incorporated herein by reference.

FIELD OF THE INVENTION

The present invention relates to a hip or shoulder prosthesis (or arthroplasty) to replace the head of the femur or of the humerus in any case where required and which can be installed by a method that is relatively unaggressive for the patient.

It also relates to the instruments used for the positioning of the prosthesis, all of which serve to accomplish placement in a minimally invasive manner.

BACKGROUND OF THE INVENTION

In normal medical practice it is sometimes necessary to carry out a hip or shoulder replacement, in other words, to remove the head of the femur or of the humerus and position a device that restores the function of the joint, known as a hip or shoulder prosthesis. The prosthesis may be installed using a procedure known as a hip or shoulder arthroplasty. A hip or shoulder arthroplasty may be required for a patient for different reasons, such as fractures, arthrosis, neoplasia, etc.

However, prosthesis positioning methods, whether for the hip or shoulder, are very aggressive and such surgical procedures involves very significant risks.

Any approach to replace the hip or shoulder joint with a prosthesis in any case where it is required, in order to minimize the aggressive nature of the surgery, must overcome two important problems:
1. How can the femoral/humeral head be removed in a minimally invasive manner, reducing injury to the patient?
2. What type of device can be implanted easily and less aggressively once the femoral/humeral head has been removed?

For the second problem, in the case of the hip joint, the prostheses of U.S. patent application publication numbers U.S. 2003/0060889, U.S. 2016/0256281 and U.S. 2002/0095214 are known. These each comprise replacement prostheses for the acetabulum (hip bone socket), and/or the head of the femur, with the prostheses being made up of smaller elements which are connected to one another in situ.

In the case of the shoulder joint, the removal of the head of the humerus poses similar, although somewhat different problems, due to the size of the joint and of its components.

Other devices/methods that may be related, and which are not admitted herein to be prior art, may be shown by the following patents and patent application publications: EP 1240879; EP 1344505; U.S. 2012/0130502; WO2011028520A2; WO2009052294; U.S. 2018/0078291; and U.S. 2005/0125067.

There remains an unmet need for prosthesis and/or tools and/or corresponding methods that can better address these two initial questions.

The herein disclosed prostheses, placement apparatus, and placement methods provide improvements upon the prior art.

It is noted that citing herein of any patents, published patent applications, and non-patent literature is not an admission as to any of those references constituting prior art with respect to the herein disclosed apparatus.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The following disclosure describes:
A new hip or shoulder prosthesis made up of various parts which are assembled together inside the human body;
The instruments for applying this prosthesis, according to the corresponding claims; and
A procedure for utilizing the instruments to place the prosthesis.

The new hip or shoulder prosthesis and the instruments described in their different embodiments overcome problems associated with the prior art.

Throughout this description, the adjectives 'upper' and 'lower' should be considered as being used in a non-limiting way. Their use is intended to make the description of the invention easier to understand without the need for complex explanations. Specifically, 'upper' should be considered to refer to the area of the element which, at the actual time of use, is closest to the patient's head. Conversely, 'lower' refers to the portion farthest from the patient's head.

One objective of the herein disclosed hip or shoulder prosthesis is to reduce the complications caused by the required hip or shoulder replacement surgery in any case where such kind of surgery is necessary. For this reason, the nature of the design of this prosthesis is characterized by its placement utilizing a surgical technique that is relatively unaggressive.

The design of the prosthesis and the instruments utilized allow percutaneous positioning in a minimally invasive way, minimizing as much as possible the aggressiveness of the surgery compared with a standard hip or shoulder replacement surgery.

In the case of the hip, for placement of the prosthesis, the same incisions are made as for a proximal femoral intramedullary nailing such as Gamma nail made by Stryker or PFNA nail made by Synthes. The prosthesis may also be positioned in the shoulder with two incisions.

The hip or shoulder prosthesis used to replace the femoral or humeral head includes the following components:
1. A head component (in the case of a hip arthroplasty this replaces the head of the femur, and in the case of a shoulder arthroplasty it replaces the head of the humerus). The head component may include a substantially hemispherical-shaped portion that may transition into a rear face that may have a threaded bore and recesses formed therein, which recesses are particularly configured to cooperate with the head component insertion device to facilitate insertion of the head component in the patient's body.
2. A metaphyseal component, which is formed as a generally straight element with an approximately centrally positioned transverse aperture, dividing it into a first section extending towards a first end and a second section extending towards a second end. The first end of the metaphyseal component has a shank portion which is configured to be attached to the threaded bore of the head component. The second end of the metaphyseal component also has a longitudinal hole which transects the transverse aperture and reaches the first section of the metaphyseal component, which is configured to receive the locking device.
3. A diaphyseal nail, which is intended for insertion in the femoral or humeral canal, and which is sometimes referred to as an intramedullary nail or intramedullary rod. This nail has a first portion where one or more fastening apertures for one or more distal screws for fastening to the femur or to the humerus are situated. It also has a second portion partly arranged in the centrally positioned transverse aperture of the metaphyseal component. This second portion has a transverse hole, which, once assembled the diaphyseal nail with the metaphyseal component, has the same direction than the longitudinal hole of the metaphyseal component, and which is configured to receive the locking device.
4. Finally, the prosthesis has a locking device configured to be received in the longitudinal hole of the first section of the metaphyseal component, passing through a portion of the transverse hole of the second portion of the diaphyseal nail, and then being received in the longitudinal hole portion in the second section of the metaphyseal component.

In a first preferred embodiment, the metaphyseal component has grooving over its entire surface.

Preferably, the locking device is threaded at its tip.

More preferably, the nail has a protruding stop in the second portion, above the metaphyseal component and resting thereon, on the side opposite the shank portion.

The invention also relates to various instruments which assist in the positioning of the prosthesis.

Firstly, this relates to a cannulated extractor for the femoral or humeral head which comprises a tubular part with a grip at one end and a drill bit at the opposite end. The drill bit, which may be conical or cylindrical, allows a first Kirschner wire to pass tightly through its tip or center. Thus, the cannulated extractor can be guided to the femoral or humeral head without the tolerance of the passage affecting the result. For the Kirschner wire to pass through, the grip must have the corresponding aperture.

The invention also relates to a Kirschner wire centering device in the femoral or humeral diaphysis, neck and head, which has the general shape of an inverted 'U'. This inverted 'U' is made up of two elements: a centering nail at one end and a handle-guide at the opposite end.

The centering nail is intended for insertion in the femoral or humeral canal and has a vertical opening in its lower portion.

The handle-guide, which remains outside the body once the centering nail has been inserted inside the femur or the humerus, also has a vertical opening in its lower portion, the upper edge of which is aligned with the upper edge of the vertical opening of the centering nail. This alignment may be by means of a sleeve arranged in the vertical opening of the handle-guide. That sleeve has an upper passage, for a first Kirschner wire, aligned with the upper edge of the vertical opening of the centering nail.

The vertical opening may therefore be straight or have a form complementary to that of the sleeve. The sleeve may have another passage for a second Kirschner wire.

The invention also relates to a head component insertion device which also has an inverted 'U' shape, with a handle with an open recess through the lower edge, and with an upper edge oriented towards the bore of the head component which is mounted on the insertion device. For this mounting, the head component insertion device has a support that is compatible with the recesses of the head component, and can be released using an actuator that can be accessed from the outside (from the handle, for example).

In addition, the invention comprises a metaphyseal component insertion device, which consists of a straight, hollow body (e.g., a tube), with a releasable clamping arrangement at one end for coupling of the metaphyseal component thereto, and a gripper at the opposite end.

Preferably, it comprises two tubular coaxial bodies and a clamp which is made up of protrusions, on the outer tubular body, of a bayonet closure for the corresponding clips of the metaphyseal component. It also comprises a thread close to the gripper for locking the relative movement between both tubular bodies.

Finally, the invention also relates to a diaphyseal nail insertion device which can be used with the nail, and which has an inverted 'U' shape, with a hand grip with a groove open towards the lower portion thereof at a first end and a removable connection for the diaphyseal nail at the opposite end. The size of this groove is enough to receive the metaphyseal component insertion device. The hand grip may be the same element as the handle-guide of the Kirschner wire centering device, changing only the centering nail through the removable connection. Further, it may also be the handle of the head component insertion device positioning the support for the head component.

The handle-guide of the centering device, the handle of the head component insertion device and the hand grip of the diaphyseal nail insertion device may each have a unique sets of marks with a different transparency to X-rays from the rest of the device, with different angles.

Other variants of the prosthesis and of the different instruments will be shown below.

BRIEF DESCRIPTION OF THE DRAWINGS

The description of various example embodiments is explained in conjunction with appended drawings, in which:

FIG. 1 is a front view of a prosthetic device, as disclosed herein, shown after being surgically placed in the hip of a patient.

FIG. 2 is a first cross-sectional view, taken through the entire prosthetic device of FIG. 1.

FIG. 2A is a second cross-sectional view, taken through the head component and a portion of the metaphyseal component of the prosthetic device of FIG. 2, being taken at 90 degrees to the cross-section of FIG. 2.

FIG. 3 is front view showing placement of the head component of the prosthetic device of FIG. 2, using the head component insertion device that is particularly configured to co-act with the head component.

FIG. 5C is a front view of the metaphyseal component of the prosthetic device of FIG. 2.

FIG. 5D is a side view of the metaphyseal component of the prosthetic device of FIG. 2.

FIG. 5E is a first end view of the metaphyseal component of the prosthetic device of FIG. 2.

FIG. 5F is a second end view of the metaphyseal component of the prosthetic device of FIG. 2.

FIG. 12Aii is the front view of FIG. 12A, shown just after the centering nail has been inserted into the femoral canal.

FIG. 12Aiii is a front view illustrating the Kirschner wire centering device, after its centering nail has been inserted into the femoral canal of the patient, just prior to the centering sleeve being inserted into a particularly shaped opening in the handle.

FIG. 12Cii is a top view of the arrangement shown in FIG. 12Ci.

FIG. 12Ciii is the front view of FIG. 12Ci, but shown after a second Kirschner wire has been inserted into the lower cannula of the centering sleeve.

FIG. 12Eii illustrates drilling of the lateral cortex of the femur using the cannulated wire prior to using the cannulated extractor.

FIG. 12Hi is a front view similar to the front view of FIG. 12H, being shown after the Kirschner wire has been withdrawn and after initiating of adduction of the limb using the cannulated extractor to cause dislocation of the femoral head from the acetabulum socket.

FIG. 12Hii is the front view of FIG. 12Hi, but shown after the cannulated extractor has caused dislocation of the femoral head from the acetabulum socket.

FIG. 12Hiii is the front view of FIG. 12Hii, but shown after the cannulated extractor has been removed from the femoral head.

FIG. 12Hiv is the front view of FIG. 12Hiii, but shown after the femoral head has been extracted out of the upper incision using, for example, Kocher forceps.

FIG. 12Ji shows the Metaphyseal Component just prior to being bayonet-mounted to the Metaphyseal Component Insertion Device.

FIG. 12Jii is the front view of FIG. 12I, but also shows the Metaphyseal Component bayonet-mounted to the Metaphyseal Component Insertion Device and being introduced through the middle incision, with the Metaphyseal Component Insertion Device cooperating with the opening in the handle guide and being thereby guided.

FIG. 13C the side view of FIG. 13B, but shown without the nut.

FIG. 13D a front view of the prosthesis placement apparatus of FIG. 13B, shown without the nut.

FIG. 13E a rear view of the prosthesis placement apparatus of FIG. 13B, shown without the nut.

FIG. 13F is a top view of the prosthesis placement apparatus of FIG. 13B, shown without the nut.

FIG. 13G is a true view of the openings formed in the handle guide of the prosthesis placement apparatus of FIG. 13B.

FIG. 13H is a perspective view of the nut shown in FIG. 13A.

FIG. 13I is a front view of the nut shown in FIG. 13A.

FIG. 13J is a top view of the nut shown in FIG. 13A.

FIG. 16E is the perspective view of the centering nail as shown in FIG. 15A, but with the hidden features shown using dashed lines.

FIG. 16F is a rear view of the centering nail as shown in FIG. 15B, but with the hidden features shown using dashed lines.

FIG. 16G is a side view of the centering nail as shown in FIG. 15C, but with the hidden features shown using dashed lines.

FIG. 16H is a top view of the centering nail as shown in FIG. 15D, but with the hidden features shown using dashed lines.

FIG. 17A is a perspective view of the sleeve used in combination with the handle guide of FIG. 13A for centering of the Kirschner wire, as shown in FIG. 12B.

FIG. 17B is a front view of the sleeve shown in FIG. 17A.

FIG. 17C is a top view of the sleeve shown in FIG. 17A.

FIG. 17D is a first end view of the sleeve of FIG. 17A.

FIG. 17E is a second end view of the sleeve of FIG. 17A.

FIG. 18D is an exploded view of the component parts of the cannulated extractor of FIG. 18A.

FIG. 18E is a side view of the cannulated extractor of FIG. 18A.

FIG. 18F is a top view of the cannulated extractor of FIG. 18A.

FIG. 18G is a rear view of the cannulated extractor of FIG. 18A.

FIG. 18H is a front view of the cannulated extractor of FIG. 18A.

FIG. 20E is the perspective view of FIG. 20A, but with the interior features shown therein with dash lines.

FIG. 20F is the side view of FIG. 20B, but with the interior features shown therein with dash lines.

FIG. 20G is the top view of FIG. 20C, but with the interior features shown therein with dash lines.

FIG. 20H is the rear view of FIG. 20D, but with the interior features shown therein with dash lines.

FIG. 21A is a perspective view of the actuation member of the cannulated extractor of FIG. 18A.

FIG. 21B is a side view of the actuation member of FIG. 21A.

FIG. 21C is a top view of the actuation member of FIG. 21A.

FIG. 21D is a rear it of the actuation member of FIG. 21A.

FIG. 21E is the perspective view of FIG. 21A, but with the interior features shown therein with dash lines.

FIG. 21F is the side view of FIG. 21B, but with the interior features shown therein with dash lines.

FIG. 21G is the top view of FIG. 21C, but with the interior features shown therein with dash lines.

FIG. 21H is the rear view of FIG. 21D, but with the interior features shown therein with dash lines.

Figure 18A:
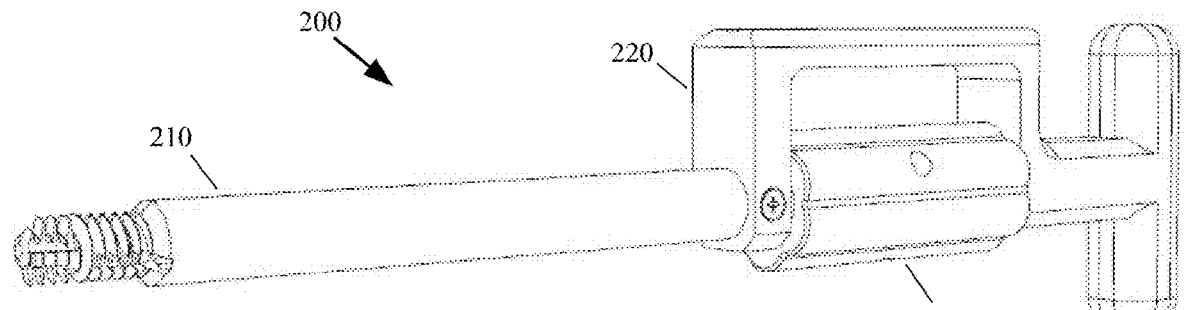
FIG. 18A is a first perspective view of the cannulated extractor, shown with the claws in the retracted position.
Figure 18B:
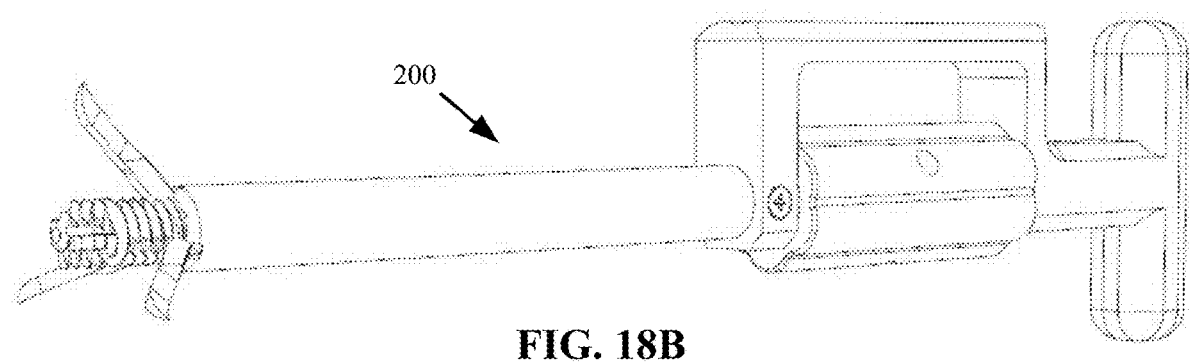
FIG. 18B is a second perspective view of the cannulated extractor, shown with the claws in the extended position.

FIG. 22A is perspective view of one of the claws of the cannulated extractor of FIG. 18A.

FIG. 22B is a side view of the claw of FIG. 22A.

FIG. 22C is a top view of the claw of FIG. 22A.

FIG. 22D is an end view of the claw of FIG. 22A.

Figure 23A:
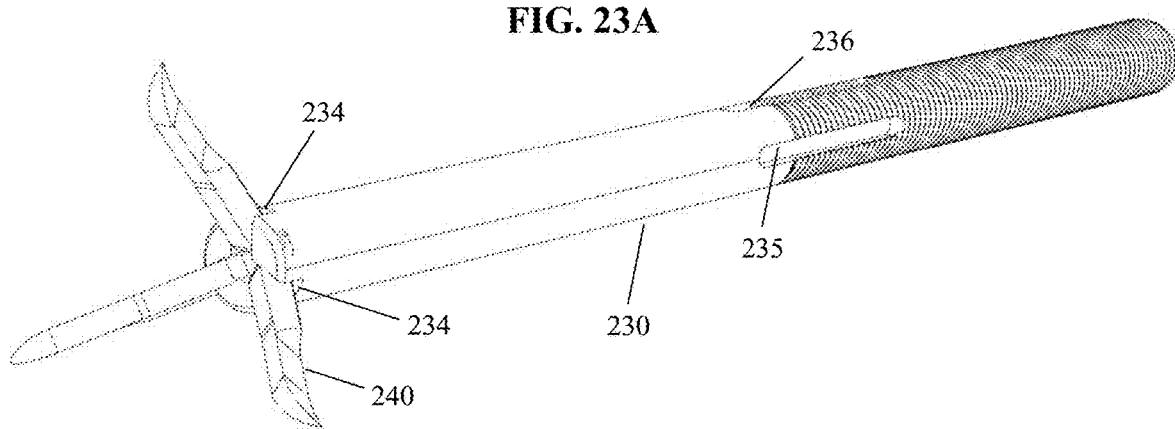

FIG. 23A is a perspective view of the inner shaft member of the cannulated extractor of FIG. 18A, shown with the claws pivotally coupled thereto, and in the extended position.

Figure 23B:
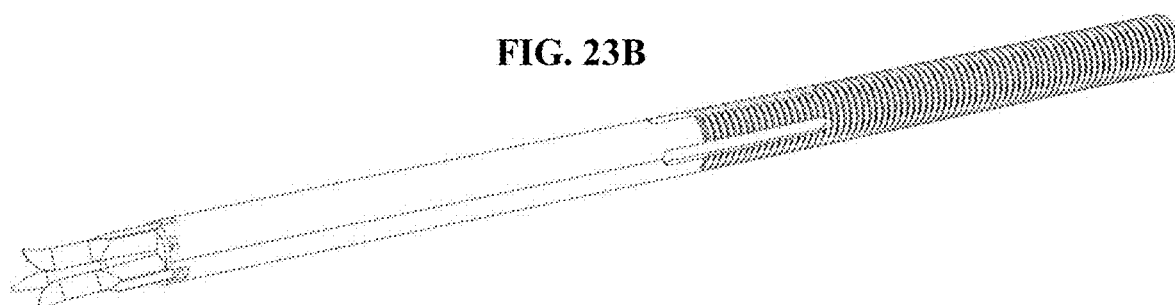

FIG. 23B is the perspective view of FIG. 23A, but shown with the claws in the retracted position.

Figure 23C:
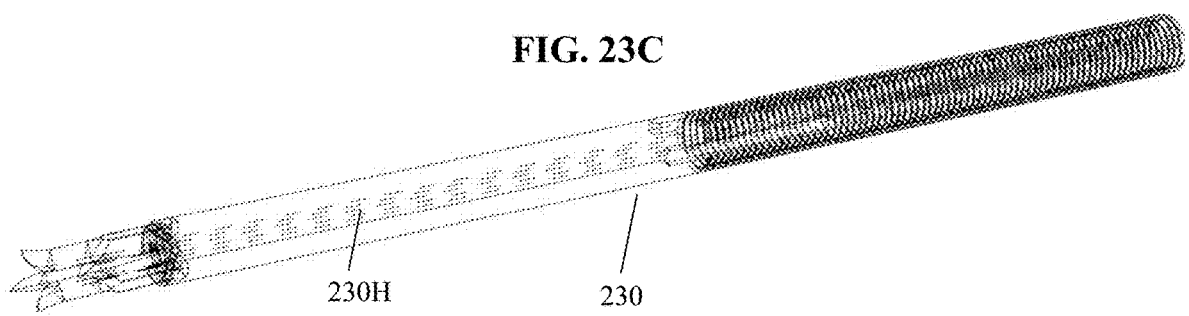

FIG. 23C is the perspective view of FIG. 23B, but with the interior features shown therein with dash lines.

Figure 23D:
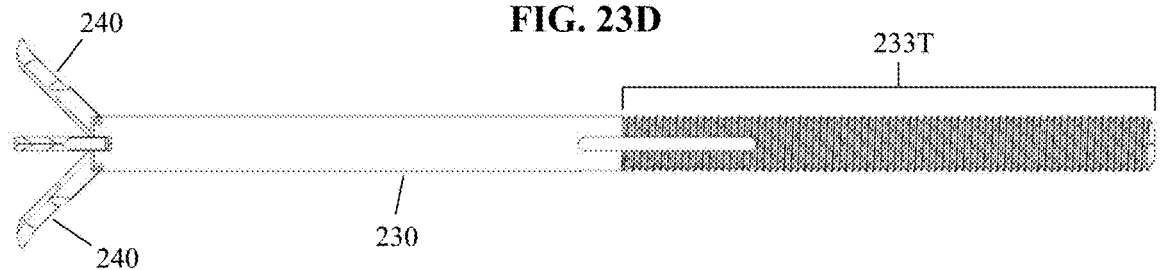

FIG. 23D is a top view of the inner shaft member and claws of FIG. 23A.

Figure 23E:
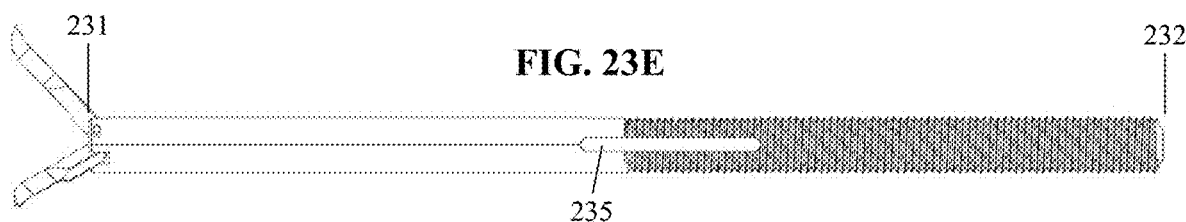

FIG. 23E is a side view of the inner shaft member and claws of FIG. 23A.

Figure 23F:
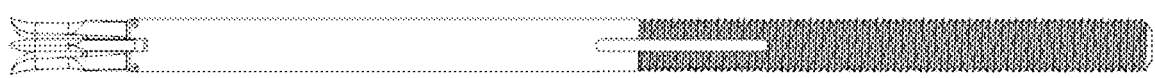

FIG. 23F is the top view of FIG. 23D, but shown with the claws in the retracted position.

Figure 23G:
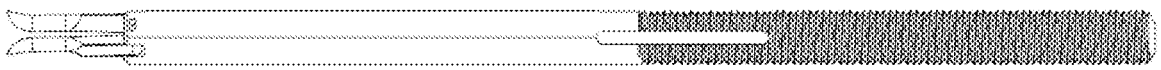

FIG. 23G is the side view of FIG. 23E, but shown with the claws in the retracted position.

Figure 23H:
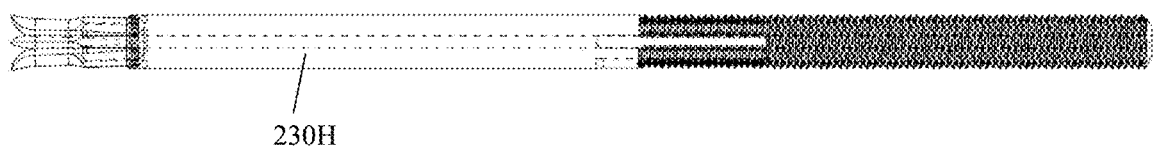

FIG. 23H is the top view of FIG. 23F, but with the interior features shown therein with dash lines.

Figure 23I:
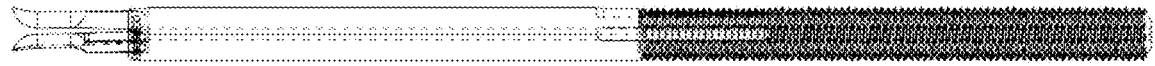

FIG. 23I is the side view of FIG. 23G, but with the interior features shown therein with dash lines.

Figure 23K:
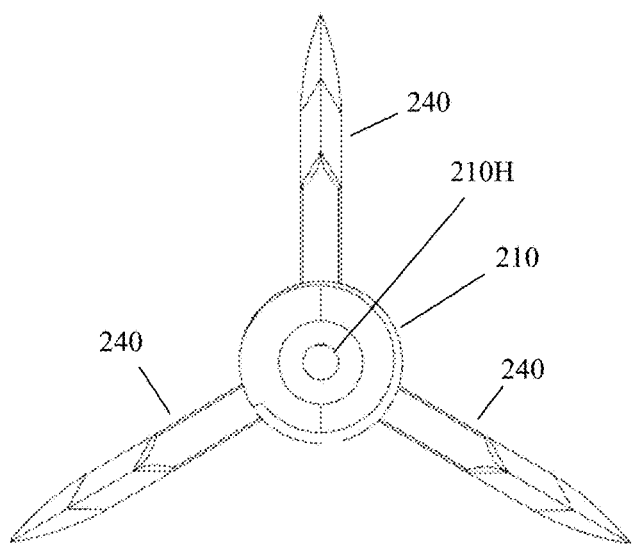
Figure 23J:
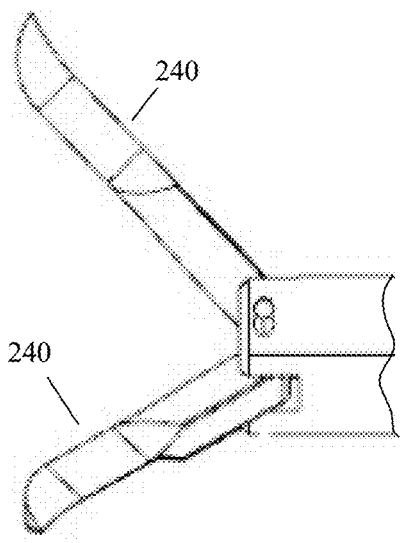

FIG. 23J is the side view of FIG. 22E, but showing the end of inner shah member with the claws greatly enlarged FIG. 23K is an end view of the inner shaft member and claws, as shown in FIG. 23J.

Figure 24A:
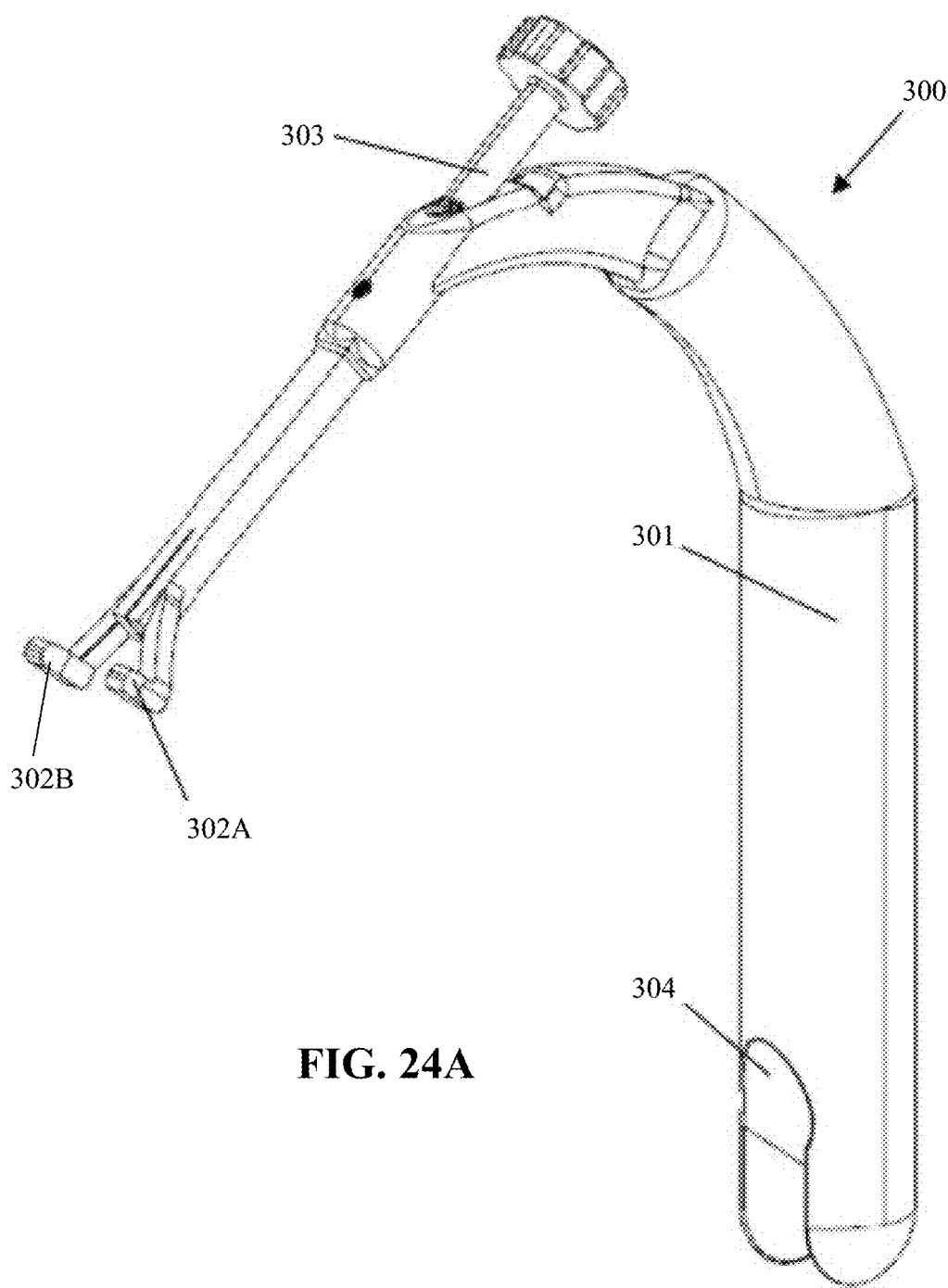

FIG. 24A is a perspective view of the head component insertion device.

Figure 24B:
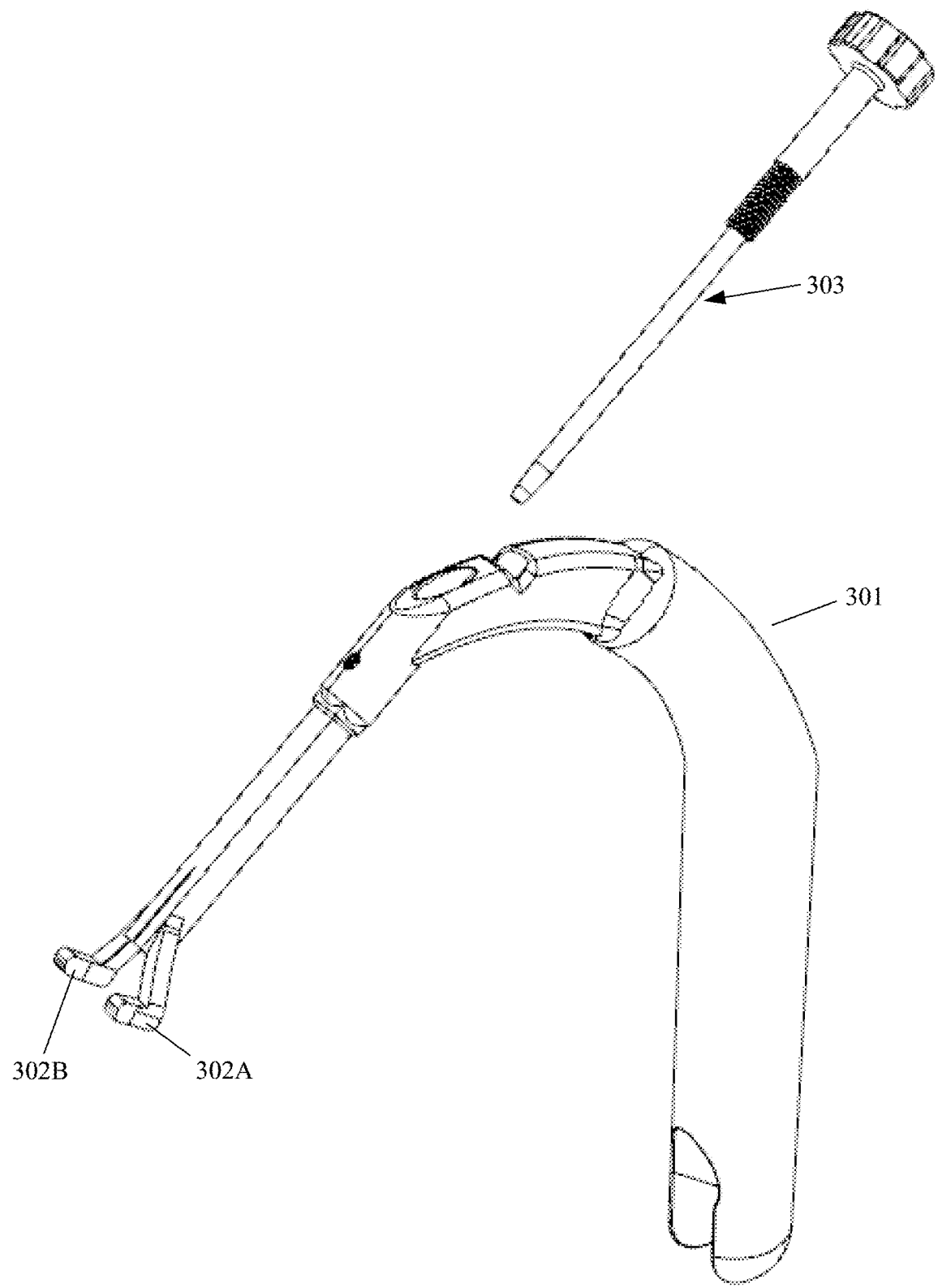

FIG. 24B is an exploded view showing the actuation member prior to being rotatably coupled to the handle member.

Figure 25A:
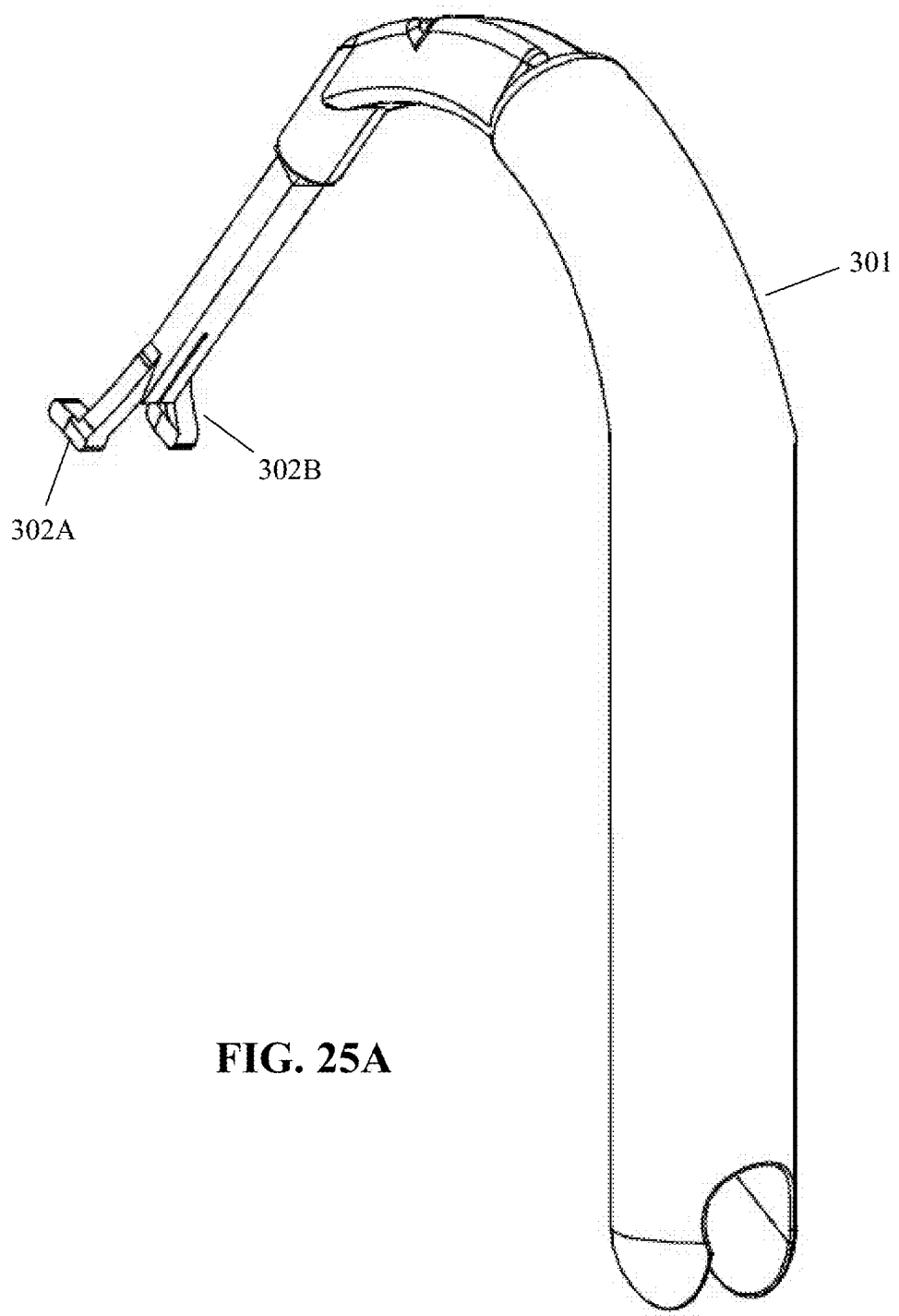

FIG. 25A is a reverse perspective view showing the prongs of the head component insertion device of FIG. 24A movably mounted to the handle portion of the device.

Figure 25C:
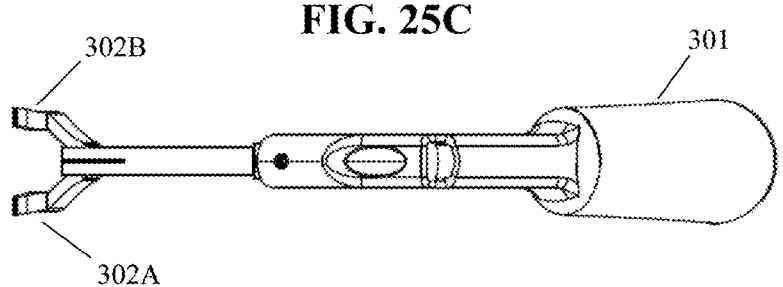
Figure 25D:
Figure 25B:
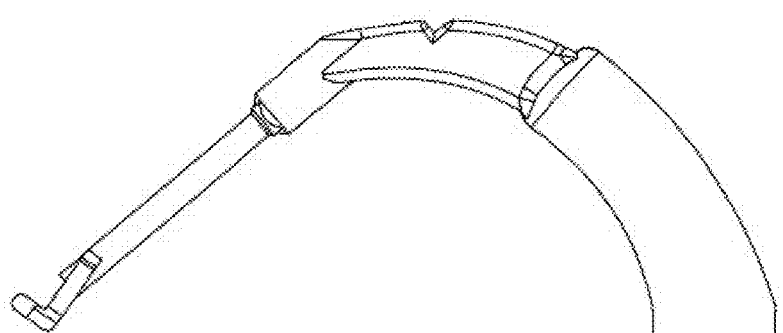

FIG. 25B is a side view of the prongs movably mounted to the handle portion of the head component insertion device, as seen in FIG. 25A.

FIG. 25C is a top view of the prongs movably mounted to the handle portion of the head component insertion device, as seen in FIG. 25A.

FIG. 25D is a front view of the prongs movably mounted to the handle portion of the head component insertion device, as seen in FIG. 25A.

Figure 5A:
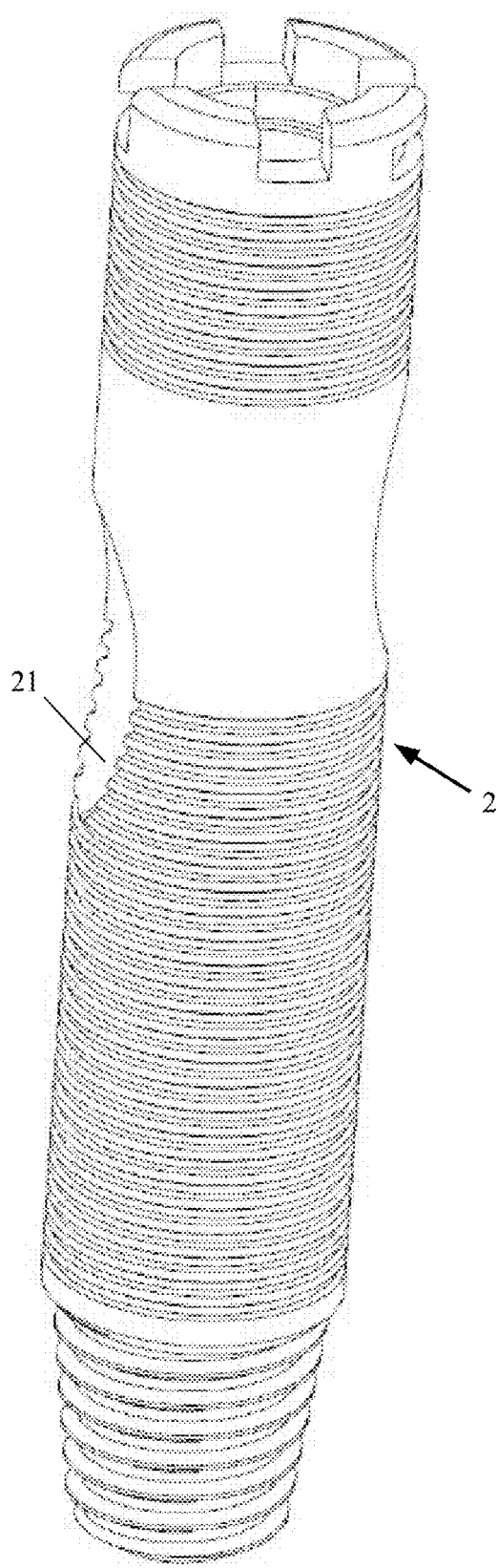
FIG. 5A is a perspective view of the metaphyseal component of the prosthetic device of FIG. 2.
Figure 5B:
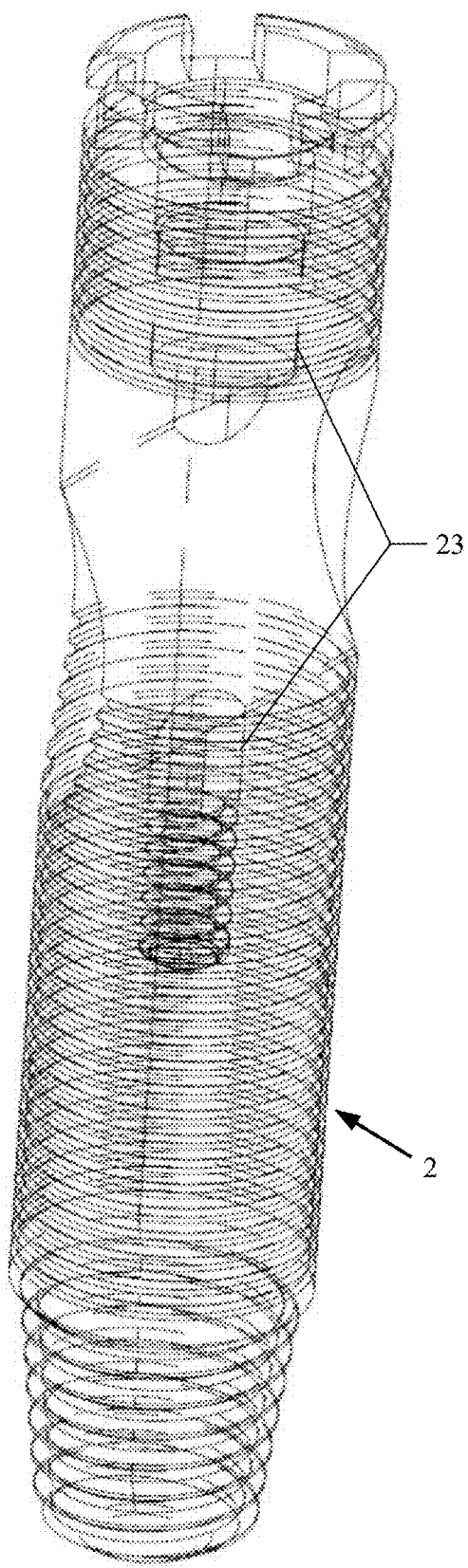
FIG. 5B is a transparent perspective view of the metaphyseal component of the prosthetic device of FIG. 2.
Figure 5G:
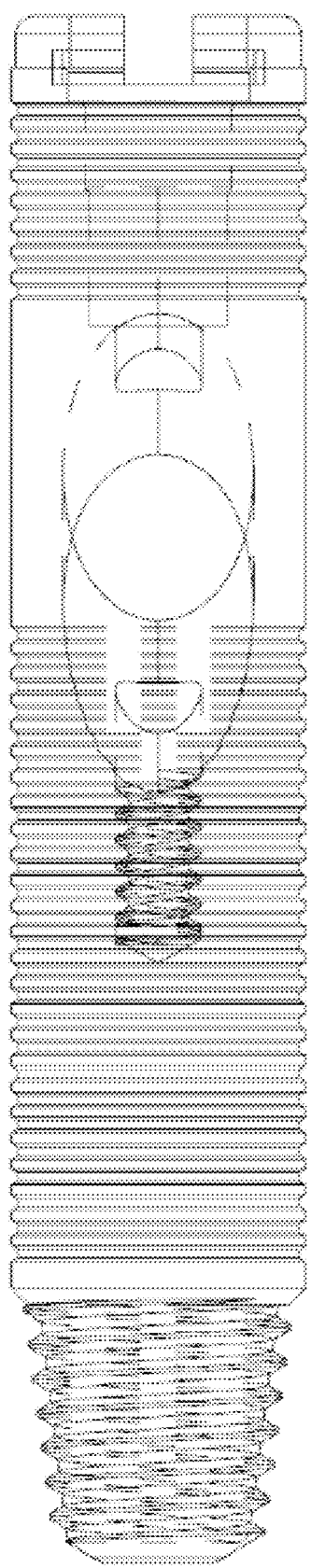
FIG. 5G is a transparent front view of the metaphyseal component of the prosthetic device of FIG. 2.
Figure 5H:
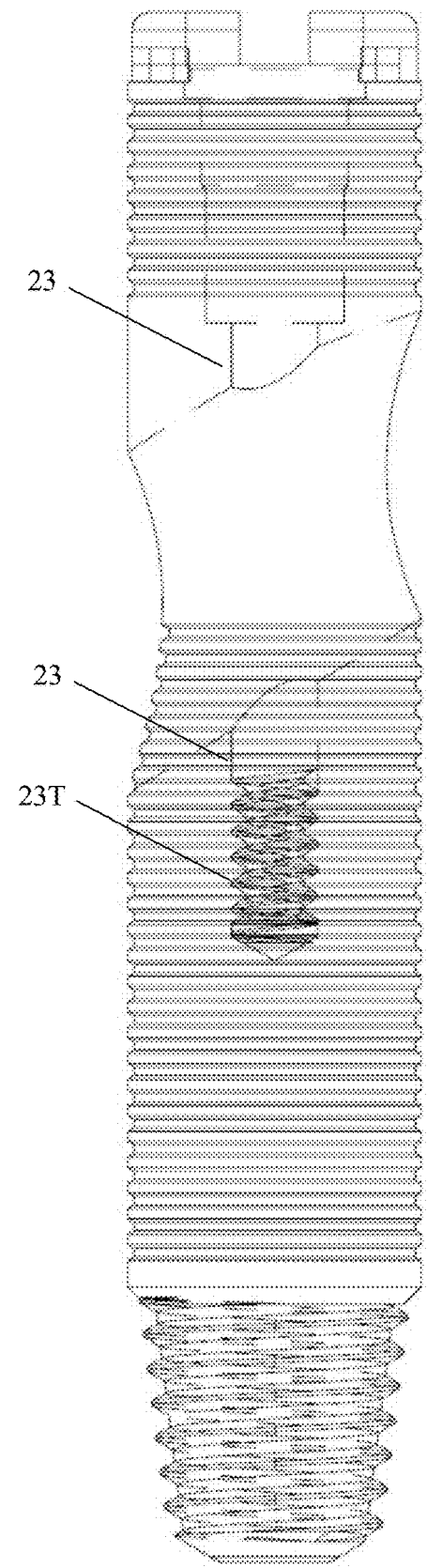
FIG. 5H is a transparent side view of the metaphyseal component of the prosthetic device of FIG. 2.
Figure 25E:
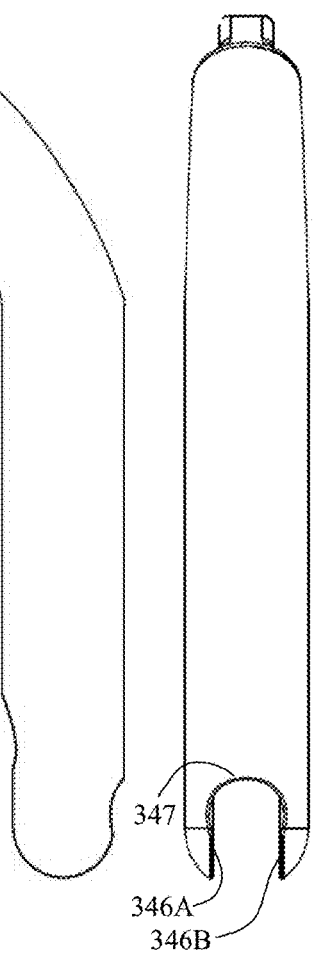

FIG. 25E is a rear view of the prongs movably mounted to the handle portion of the head component insertion device, as seen in FIG. 5A.

Figure 25F:
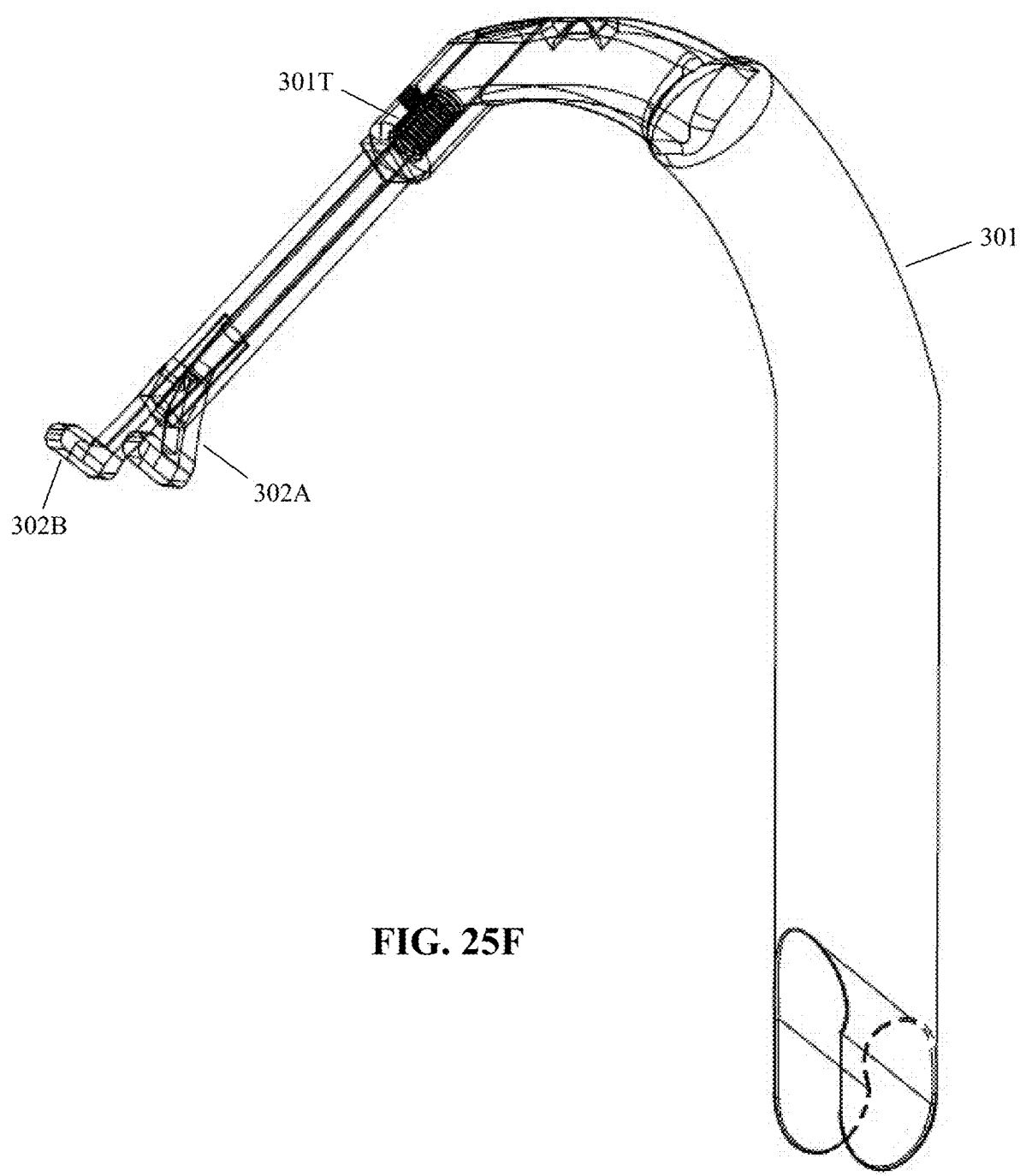

FIG. 25F is the reverse perspective view of FIG. 25A, but is a transparent view showing the hidden features.

FIG. 25G is the side of FIG. 25B, but is a transparent view showing the hidden features.

FIG. 25H is the top view of FIG. 25C, but is a transparent view showing the hidden features.

FIG. 25I is the front view of FIG. 25D, but is a transparent view showing the hidden features.

FIG. 26A is a perspective view of the actuation member that is rotatably coupled to the handle portion of the head component insertion device, and which may be rotated to move the prongs.

FIG. 26B is a front view of the actuation member of FIG. 26A.

FIG. 26C is a top view of the actuation member of FIG. 26A.

FIG. 26D is an end view of the actuation member of FIG. 26A.

Figure 4A:
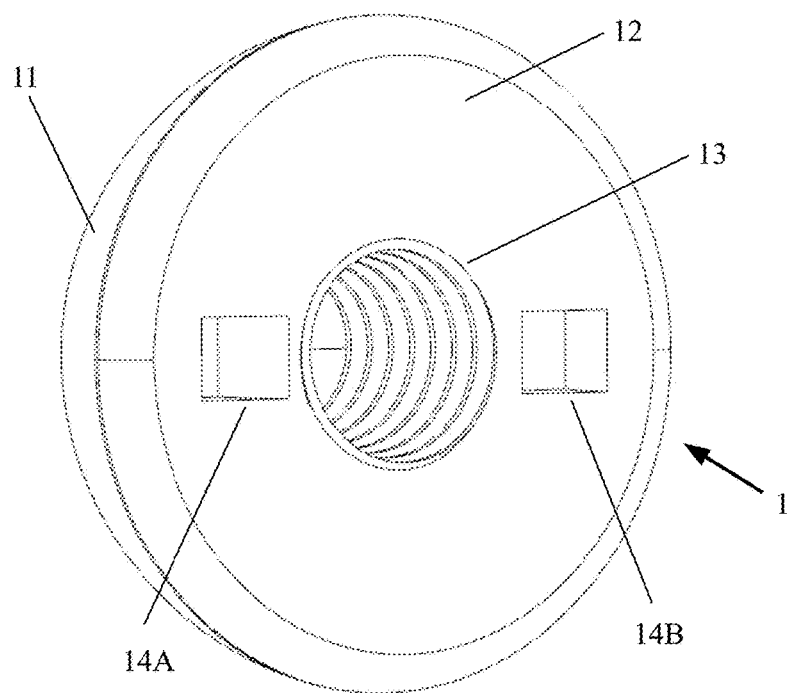
FIG. 4A is a perspective view of the head component of the prosthetic device of FIG. 2.
Figure 4B:
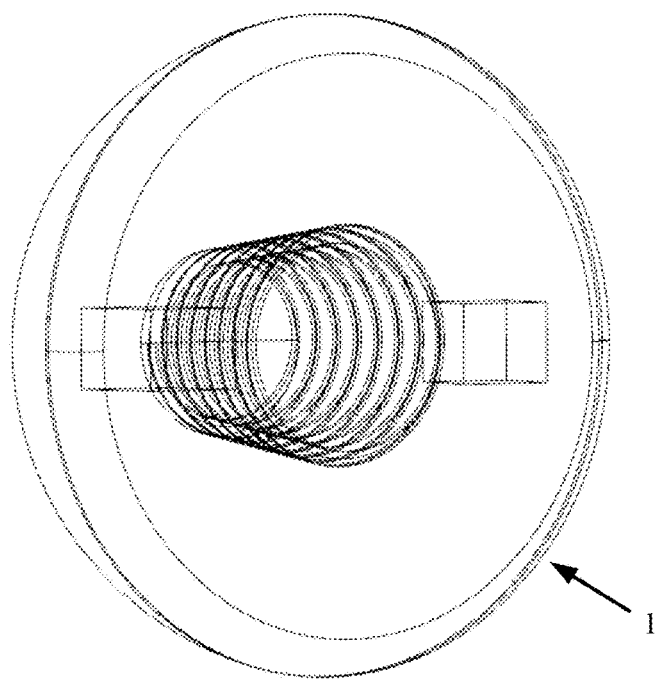
FIG. 4B is a transparent perspective view of the head component of the prosthetic device of FIG. 2.
Figure 4E:
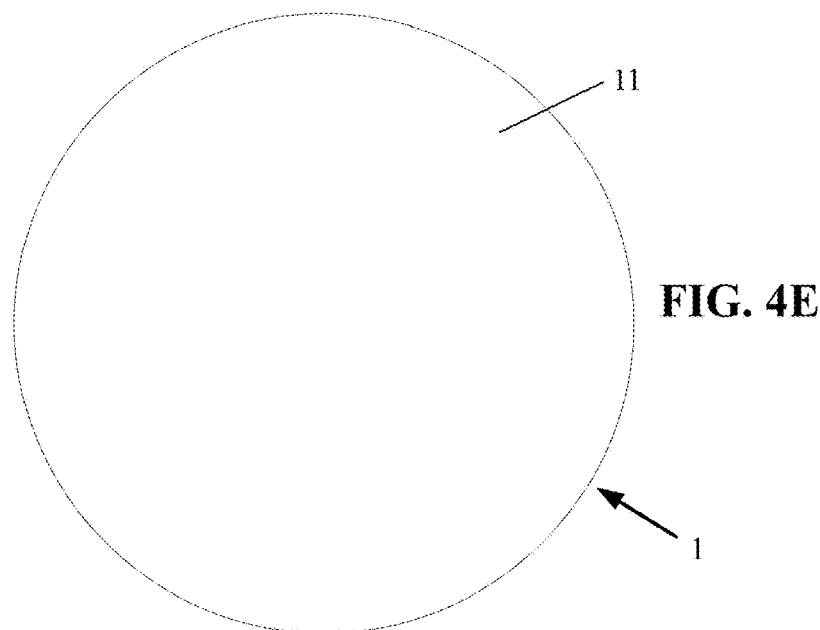
FIG. 4E is a front view of the head component of the prosthetic device of FIG. 2.
Figure 4D:
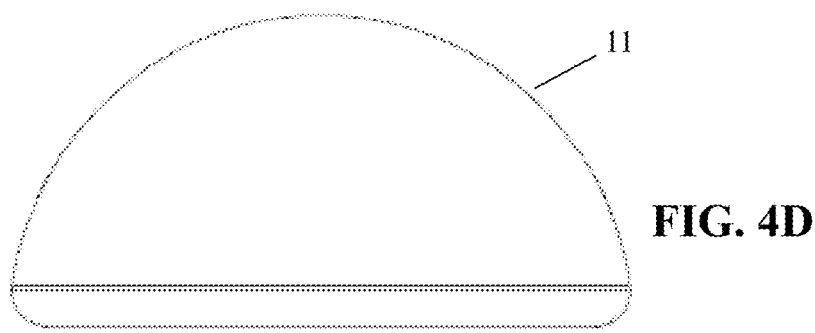
FIG. 4D is a side view of the head component of the prosthetic device of FIG. 2.
Figure 4C:
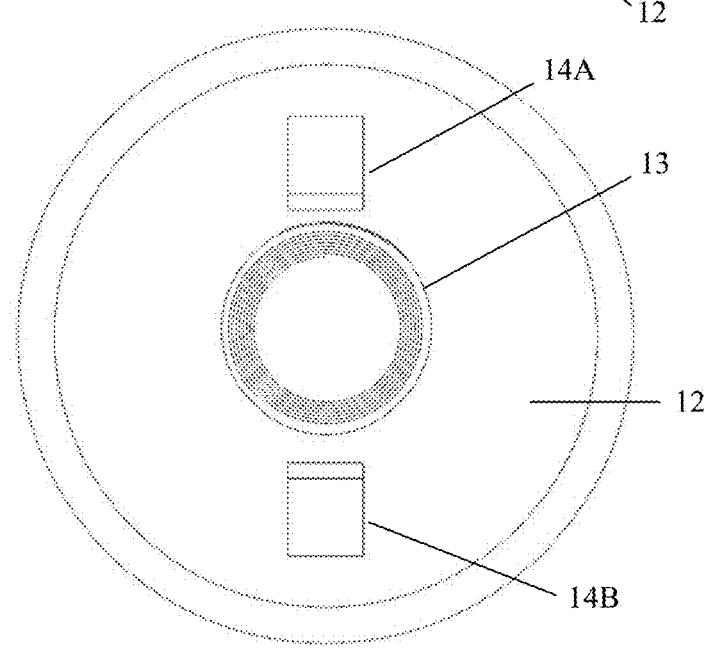
FIG. 4C is a rear view of the head component of the prosthetic device of FIG. 2.
Figure 27A:
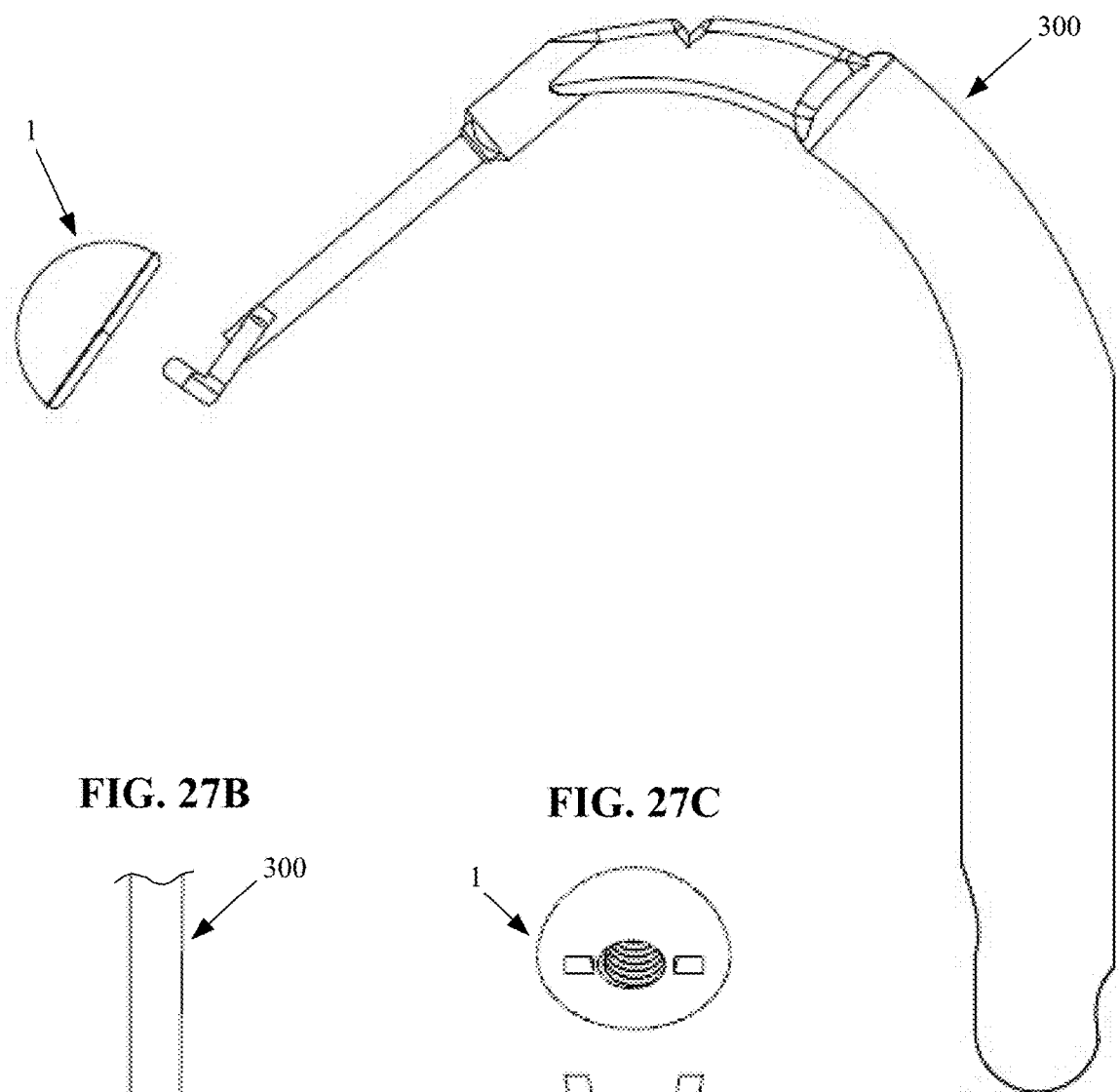

FIG. 27A is a side view of the head component insertion device of FIG. 24A, shown just prior to the head component of FIG. 4A being releasably coupled thereto.

Figure 27B:
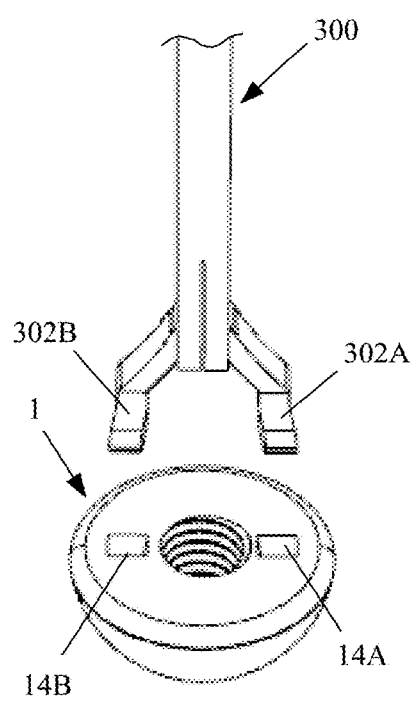

FIG. 27B is an exploded front of the head component insertion device and the head component, shown prior to the head component being releasably coupled to the device.

Figure 27C:
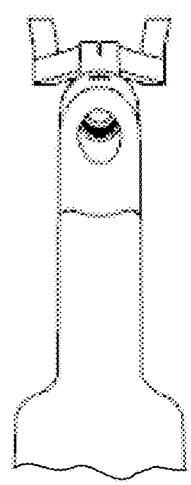

FIG. 27C is an exploded rear view of the head component insertion device and the head component, shown prior to the head component being releasably coupled to the device, and with the device being shown without the actuation member.

Figure 28A:
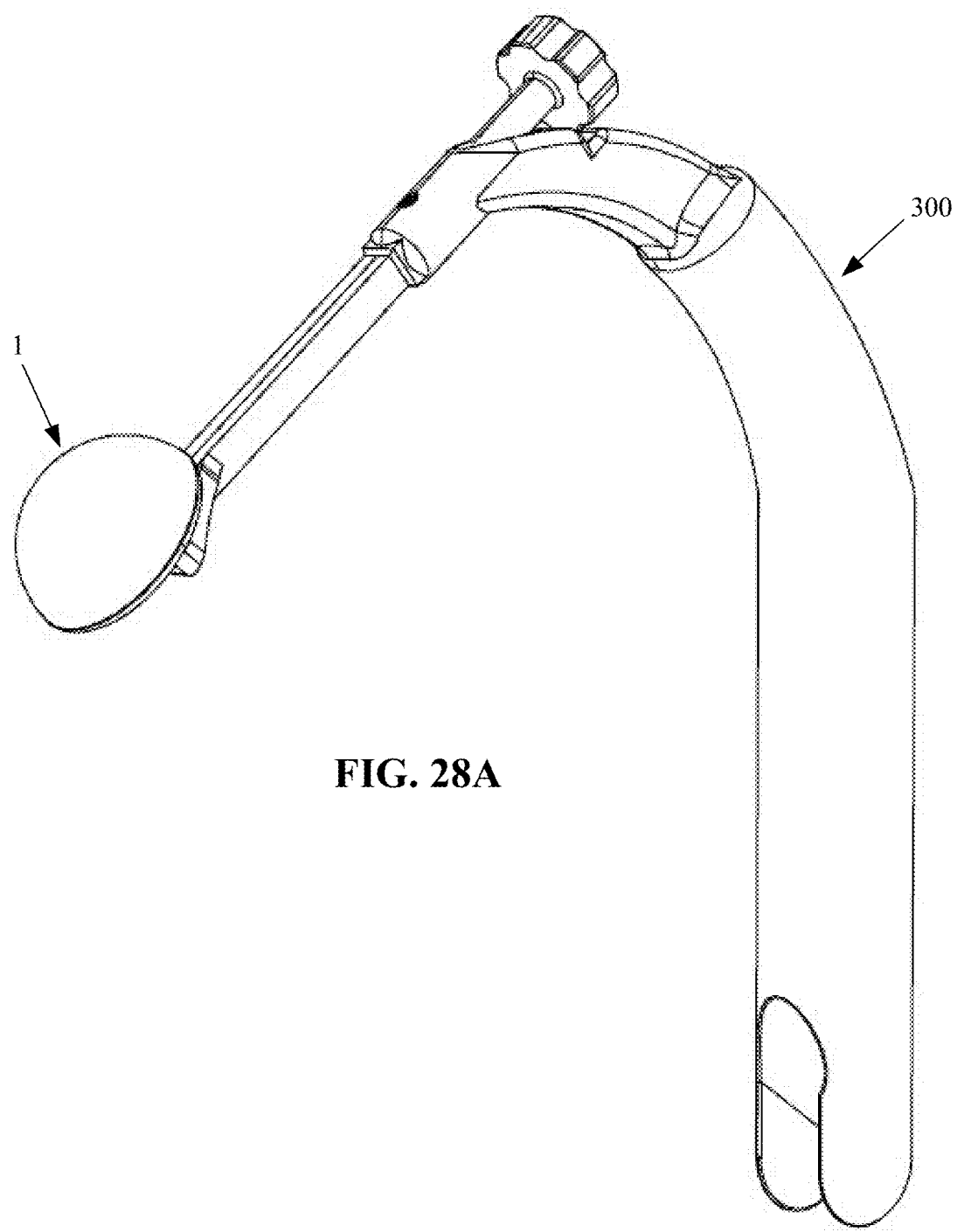

FIG. 28A is the perspective view of the head component insertion device of FIG. 24A, but shown just after the head component of FIG. 4A has been releasably coupled thereto.

FIG. 28B is a side view of the arrangement of FIG. 28A

FIG. 28C is a front view of the arrangement of FIG. 28A.

FIG. 28D is a top view of the arrangement of FIG. 28A.

FIG. 28E is a rear view of the head component insertion device, shown without the head component, and being shown with the prongs in a static position before the head component is secured thereto using the actuation member.

FIG. 28F is the rear view of FIG. 28E, but is shown after the prongs have been separated by insertion and rotation of the actuation member.

FIG. 29A is a first perspective view of the metaphyseal component insertion device of FIG. 12Jii, usable for placement of the metaphyseal component.

FIG. 29B is a front view of the metaphyseal component insertion device of FIG. 29A.

FIG. 29C is a top view of the metaphyseal component insertion device of FIG. 29A.

FIG. 29D is a bottom view of the metaphyseal component insertion device of FIG. 29A.

FIG. 29E is an end view of the metaphyseal component insertion device of FIG. 29A.

Figure 29F:
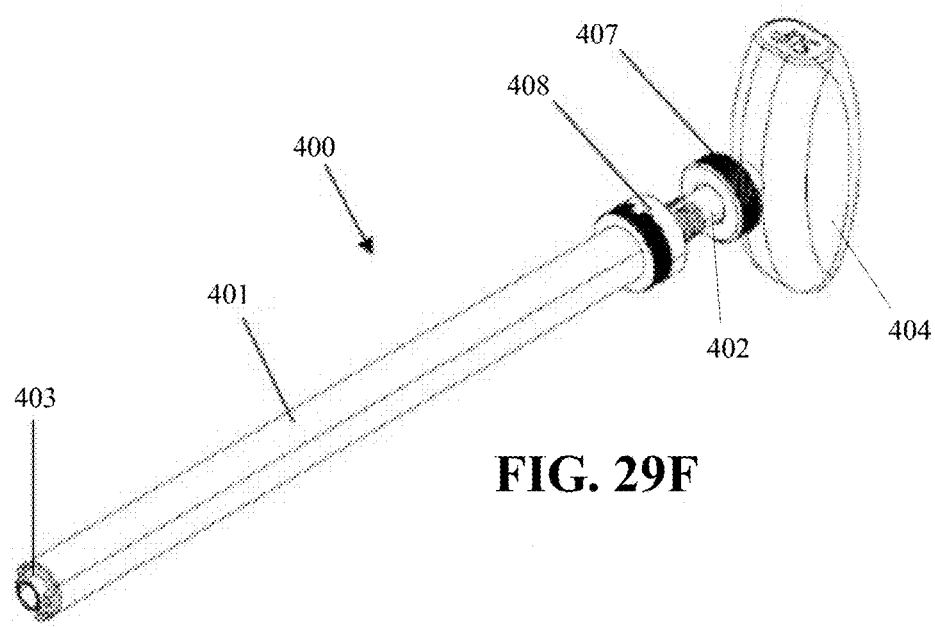

FIG. 29F is a second perspective view of the metaphyseal component insertion device of FIG. 29A.

Figure 29G:
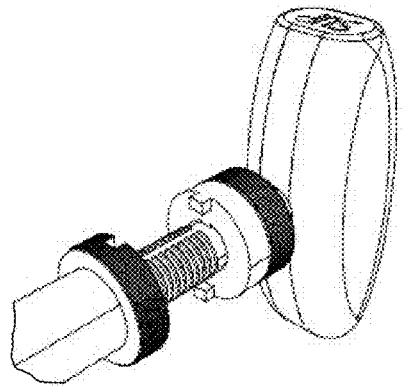

FIG. 29G is the second perspective view of FIG. 29F but shown enlarged, and shown with the flanged washer and the jam nut backed away from the end of the outer tubular body.

Figure 29H:
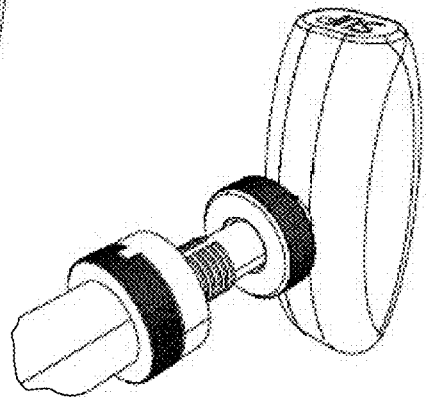

FIG. 29H is the enlarged perspective view of FIG. 29G, but shown after the flanged washer has been moved into engagement with the end of the outer tubular body.

Figure 29I:
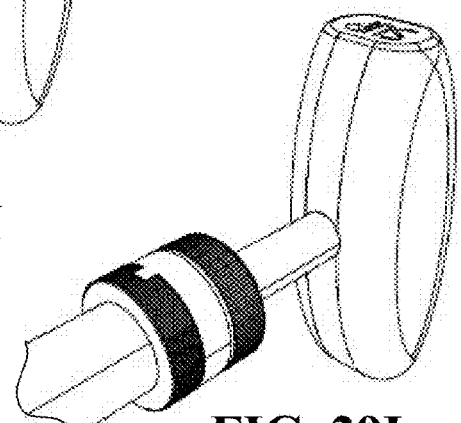

FIG. 29I is the enlarged perspective view of FIG. 29H, but shown after the jam nut has been threaded onto the inner tubular body and into contact with the flanged washer, to prevent relative rotation between outer tubular body and the inner tubular body.

Figure 29J:
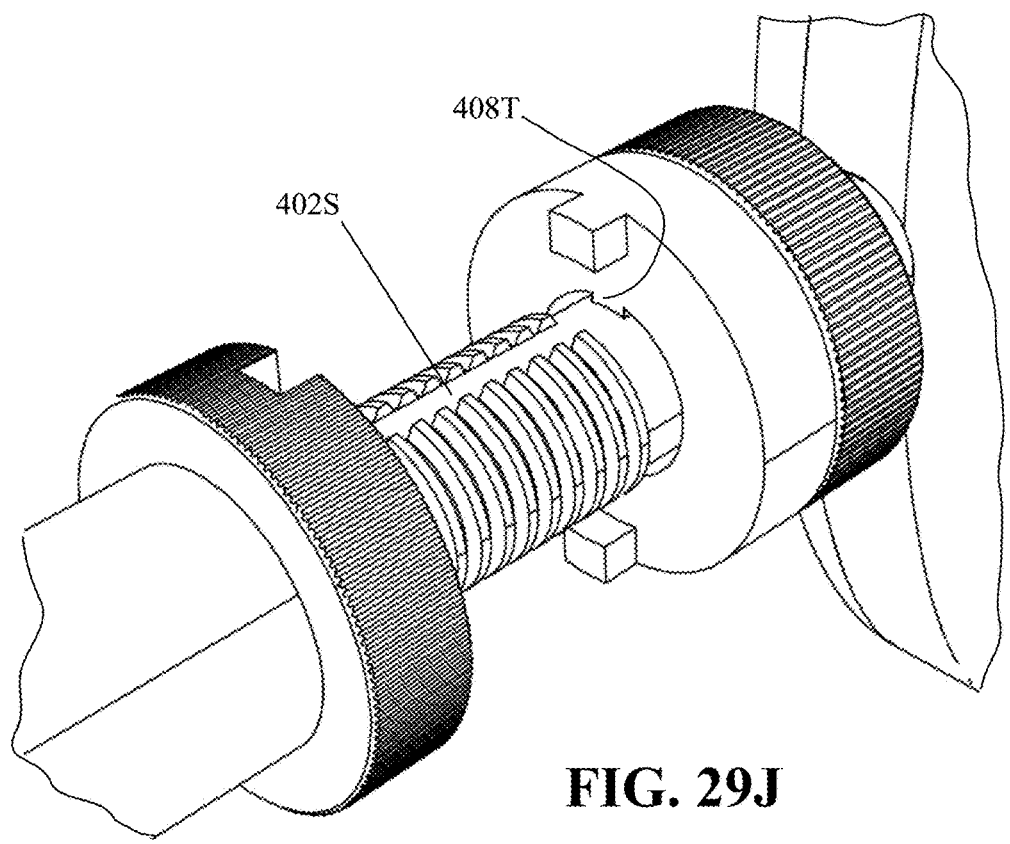

FIG. 29J is the view of FIG. 29G shown enlarged even further.

Figure 29K:
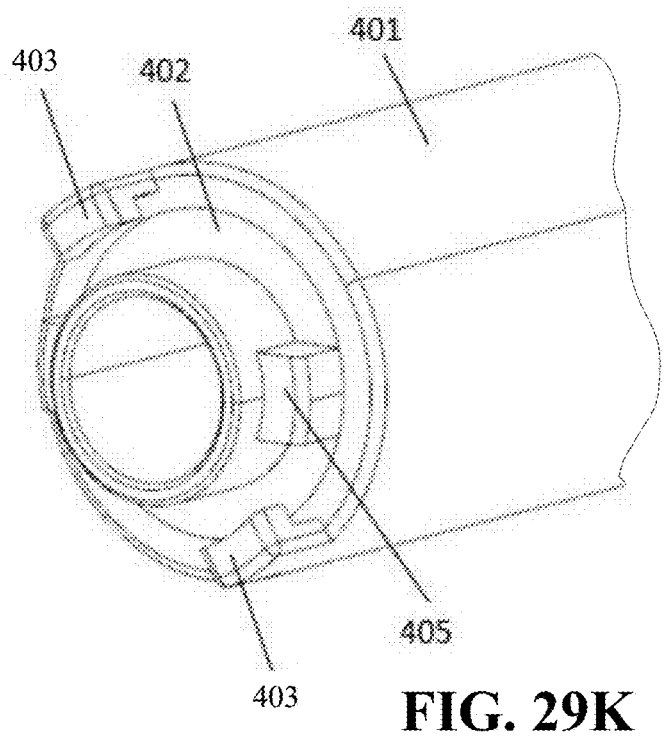

FIG. 29K is an enlarged detail view of one end of the metaphyseal component insertion device of FIG. 29F.

FIG. 30 is an exploded view of the component parts of the metaphyseal component insertion device of FIG. 29A.

FIG. 31A is a top view of the outer tubular body of the metaphyseal component insertion device of FIG. 29A.

FIG. 31B is a side view of the outer tubular body of FIG. 31A.

FIG. 31C is a first end view of the outer tubular body of FIG. 31A.

FIG. 31D is a second end view of the outer tubular body of FIG. 31A.

FIG. 31E is an enlarged perspective view of the bayonet mount on one end of the outer tubular body of FIG. 31A.

FIG. 31F is an enlarged side view of the bayonet mount on one end of the outer tubular body of FIG. 31A.

Figure 32A:
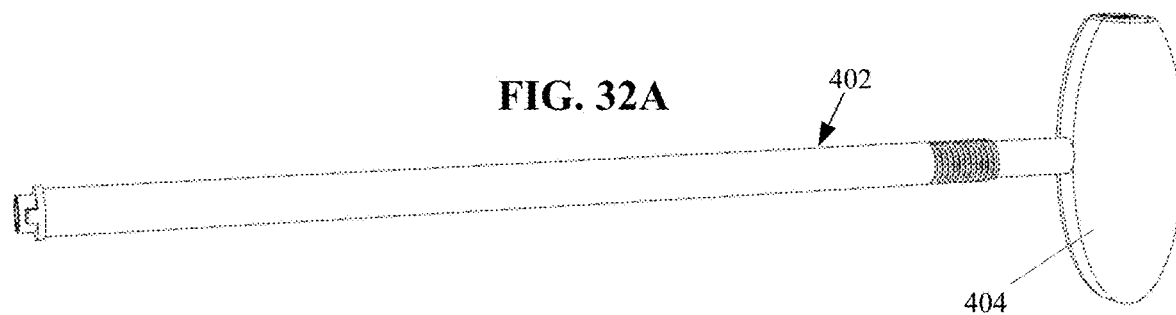

FIG. 32A is a perspective view of the inner tubular body of the metaphyseal component insertion device of FIG. 29A.

Figure 32B:
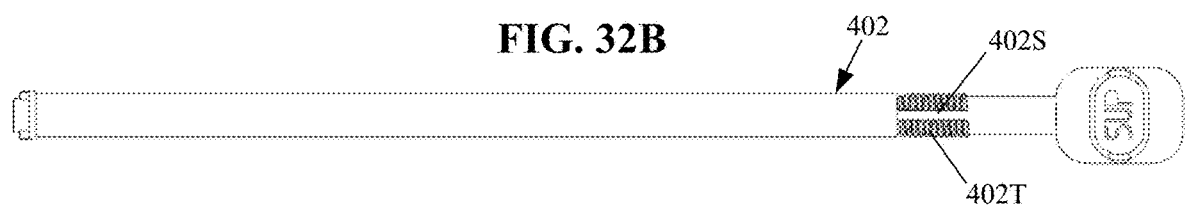

FIG. 32B is a top view of the inner tubular body of FIG. 32A.

Figure 32C:
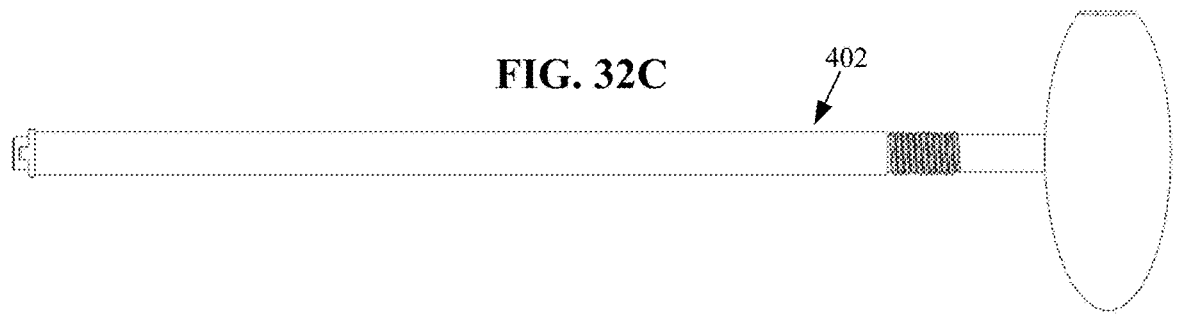

FIG. 32C is a side view of the inner tubular body of FIG. 32A.

Figure 32D:
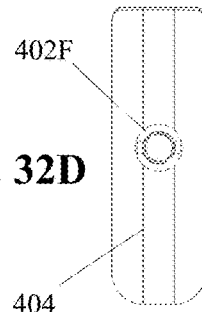

FIG. 32D is an end view of the inner tubular body of FIG. 32A.

FIG. 32E is the perspective view of FIG. 32A, but also shows the hidden features using dash lines.

FIG. 32F is the top view of FIG. 32B, but also shows the hidden features using dash lines.

FIG. 32G is the side view of FIG. 32C, but also shows the hidden features using dash lines.

FIG. 33A is a perspective view of the flanged washer of the metaphyseal component insertion device of FIG. 29A.

FIG. 33B is a front view of the flanged washer of FIG. 33A.

FIG. 33C is a side view of the flanged washer of FIG. 33A.

FIG. 33D is a top view of the flanged washer of FIG. 33A.

FIG. 34A is a perspective view of the jam nut of the metaphyseal component insertion device of FIG. 29A.

FIG. 34B is a side view of the jam nut of FIG. 34A.

FIG. 34C is a front view of the jam nut of FIG. 34A.

FIG. 35A is a perspective view of the sleeve of the metaphyseal component insertion device of FIG. 29A.

FIG. 35B is an end view of the sleeve of FIG. 35A.

FIG. 35C is a side view of the sleeve of FIG. 35A.

Figure 36A:
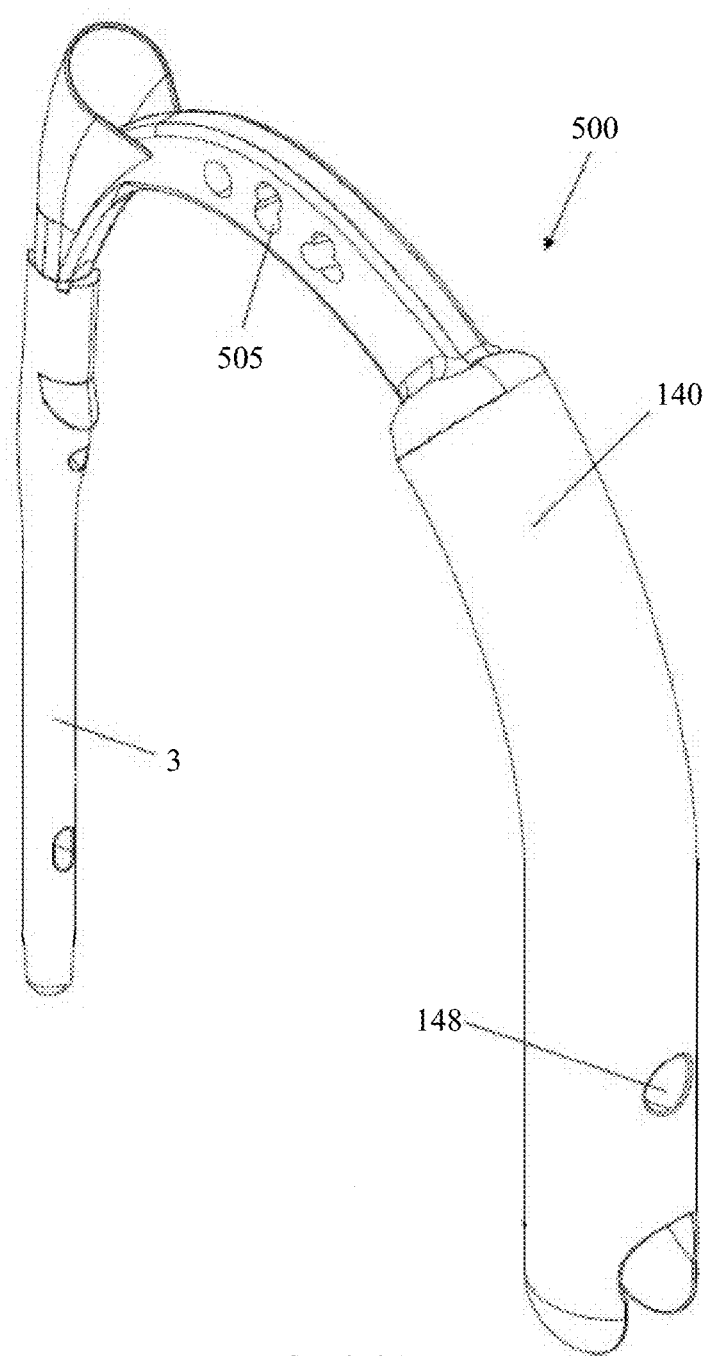

FIG. 36A is a perspective view of the diaphyseal insertion device.

FIG. 36B is a front view of the diaphyseal nail insertion device of FIG. 36A.

FIG. 36C is a top view of the diaphyseal nail insertion device of FIG. 36A.

FIG. 36D is the front view of FIG. 36B, but with the hidden features shown using dash lines.

FIG. 36E is a rear view of the diaphyseal nail insertion device of FIG. 36A.

FIG. 36F is a top view of the diaphyseal nail insertion device of FIG. 36A.

Figure 37:
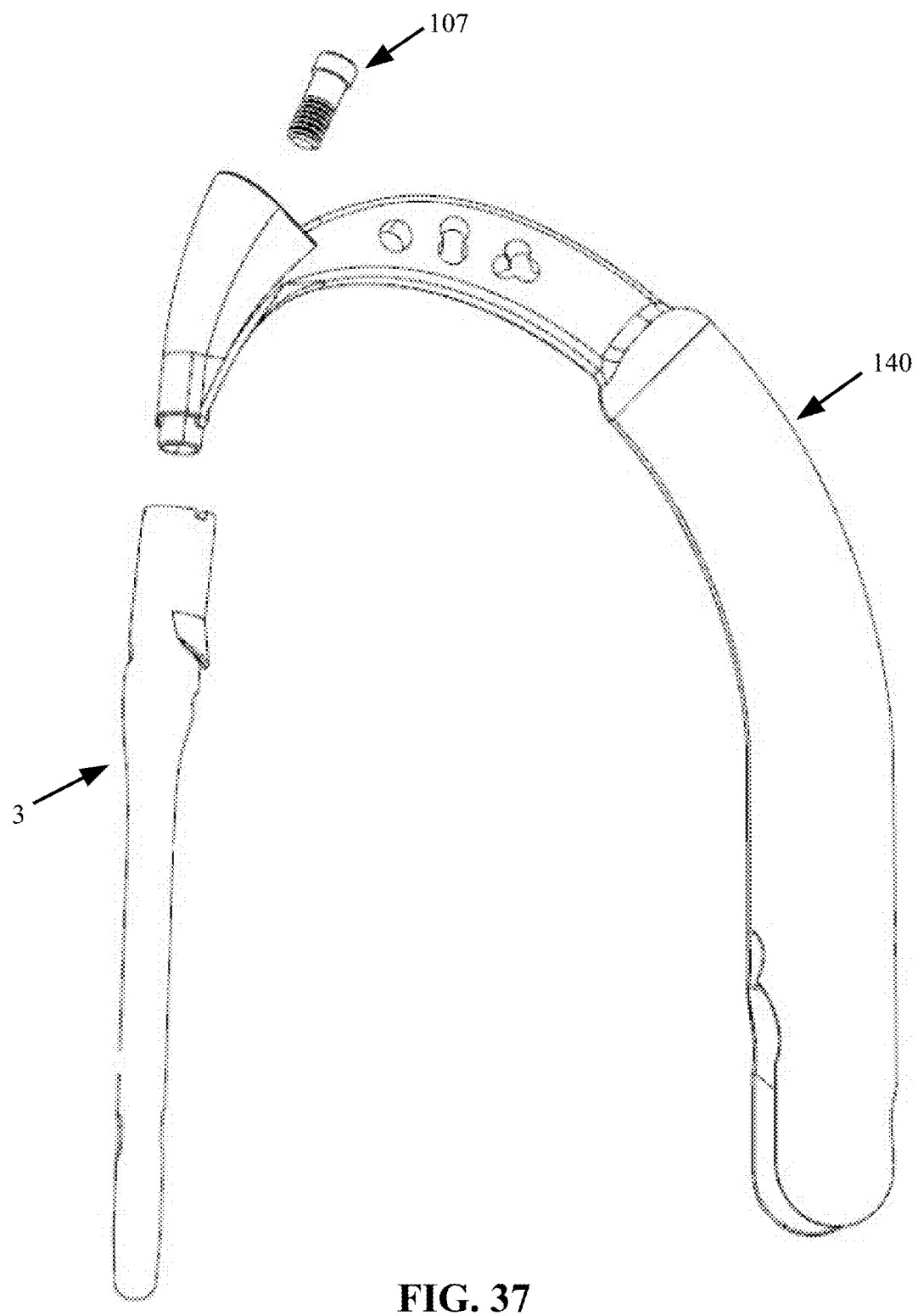

FIG. 37 is an exploded view of the component parts of the diaphyseal nail insertion device of FIG. 36A.

Figure 7A:
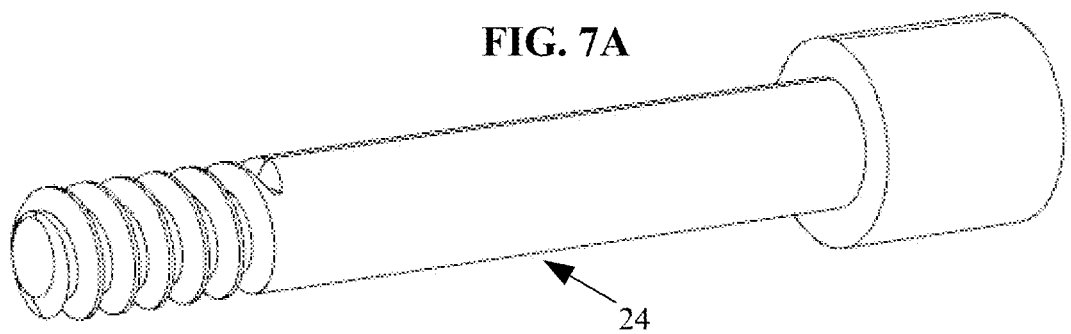
FIG. 7A is a perspective view of the locking device of the prosthesis of FIG. 2.

FIG. 38A is a perspective view of a torqueing device used to install the locking device of FIG. 7A.

FIG. 38B is a front view of the torqueing device of FIG. 38A.

FIG. 38C is a top view of the torqueing device of FIG. 38A.

FIG. 38D is an end view of the torqueing device of FIG. 38A.

DETAILED DESCRIPTION OF THE INVENTION

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, the reference throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Additionally, the described features, advantages, and characteristics of any particular embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations.

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/fittolerences%20%5BRead-Only%5D.pdf.

Throughout this disclosure, any use of the adjectives "superior" and "inferior" are used in a non-limiting manner. In particular, use of the term "superior" is intended to refer to the area of the element that, at the specific moment of its use, is closer to the patient's head, and use of the term "lower" is intended to refer to the furthest part of the patient's head.

Next, an embodiment of the invention will be described briefly as a non-limiting illustrative example. It will be described with respect to a hip prosthesis, although as indicated, it is also applicable with respect to a shoulder prosthesis.

The prosthesis 99 disclosed herein is made up of three independent bodies, which in the embodiment shown in the figures correspond to:

- A head component 1 with the general shape of a hemisphere. It may be bipolar or unipolar.
- A metaphyseal component 2, for supporting the head component 1, to which it is connected inside the patient's body. The metaphyseal component 2 is produced in different lengths to control the femoral offset.
- A diaphyseal nail 3, which passes through an aperture 21 of the metaphyseal component 2 in order to be fastened in the appropriate position. The diaphyseal nail 3 is produced with different diameters and lengths.

FIG. 1 is a front view of the prosthesis 99, shown after being placed in the hip of a patient, while FIG. 2 is a cross-sectional view taken through the entire prosthesis, and FIG. 2A is a second cross-sectional view, taken through the head component and a portion of the metaphyseal component of the prosthesis, being taken at 90 degrees to the cross-section of FIG. 2. FIG. 3 is front view illustrating a portion of the procedure for placement of the head component 1 of the prosthesis 99 using a placement instrument 300 that is particularly configured to co-act with the head component.

Figure 4F:
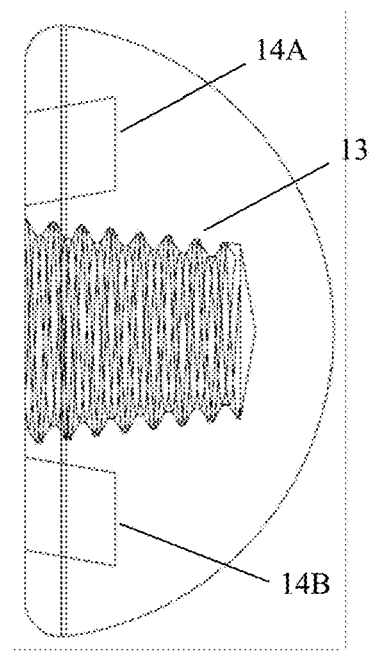
FIG. 4F is a cross-sectional view through the head component of the prosthetic device of FIG. 2.

In FIGS. 4A-4F the head component 1 is shown in detail, and which has a front face 11 that may be formed to be substantially half of a sphere, although it may alternatively be formed to be somewhat more than half of a sphere or somewhat less than a half sphere (i.e., a "spherical cap"). The head component 1 also has a rear face 12 that may be used for fastening to the metaphyseal component 2, and therefore includes a bore 13, which in the example shown is threaded. The threading is conical in one embodiment. The rear face 12 of the head component 1 has a pair of particularly shaped recesses 14A and 14B that are configured to receive correspondingly shaped protrusions of a first instrument, which is the head component insertion device 300 shown in FIG. 3 and FIG. 24A. The particularly shaped recesses 14A and 14B may each have a different cross-sectional shape (i.e., a different profile) in one embodiment, and in another embodiment, as shown in FIG. 2A and FIG. 4F, the recesses may be a mirrored copy of each other. Although the profile of the recesses 14A/14B are shown in the figures as being trapezoidal, other possible profile shapes may alternatively be used, including, but not limited to, a rectangular shape, and a parallelogram (close to being rhombus, having 4 congruent sides). Also, although the recesses may preferably be spaced as far apart as possible on the rear face 12 of the head 1, which would position them on opposing sides of the bore 13 as shown throughout the figures, the recesses may alternatively be positioned closer together, being on only one side of the bore. Note that the head component 1 will be produced in different sizes so that the surgeon may select the one most suitable for a particular patient. It is further noted that these structural aspects relating to the recesses 14A/14B may also be used on a bipolar head component, in addition to the unipolar head component described herein.

Figure 7B:
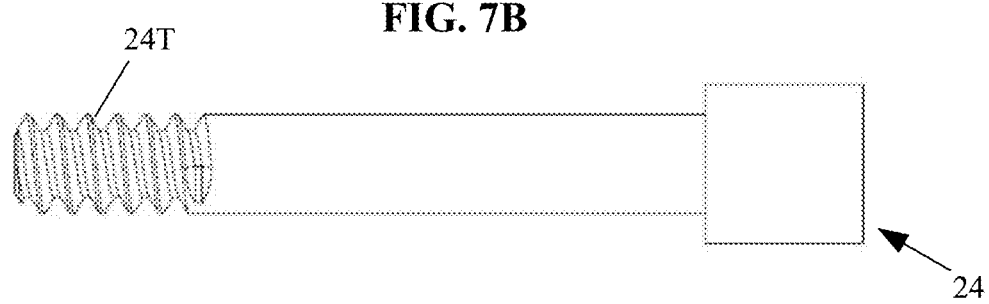
FIG. 7B is a side view of the locking device of the prosthesis of FIG. 2.
Figure 8:
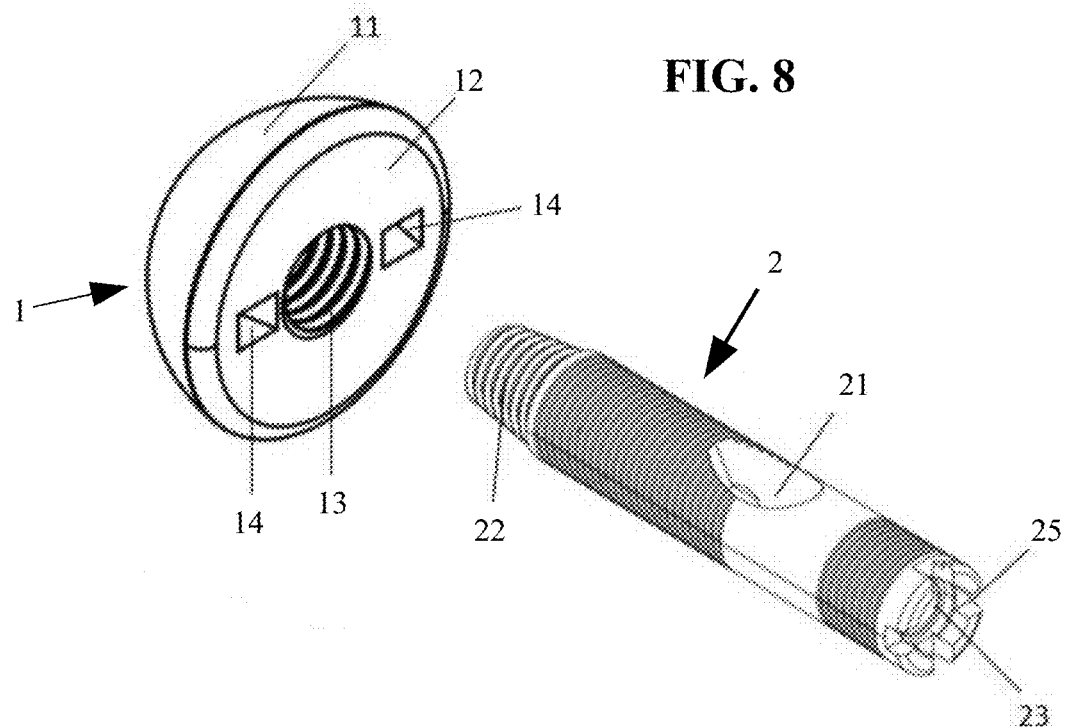
FIG. 8 is an exploded view of the metaphyseal component and the head component of the prosthetic device of FIG. 2.
Figure 9:
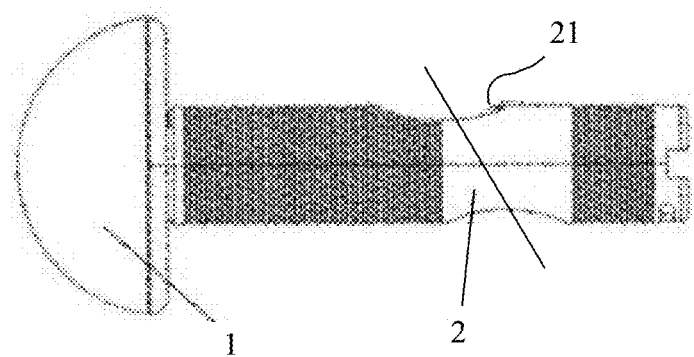
FIG. 9 is a side view of the metaphyseal component and the head component of FIG. 8, shown after being coupled together.

The metaphyseal component 2 is shown in detail in FIGS. 5A to 5H, and may be a substantially straight component, and may furthermore have generally cylindrical shape. The metaphyseal component 2 is connected to the head component 1 by means of a shank portion 22 at the first end of the metaphyseal component, which shank portion may be threaded for securement to the bore 13 when the bore is threaded. Thus, the shank portion itself may be conical and have conical external threading when the bore 13 of the head component has conical threading. The metaphyseal component 2 also has a transverse aperture 21 that may be centrally positioned in the main body portion 26 of be metaphyseal component, through which the diaphyseal nail 3 is inserted, and which nail is ultimately positioned inside the femoral canal. The metaphyseal component 2 also includes a longitudinal hole 23 with an opening formed on the second end (see FIG. 5F), into which a locking device 24 is inserted (see FIG. 10 and FIG. 11), to rigidly connect the metaphyseal component the diaphyseal nail 3. As shown in FIGS. 7A and 7B, the locking device 24 will usually be a threaded screw, the tip of which passes totally or partly through the diaphyseal nail 3. In the embodiments shown, the locking device 24 passes totally the diaphyseal nail and reaches the first section of the metaphyseal component. In one embodiment the metaphyseal component 2 may have grooving over a portion or over its entire surface to improve support in the femur. Other types of finish are also possible.

The diaphyseal nail 3 is shown in detail in FIGS. 6A to 6F. The diaphyseal nail 3 has a first portion 31 with an increasing cross section that is configured for insertion in the femoral canal, and which first portion includes one or more fastening apertures 32 configured to receive one or more screws 31S (see FIG. 10 and FIG. 12W) for fastening that portion of the diaphyseal nail 3 to the femur. The second portion 33 of the diaphyseal nail 3 is configured to be engaged within the transverse aperture 21 of the metaphyseal component 2, the upper part 33U of which projects beyond the metaphyseal component 2. The second portion 33 of the diaphyseal nail 3 may have a transverse hole 36 configured to be utilized with respect to the locking device 24, as discussed hereinafter.

Figure 10:
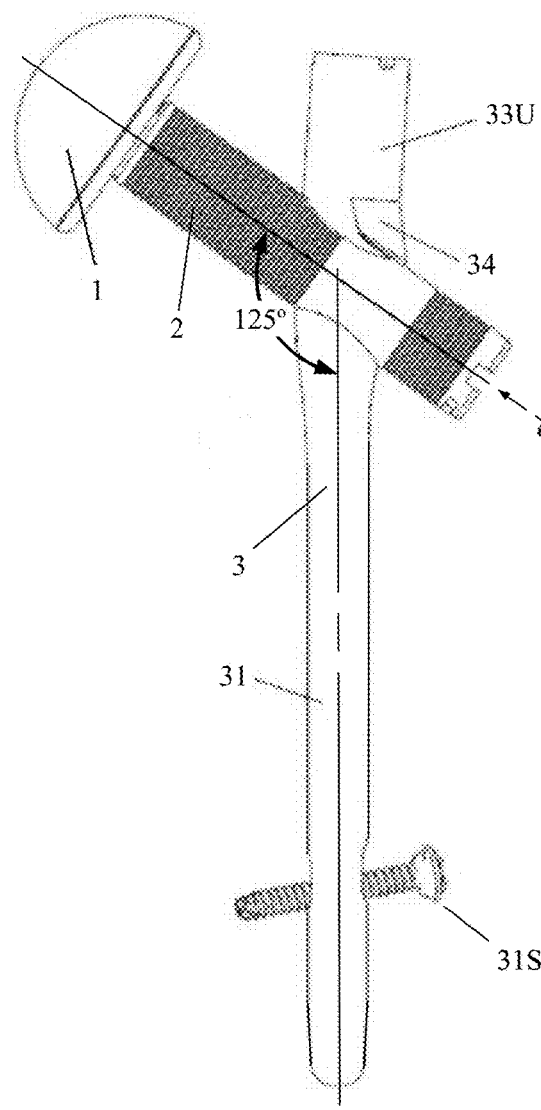
FIG. 10 is a side view that shows the diaphyseal nail mounted to the assembled metaphyseal component and head component of FIG. 9, and with the locking device shown prior to being coupled thereto.
Figure 11:
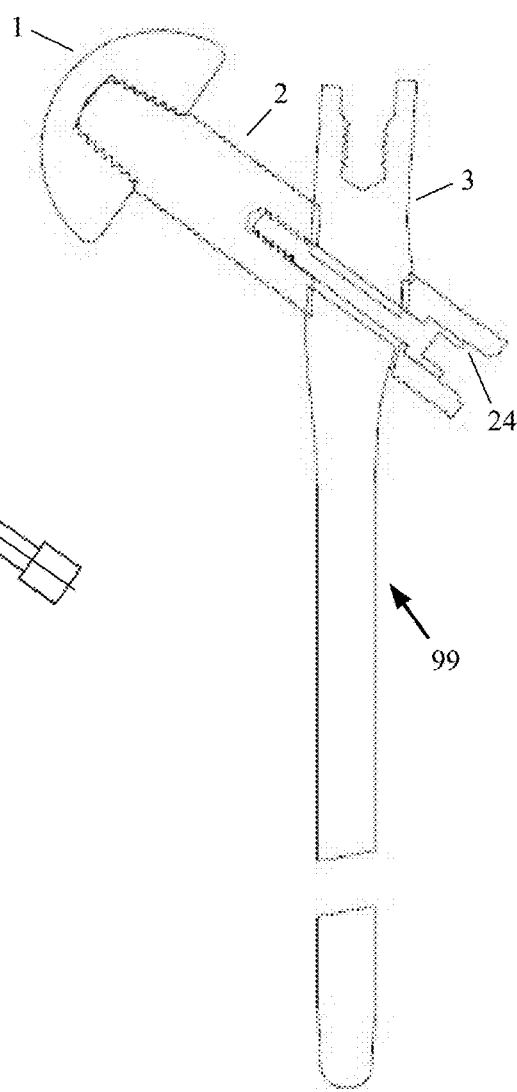
FIG. 11 is the cross-sectional view of FIG. 2, shown side-by-side with the side view of FIG. 10.

As shown in FIG. 10, the diaphyseal nail 3, after being inserted into the transverse aperture 21 of the metaphyseal component 2, is ready to be secured thereto using any means presently known in the art or which may be later developed, and which may include, but is not limited to, the locking device 24. The locking device 24 may be inserted into the opening, at the second end of the metaphyseal component (FIG. 5F) and be received in a first portion of its longitudinal hole 23, and pass through the transverse hole 36 of the diaphyseal nail 3, and then be received in a second portion of the longitudinal hole 23. The locking device 24 may be secured within the transverse hole 23 in any suitable manner, including but not limited to, threaded engagement therebetween. Any portion of the locking device 24 and corresponding portion of the diaphyseal nail 3 (and the metaphyseal component 2) may be threaded. Merely to be exemplary, in the figures, the distal end of the locking device 24 is illustrated to include external threads 24T (see FIG. 7B) and the distal end of the transverse hole 23 has internal threading 23T (see FIG. 5H).

Figure 6A:
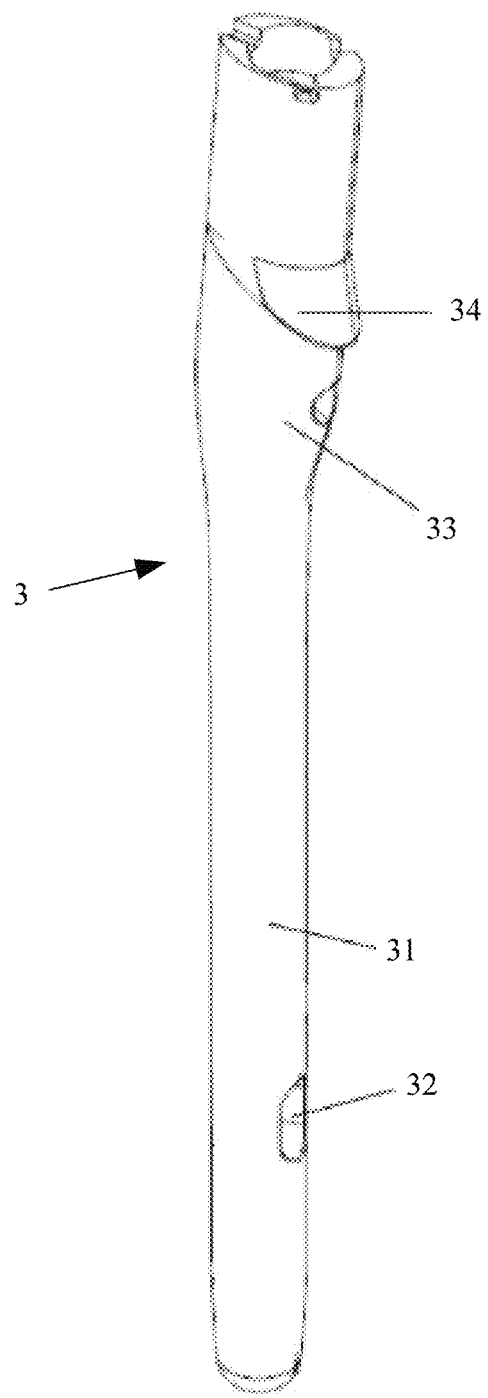
FIG. 6A is a perspective view of the diaphyseal nail of the prosthetic device of FIG. 2.
Figures 6B, 6C, 6D, 6E:
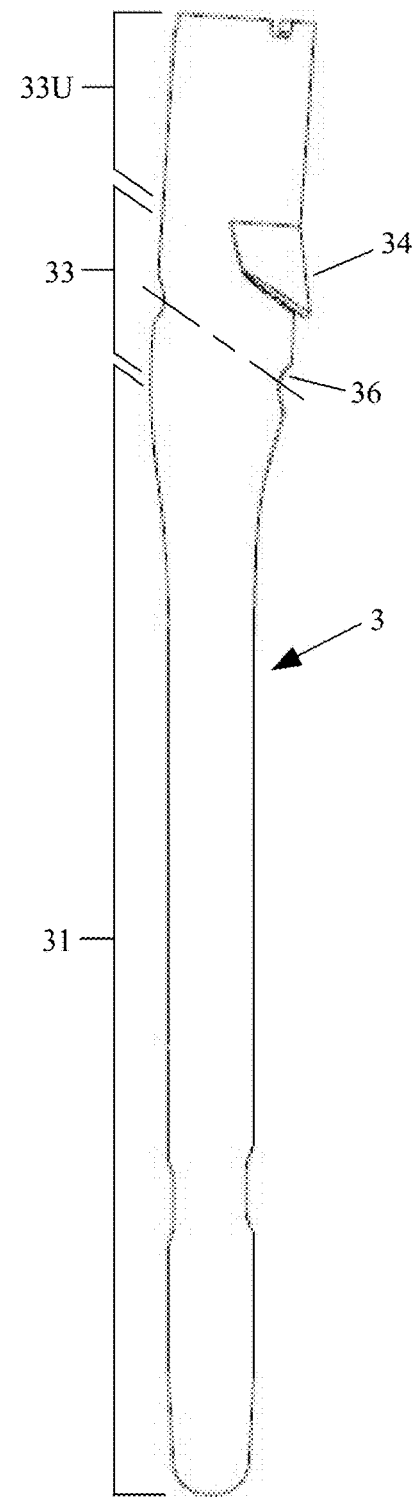
FIG. 6B is a side view of the diaphyseal nail of the prosthetic device of FIG. 2.
FIG. 6C is a front view of the diaphyseal nail of the prosthetic device of FIG. 2.
FIG. 6D is a rear view of the diaphyseal nail of the prosthetic device of FIG. 2.
FIG. 6E is a top view of the diaphyseal nail of the prosthetic device of FIG. 2.
Figure 6F:
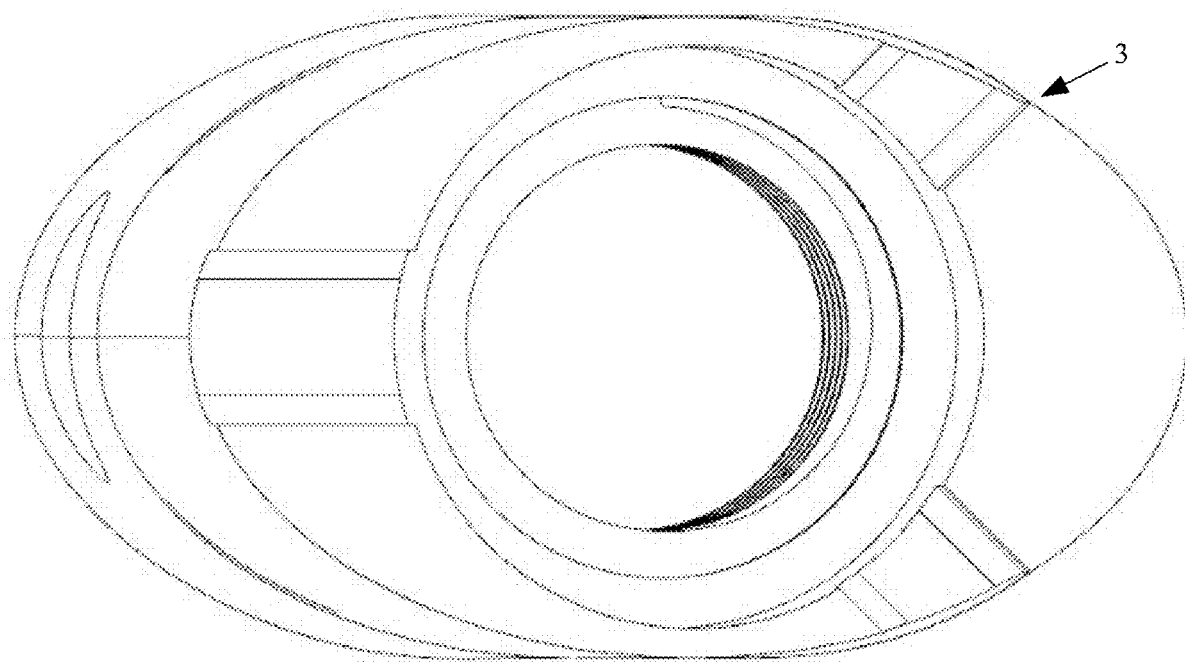
FIG. 6F is the top view of FIG. 6E shown enlarged.

In FIG. 6A and FIG. 6B the diaphyseal nail 3 is shown with a protrusion 34, which is ultimately positioned at the edge of the transverse aperture 21 of the metaphyseal component 2, which forms a stop when the diaphyseal nail 3 is inserted into the transverse aperture 21 of the metaphyseal component 2, and which helps transmit the moments created with the movement of the joint and the load created by walking, and when the patient rests on the operated limb.

The angle which is formed between the metaphyseal component 2 and the diaphyseal nail 3 (cervico-diaphyseal angle) will be approximately 125° (but may be larger or smaller, for example between 115° and 135°).

Next, the surgical procedure is described, including a preferred method of positioning the hip prosthesis and the necessary instruments. These instruments are particularly configured for properly positioning the elements of the herein disclosed prosthesis.

Figure 12A:
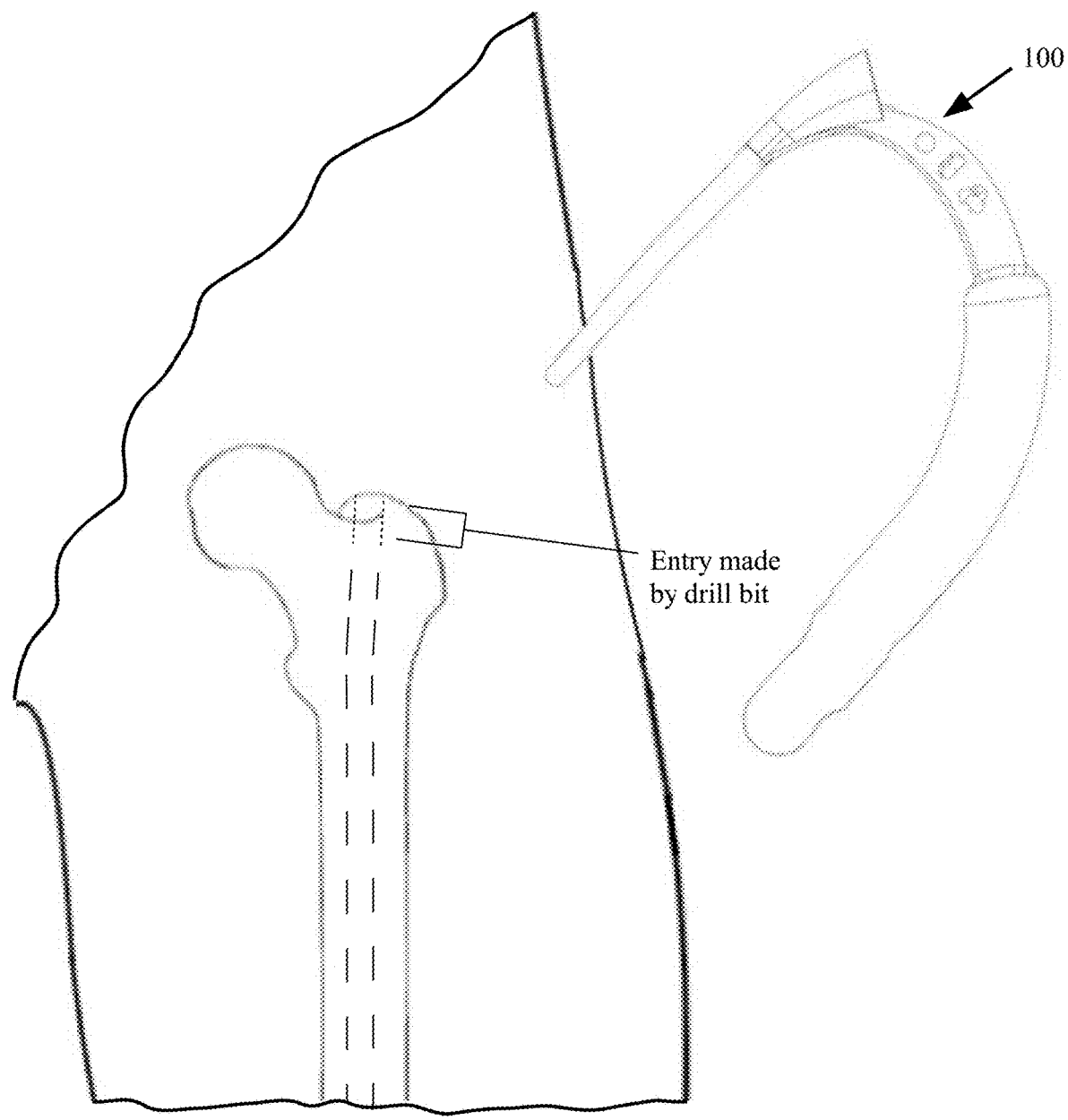
FIG. 12Ai is a front view illustrating the Kirschner wire centering device, just prior to the centering nail being inserted into the femoral canal of the patient; and showing the entry made into the femur.
Figure 12B:
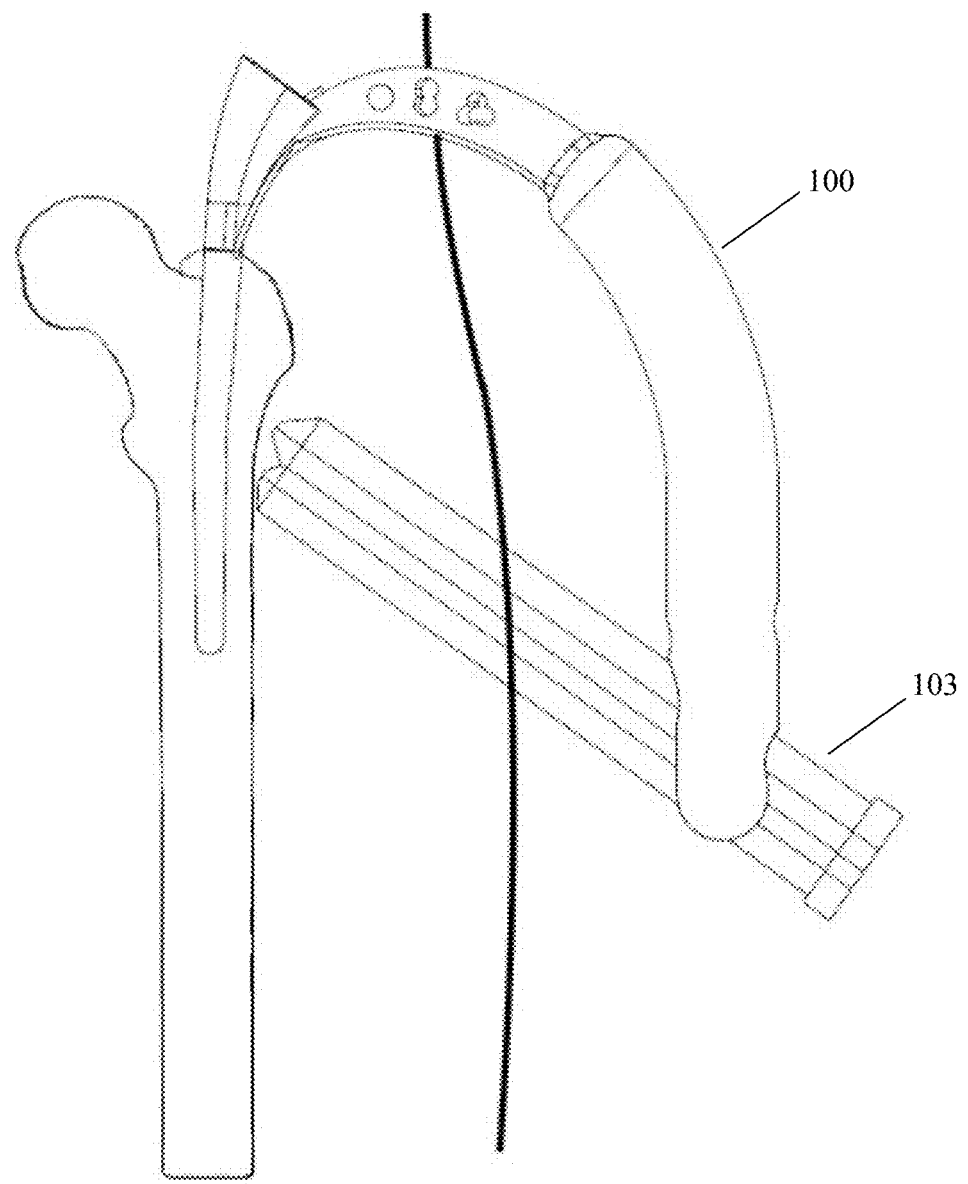
FIG. 12B is the front view of FIG. 12Aiii, but shown after the centering sleeve has been inserted into a particularly shaped opening in the handle.

The surgical procedure is illustrated in FIGS. 12Ai-12S, and the steps of the overall surgical procedure may be summarized as follows:

1. Two or three incisions are made—an Upper Incision, Middle Incision, and sometimes a Lower Incision;
2. The tip of the greater trochanter of the femur is drilled (FIG. 12Ai);
3. The Centering Nail is introduced using the handle guide through the upper incision, through the drilled opening in the greater trochanter, into the femoral canal (FIGS. 12Ai-12Aii);
4. The Kirschner wire centering sleeve is slidably introduced through the middle incision, guided by an opening in the handle-guide (FIGS. 12Aiii-12B);
5. A Kirschner wire is introduced in the center of the neck and femoral head, being guided/slid through a passageway in the sleeve (FIG. 12Ci);
6. The sleeve is removed (FIG. 12D);
7. The Centering Nail is removed, leaving the Kirschner wire in place (FIG. 12Ei);
8. An opening in the lateral cortical bone is drilled, being guided by the Kirschner wire;
9. The Cannulated extractor (FIGS. 18A-18P) is introduced through the middle incision, being guided by the Kirschner wire (FIG. 12F);
10. The tip of the Cannulated extractor is introduced into the drilled opening in the femoral head (FIG. 12G);
11. The Claws of the cannulated extractor are extended inside the femoral head in order to increase the grip on the femoral head, and the cannulated extractor is rotated so that rotations of the femoral head inside the acetabulum get the femoral head detached from the ligamentum teres (FIG. 12H);
12. The upper part of the articular capsule is opened, using, for example, a scalpel that is introduced through the upper incision;
13. Adduction of the affected limb is performed in order to dislocate the femoral head from the acetabulum socket (FIGS. 12Hi-12Hii).
14. The Cannulated Extractor and the Kirschner wire are removed.
15. The femoral head is extracted through the upper incision using, for example, Kocher forceps (not shown) (FIGS. 12iii-12Hiv);
16. The Head Component (FIGS. 4A-4F) is mounted to the Head Component Insertion Device (FIG. 24A) and the Head Component is introduced through the upper incision into its proper position (FIG. 12I);
17. Metaphyseal Component (FIGS. 5A-5H) is bayonet-mounted to the Metaphyseal Component Insertion Device (FIG. 29A) and is then introduced through the middle incision (FIG. 12Ji), with the Metaphyseal Component Insertion Device cooperating with the opening in the handle guide of the Head Component Insertion Device and is thereby guided.
18. The distal end of the Metaphyseal Component is threaded into the bore of the Head Component using the Metaphyseal Component Insertion Device (FIG. 12K);
19. The sleeve of the Metaphyseal component is withdrawn away from the Handle Guide of the Head Component insertion Device (compare FIGS. 12K and 12L), permitting the Handle Guide to slide relative to the Metaphyseal Component Insertion Device, for removal of the Head Component Insertion Device (FIG. 12L).

20. The Diaphyseal Nail is releasably coupled to the Handle Guide, which is used to introduce the tip of the nail through the upper incision, in through the tip of the greater trochanter of the femur and through the transverse aperture of the Metaphyseal component, and place the body of the nail placed in the femoral canal (FIGS. 12M-12N).
21. The Locking Device is releasably coupled to the Locking Device Screw Driver (FIG. 12P), which is used to introduce the Locking Device through an axial passageway in the Metaphyseal Component Insertion Device, for insertion through the first portion of the longitudinal hole of the Metaphyseal Component, through the aligned opening of the Diaphyseal Nail, to be rotated and secured with respect to at least the second portion of the longitudinal hole of the Metaphyseal Component (FIGS. 12Q-12R);
22. The Locking Device Screw Driver and Metaphyseal Component Insertion Device is removed (FIG. 12S);
23. Screw sleeve is slidably coupled to the Handle Guide and the axial opening therein is used to drill a hole in the femur that is aligned with the hole in the Diaphyseal Nail (FIG. 12T);
24. The Screw Sleeve is used to install a screw fasten the diaphyseal nail to the femur. (FIG. 12U);
25. The Sleeve is slidably removed from the Handle Guide (FIG. 12V); and
26. The Handle Guide is detached from the Diaphyseal Nail, and removed out of the upper incision—the prosthesis is assembled and in its final position (FIG. 12W).

The prosthesis positioning method requires two or three incisions (see FIG. 12Cii):
an upper incision (UI) slightly proximal to the greater trochanter of the femur;
a middle incision (MI) which will be determined by the site through which the Kirschner wires enter in accordance with the Kirschner Wire centering device;
an optional lower incision (not shown) which will be determined by the positioning of the distal screw(s). The lower incision may not be necessary as placement of the distal screw(s) may be made through the middle incision (MI).

The first overall step in the prosthesis placement procedure is the removal of the femoral head. This is carried out using a cannulated femoral or humeral head extractor 200 (see FIGS. 12F-12H), which is inserted in the middle incision (MI). However, in order for the cannulated femoral head extractor 200 to effectively remove the femoral head, it must penetrate in the most perpendicular and centered manner possible into the cancellous bone of the femoral head.

Accordingly, as seen in FIGS. 12Ai-12Ei, a first Kirschner wire 102 is installed and used as a guide for the cannulated head extractor 200, with the first Kirschner wire being inserted through the middle incision (MI). A second Kirschner wire 102' may also be applied through the middle incision (see FIG. 12Cii).

For the Kirschner wire 102 to adequately serve as a guide for the cannulated femoral head extractor 200, it must be centered in the diaphysis, neck, and head of the femur. Therefore the Kirschner wires 102, 102' are placed in the correct position by means of a Kirschner wire centering device 100.

Figure 14A:
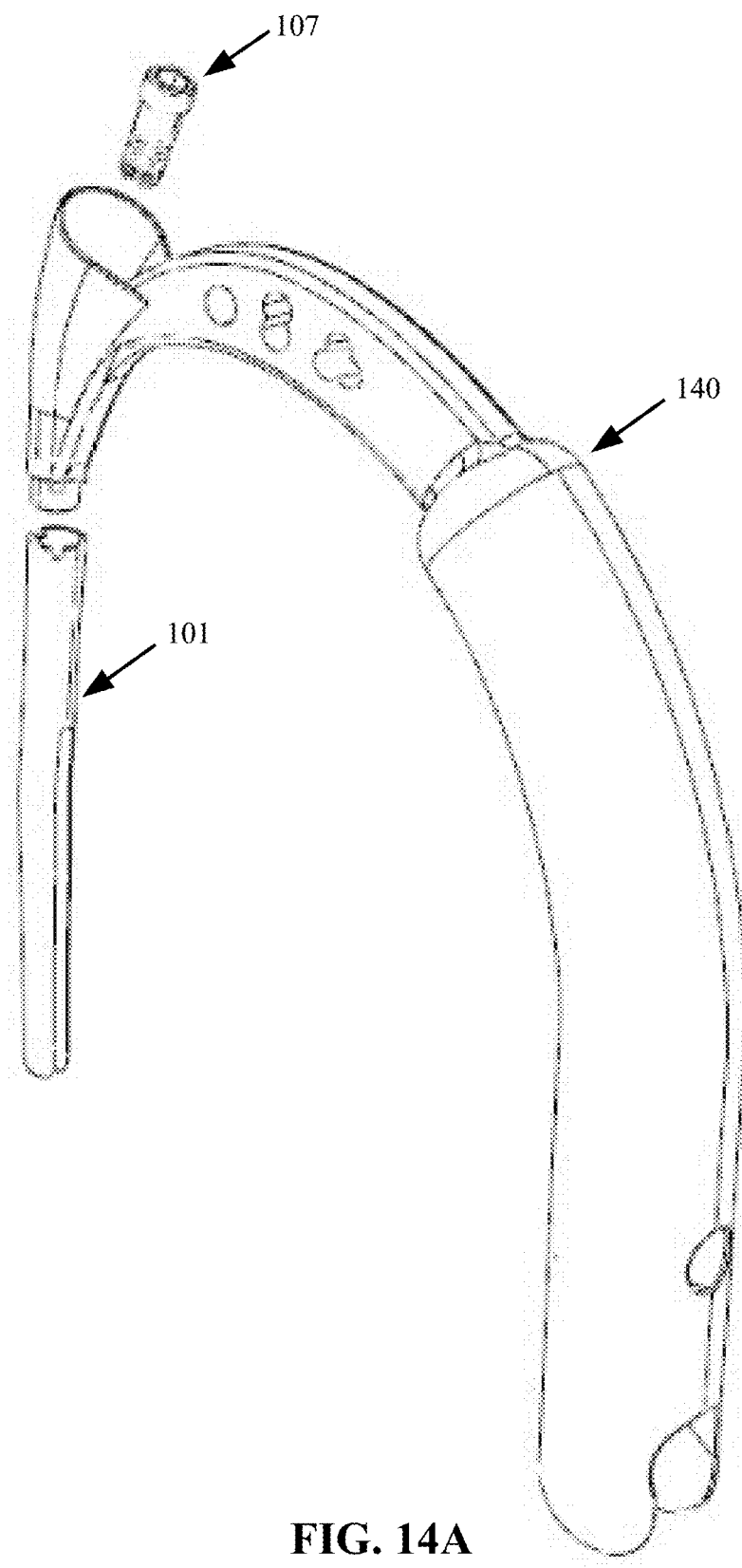
FIG. 14A is an exploded perspective view showing the prosthesis placement apparatus of FIG. 13A just prior to coupling thereto of a centering nail, for use in placing a Kirschner wire per FIGS. 12Ai-12R.
Figure 14B:
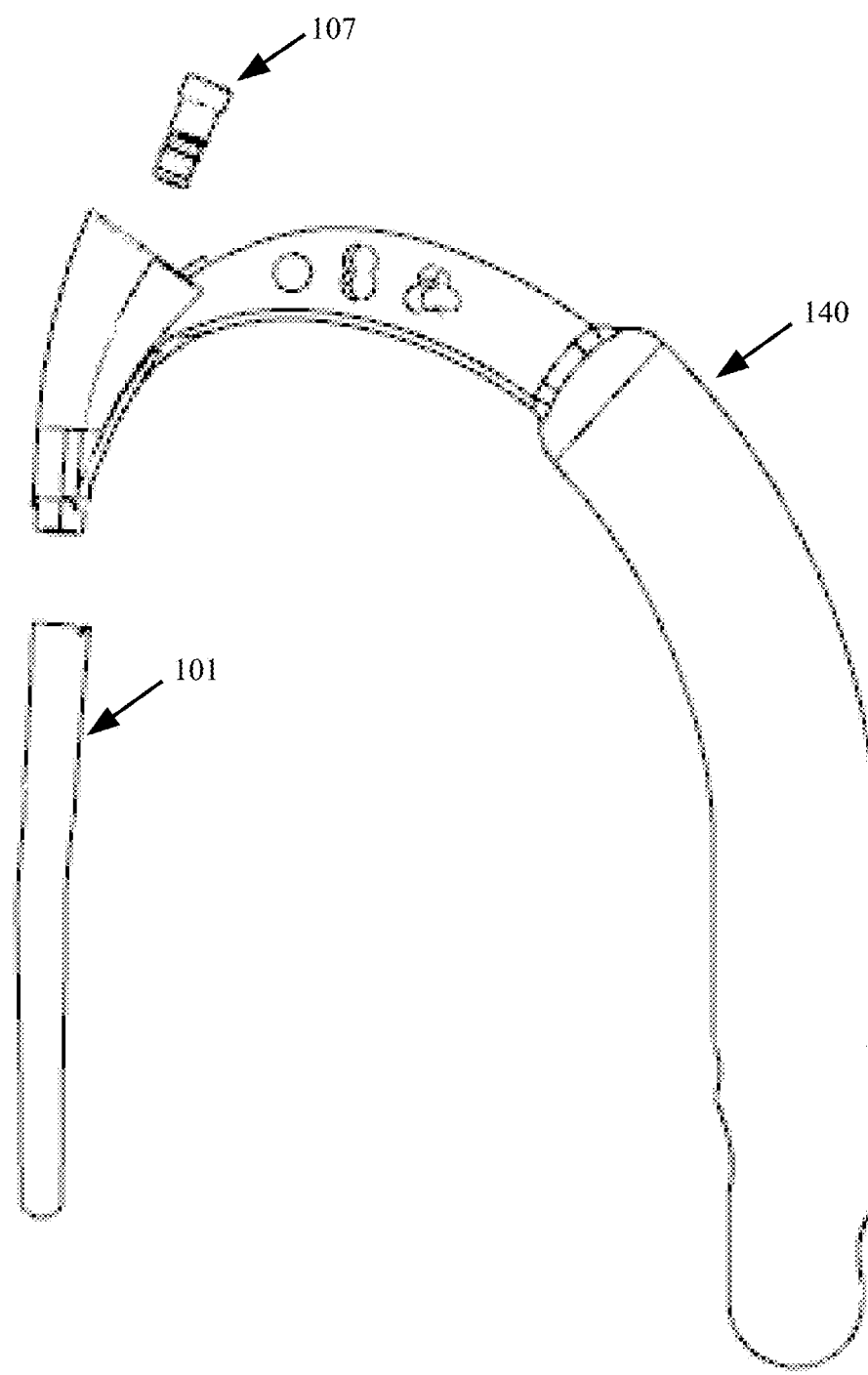
FIG. 14B is an exploded side view of the prosthesis placement apparatus and centering nail shown in FIG. 14A.
Figure 15A:
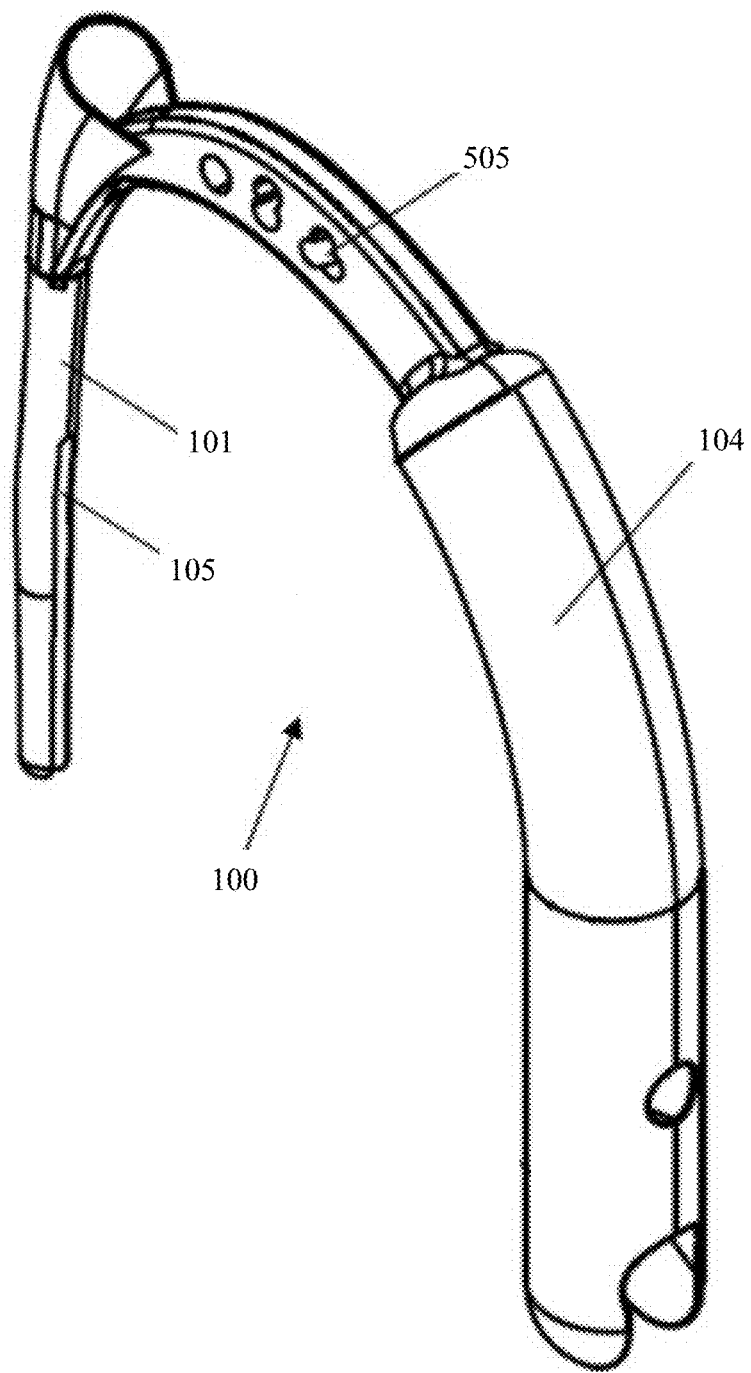
FIG. 15A is a first perspective view showing the prosthesis placement apparatus of FIG. 13A after centering nail has been releasably coupled thereto, for use in placing a Kirschner wire, as seen in FIGS. 12Ai-12R.
Figure 15B:
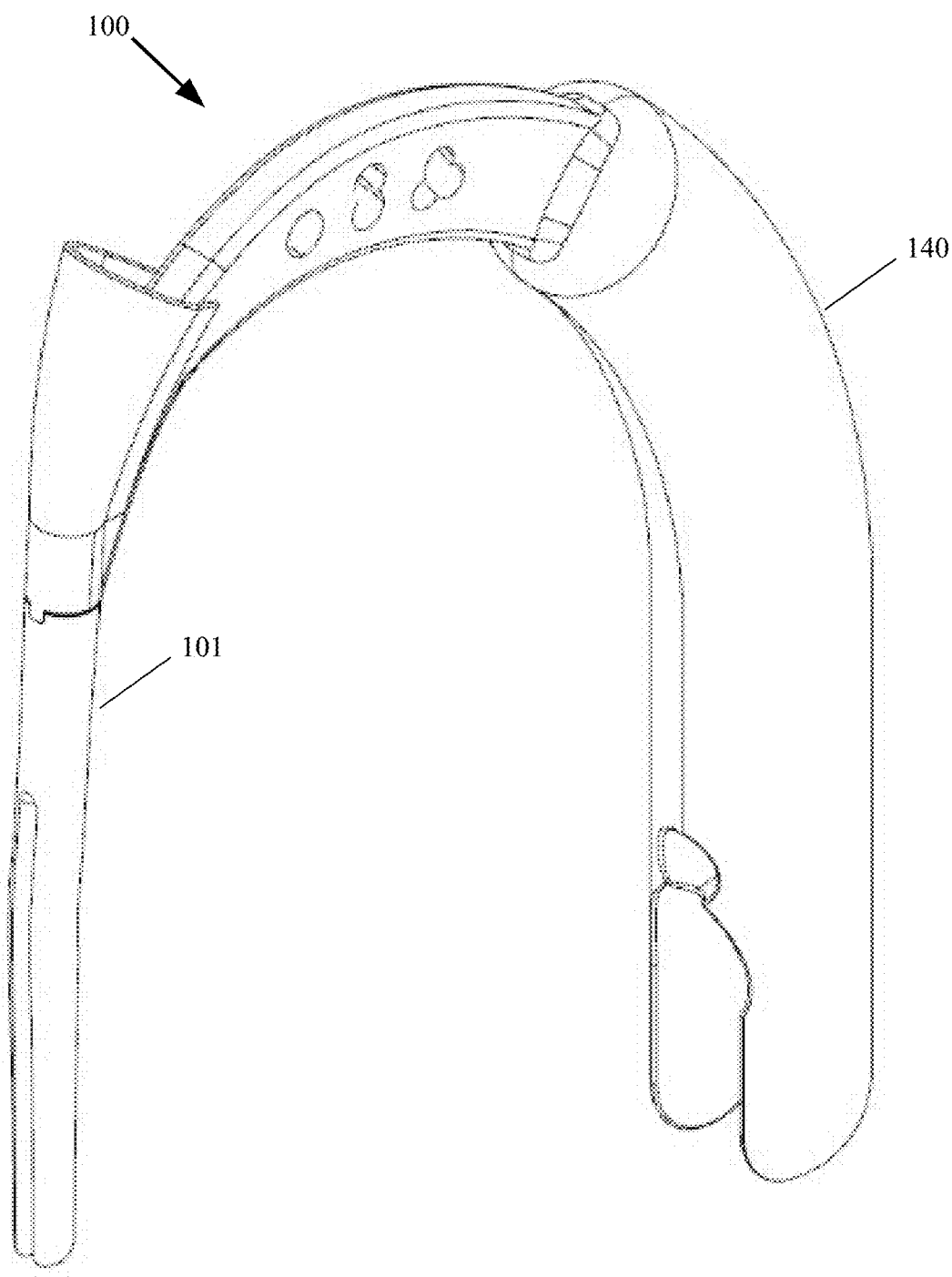
FIG. 15B is a second perspective view of the prosthesis placement apparatus and centering nail shown in FIG. 15A.
Figure 15C:
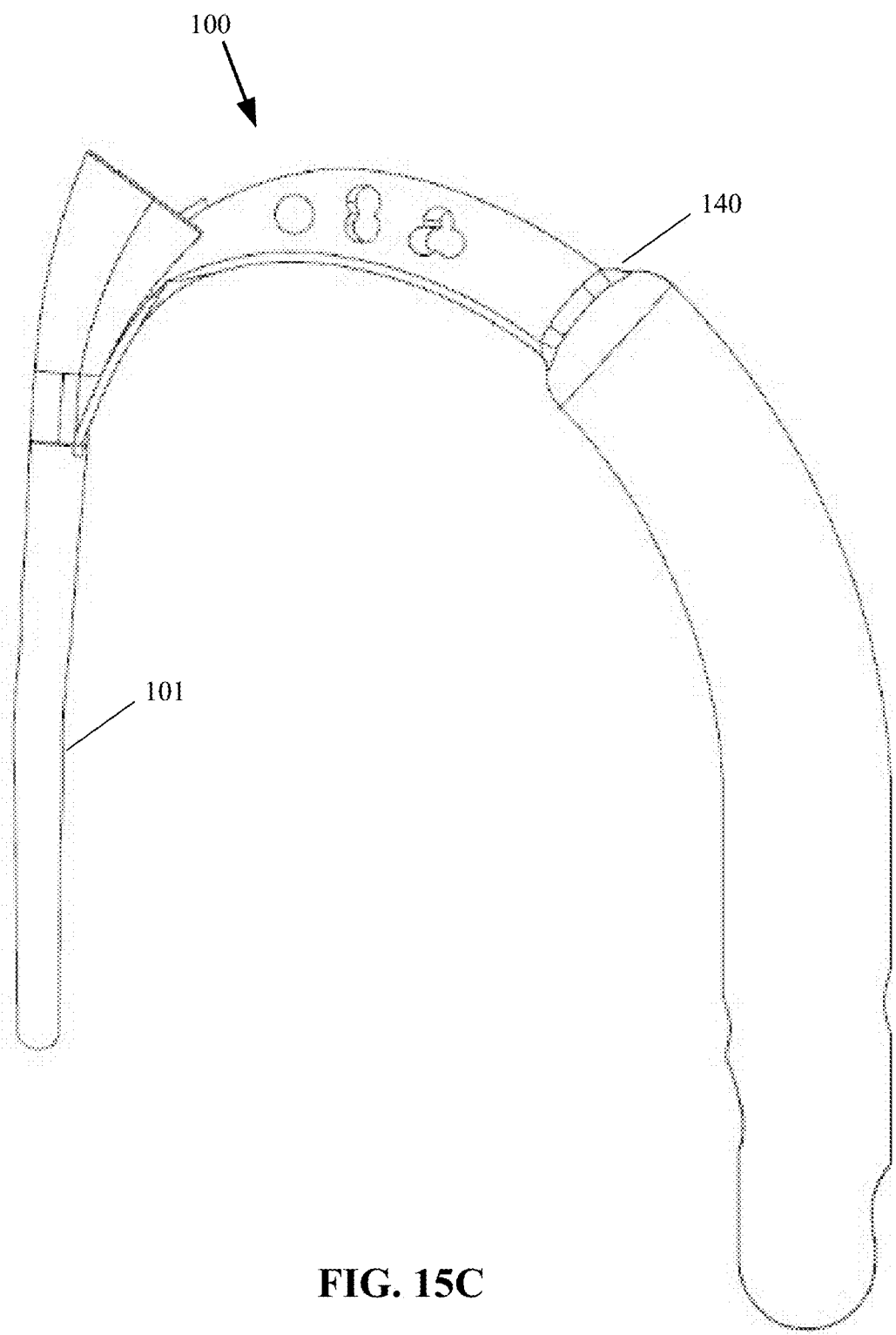
FIG. 15C is a side view of the prosthesis placement apparatus and centering nail shown in FIG. 15A.
Figure 15D:
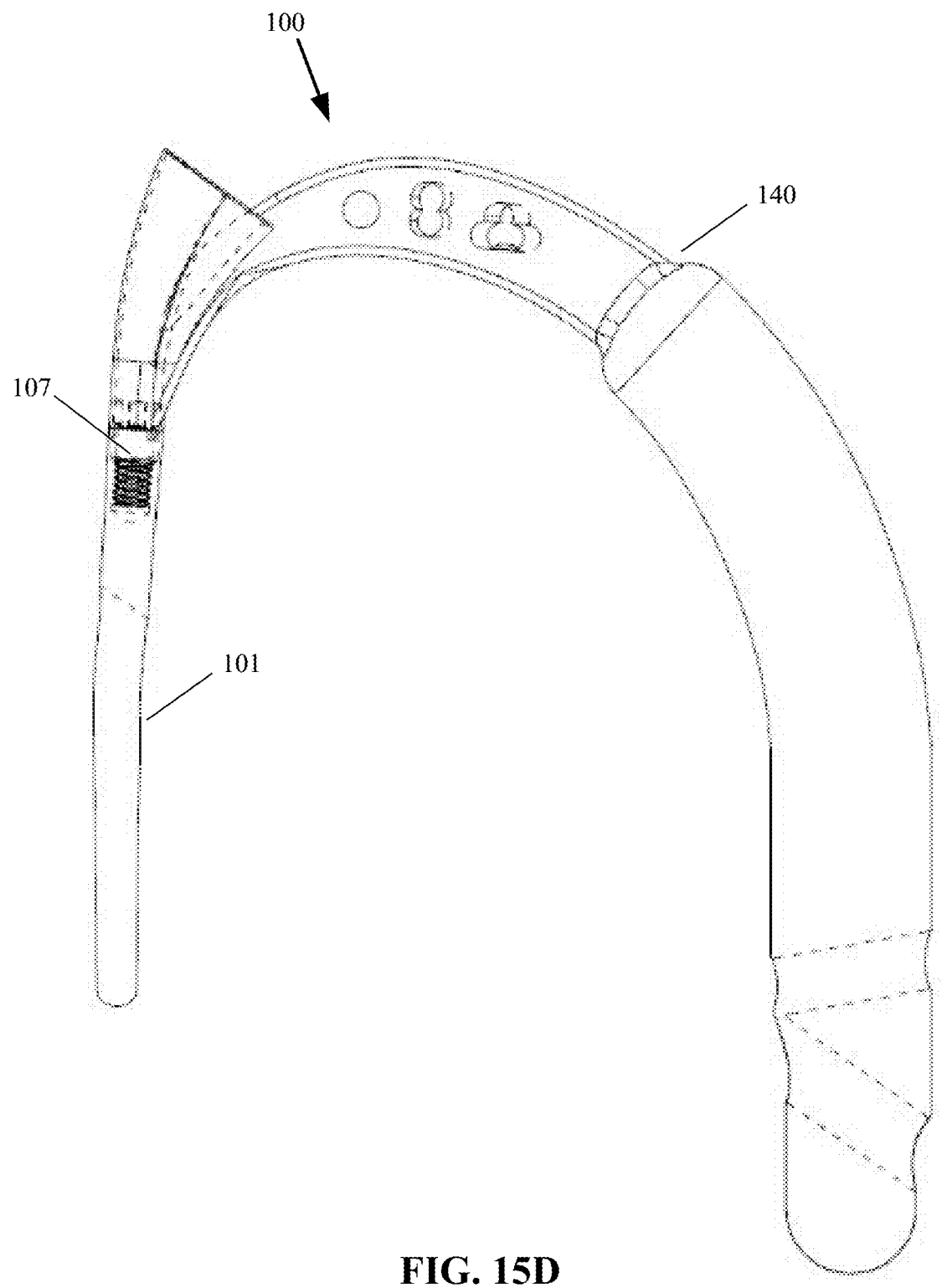
FIG. 15D is the side view of FIG. 15C, but showing the hidden features with dashed lines.
Figure 16A:
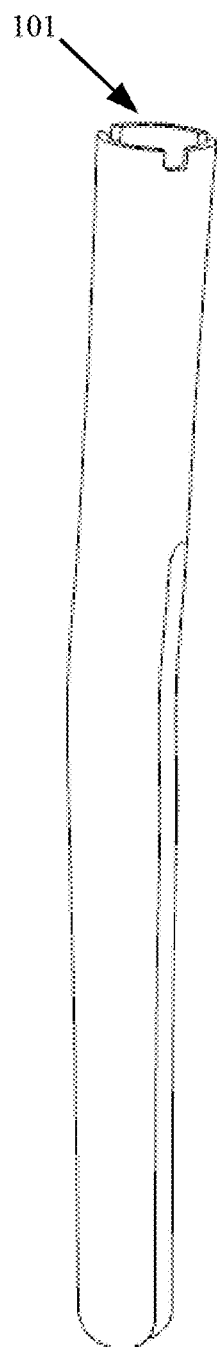
FIG. 16A is a perspective view of the centering nail of FIG. 14A.
Figure 16C:
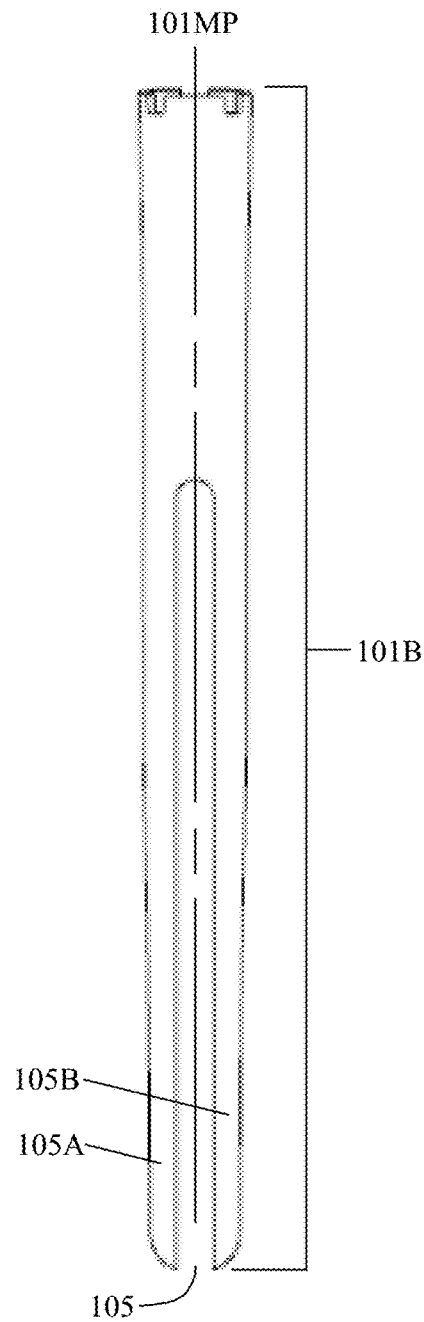
FIG. 16C is a front view of the centering nail of FIG. 16A.
Figure 16D:
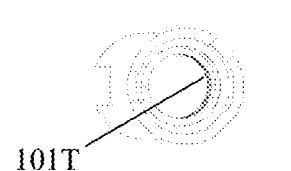
FIG. 16D is a top view of the centering nail of FIG. 16A.
Figure 16B:
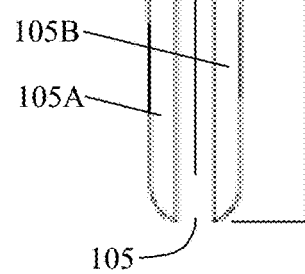
FIG. 16B is a side view of the centering nail of FIG. 16A.

The Kirschner wire centering device 100 is shown in the exploded views of FIGS. 14A-14B, and shown assembled in FIGS. 15A-15D. The Kirschner wire centering device 100 may be formed of a centering nail 101 which is shown in FIGS. 16A-16H, and a multi-function handle guide 140, shown by itself in FIGS. 13A-13F, which multi-function handle guide may also be used in conjunction with other components for insertion of the diaphyseal nail 3 (FIGS. 12M-12N), for installation of the locking device 24 (FIGS. 12P-12R), and for installation of the screws to secure the diaphyseal nail to the femur (FIGS. 12U-W). The centering nail 101 is intended for insertion in the femoral canal through the upper incision UI, while the multi-function handle guide 140 is positioned outside the patient's body.

As seen in FIGS. 13A-13F, the multi-function handle guide 140 may have a generally U-shaped body 141, with a graspable handle 145 formed proximate to, or extending up to a first end of the U-shaped body. The U-shaped body may be formed with a first opening 147 proximate to its first end, with the first opening having a cross-sectional shape a circular cross-sectional shape) defining an interior surface (i.e., at least a portion of a cylinder) with an axis oriented to be substantially coplanar with a mid-plane 140MP of the handle guide 140. The U-shaped body may also be formed with a second opening defining a pair of surfaces 146A and 146B that may be parallel, and which are preferably symmetrically formed about the mid-plane 140MP of the handle guide 140, and which may extend to interconnect with a central portion of the first opening 147, so that the first opening in effect has an interior surface that may be a portion of a cylinder (or other suitable geometric shape). The diameter of the cylindrical surface of the first opening 147 may thus be slightly larger than the distance between the parallel surfaces 146A and 146B, producing a keyway shaped opening (see FIGS. 13D-13E), which is configured to cooperate with other pieces of apparatus, as discussed herein.

The second end of the multi-function handle guide 140 may include any suitable features/apparatus that is configured to releasably couple the centering nail 101 thereto (and which second end also may later be releasably coupled to the diaphyseal nail 3). For example, the second end of the of the multi-function handle guide 140 may be formed with suitable recesses, while the nail may be formed with a corresponding protrusion or protrusions, so that it may form a bayonet mounting arrangement (e.g., similar to the metaphyseal component, which is discussed hereinafter). Alternatively, the second end of the multi-function handle guide 140 may be formed with external threading, which may threadably couple to internal threading 101T formed on the centering nail 101. In yet another embodiment, as seen in FIG. 13F, the second end of the multi-function handle guide 140 may be formed with a socket 140S, into which may be inserted the bolt 107, which bolt may therein be rotated as required to releasably couple its external threads 107T to the internal threading 101T formed on the centering nail 101. The socket 140S may preferably be formed so that it and the bolt 107 received therein will be substantially centered with respect to the mid-plane 140MP (i.e., it therefore also be centered with respect to the first opening 117 and the parallel surfaces 146A and 146B of the handle guide 140.

The centering nail 101, seen in FIGS. 16A-16F, may be formed to have an elongated body 101B with a suitable cross-section (e.g., substantially circular), a substantial portion of which body is configured to be received in the femoral canal (see FIG. 12Aii). Prior to the insertion of the centering nail 101, an entry will have been made through the upper incision UI in the tip of the greater trochanter by a drill bit of suitable diameter (See FIG. 12Ai). Thereafter, the rounded distal end the centering nail 101 is introduced through the tip of the greater trochanter of the femur, until at least the bottom portion 101BL is positioned in the femoral canal, and part of the upper portion 101BU is maintained with the opening formed in the greaten trochanter. Therefore, due to anatomical geometry, the upper portion 101BU is formed to be at an angle Θ with respect to the bottom portion (FIG. 16B), which angle Θ is between 4-6 degrees, and is preferably at about 4 degrees.

The centering nail 101 is formed with an opening 105 on the lower portion thereof creating a pair of prongs 105A and 105B, between which may be received the Kirschner wire, and which allows the Kirschner wire centering device 100 (more specifically the centering nail 101) to be removed by sliding past the Kirschner wires 102, 102', once they have been positioned. The opening 105 is particularly formed so that the inwardly facing surfaces of the pair of prongs 105A and 105B may preferably be symmetrically spaced apart from the mid-plane 101MP of the centering nail 101, and the internal threading 101T formed on the centering nail 101 may also be centered on the mid-plane 101MP. This symmetric positioning with respect to the mid-plane 101MP of the centering nail 101, and the centering of the first opening 147 and the parallel surfaces 146A and 146B of the multi-function handle guide 140 may serve to thereby center the sleeve 103 used to install the Kirschner wires.

The sleeve 103 is shown in FIG. 12Aiii just prior to being inserted into the openings in the handle guide 140. The sleeve 103 is shown in Detail in FIGS. 17A-17E. For the sleeve 103 to be slidably received in a slight clearance fit in the openings of the handle guide 140, as shown in FIGS. 12Aiii and 12B, at least a portion of its exterior must be formed to have a shape that corresponds to a portion of, or the entirety of, those openings. In one embodiment, a portion of the exterior of the sleeve 103 may be shaped to be slidably received in the first opening 147 in a close clearance fit or a slight friction fit, while a portion of the exterior of the sleeve remains clear of the parallel surfaces 146A and 146B of the multi-function handle guide 140. In one embodiment the opening 147 may be a portion of a cylindrical surface (see FIG. 13G), and the corresponding portion 103R1 of the sleeve 103 may be cylindrical, as seen in FIG. 17E. In another embodiment, a portion of the exterior of the sleeve may also be slidably received with respect to the parallel surfaces 146A and 146B of the multi-function handle guide 140 in a close clearance fit or a slight friction fit, and may have corresponding shapes (e.g., cylindrical); in one embodiment the portion 103R2 of the sleeve 103, which may be cylindrical, may be sized to slide between the parallel surfaces 146A and 146B in a close clearance fit or a slight friction fit. (Note that the surfaces 146A and 146B may be parallel and symmetrically positioned on opposite sides of the theoretical axis of the cylindrical opening 147). The sleeve 103 may be formed with one internal passageway 103A, which is configured to slidably receive and guide the Kirschner wire. Alternatively, the sleeve 103 may also be formed with a second passageway 103B, which may be used to slidably receive and guide a second Kirschner wire.

Figure 12C:
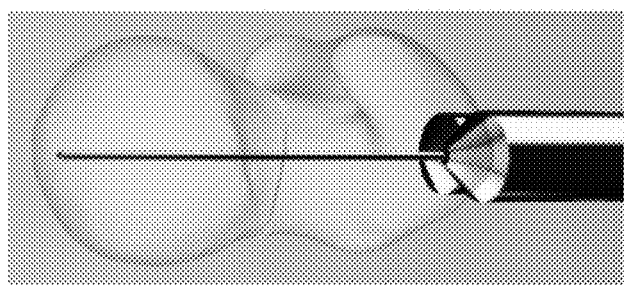
FIG. 12Ci is the front view of FIG. 12B, but shown after a Kirschner wire has been inserted into the upper cannula of the centering sleeve, and into the femur, through the centering nail, and into the femoral head.
Figure 12C:
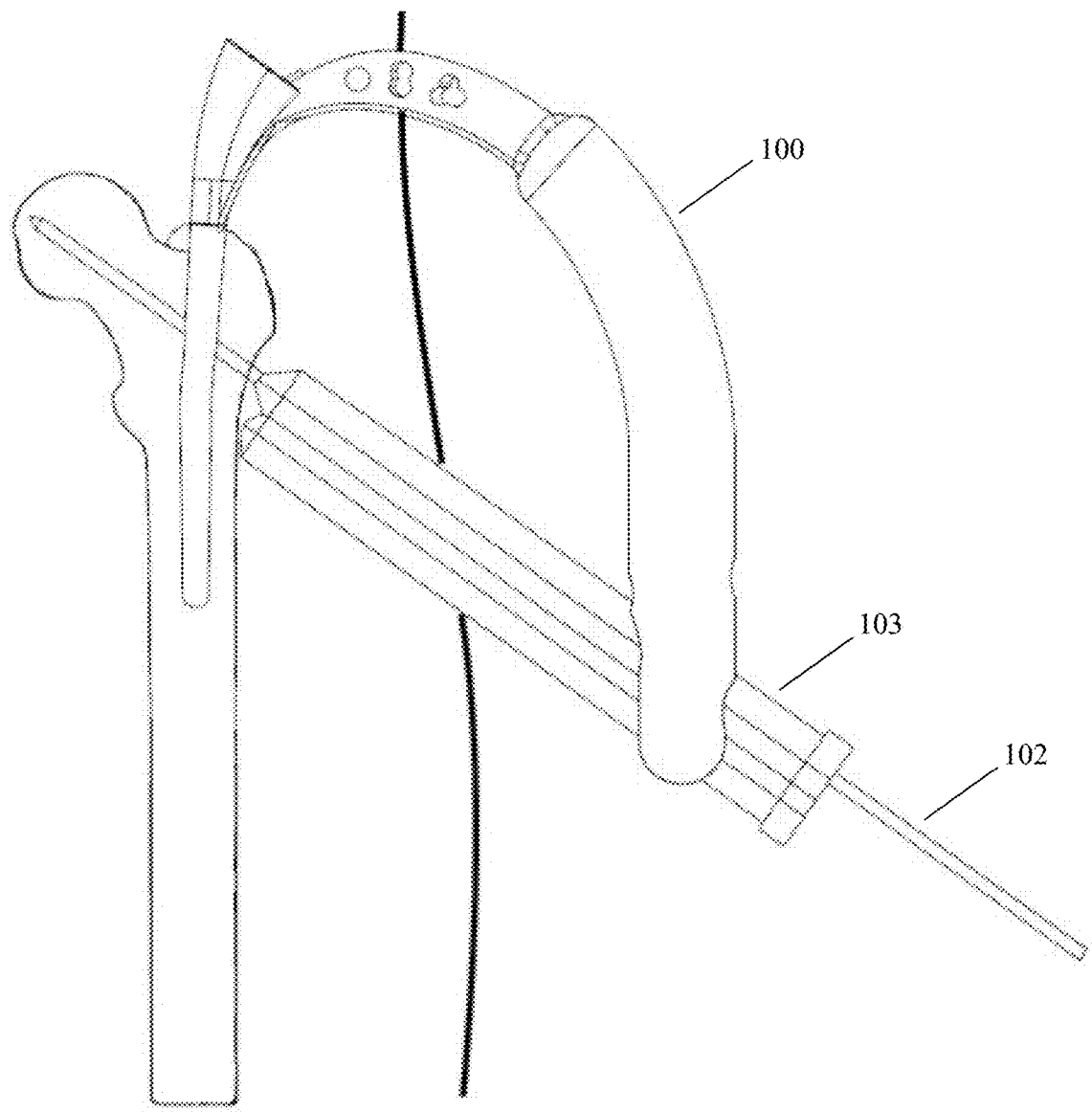
Figure 12D:
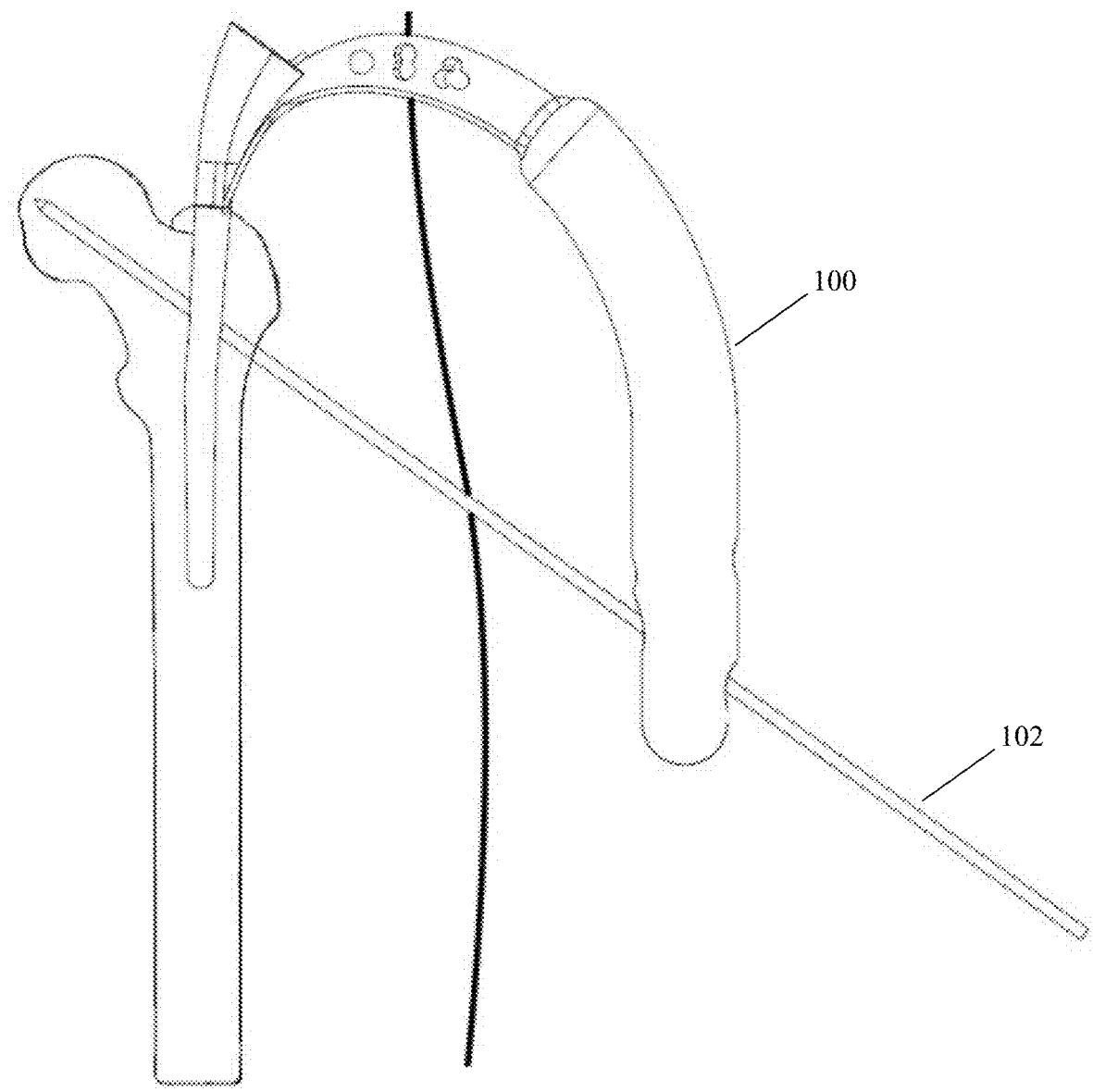
FIG. 12D is the front view of FIG. 12Ci, shown with the single Kirschner wire in position, but after the centering sleeve has been removed.
Figure 12E:
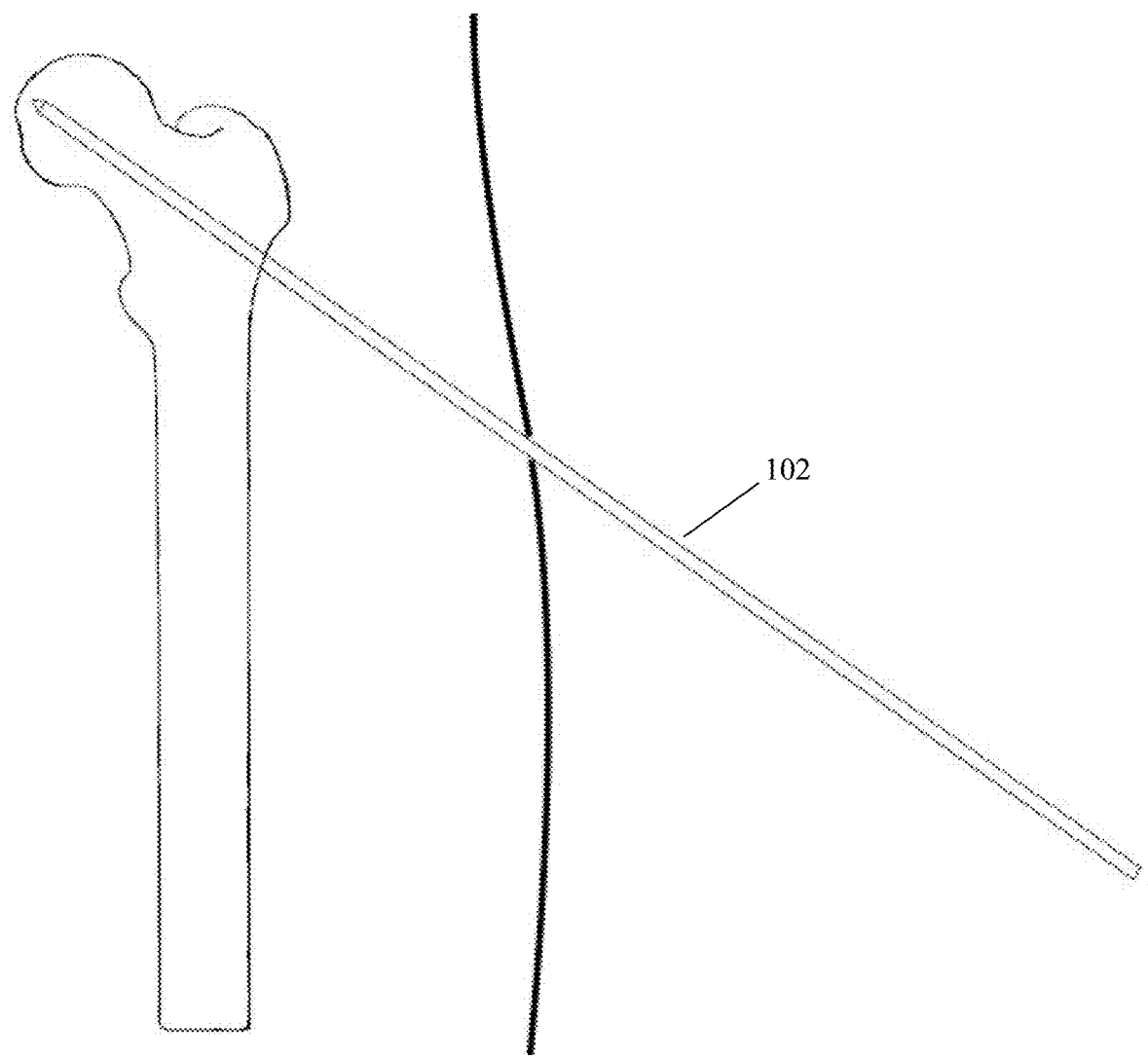
FIG. 12Ei is the front view of FIG. 12D, shown with the single Kirschner wire in position, but after the Kirschner wire centering device has been removed.

If the passageways 103A and 103B in the sleeve 103 are symmetric with respect to the mid-plane of the sleeve, the Kirschner wire(s) thereby inserted, as seen in FIGS. 12Ci and 12Cii, should ultimately also be substantially centered in the femur as required (see also FIG. 12ii), since the mid-plane relationships result in a central axis of each passageway being substantially centered between the inwardly facing surfaces of the pair of prongs 105A and 105B of the centering nail 101, when the sleeve 103 is received in the opening(s) in the handle guide 140.

Alternatively, the passageways 103A and 103B may just be positioned in the sleeve to ultimately provide such centering, without each of the noted features being so particularly positioned according to the respective mid-planes. It is also noted that the positioning and the axial direction of the opening 147 in the graspable handle 145 and the positioning and axial direction of the passageways 103A and 103B of the sleeve 103 are also formed and coordinated so that the first Kirschner wire 102 penetrates the femur at the appropriate angle with respect to the femur.

The centered positioning of the first Kirschner wire 102 is vital, and the surgeon must therefore check its position using an image intensifier that is usually available in operating rooms, or using another similar method. The surgeon uses the image intensifier to see the position of the Kirschner wire "directly," in both planes—antero-posterior and lateral. This way the surgeon will know if the position of the Kirschner wire(s) is suitably centered, or if instead the Kirschner wire must be modified by removing the wire, and by inserting/extracting and/or rotating the Kirschner wire centering device and reintroducing the Kirschner wire to a more suitable position.

Once the Kirschner wires 102, 102' are inserted into the femur and checked for being properly positioned, the sleeve 103 can be removed from the handle-guide 104 by being slid in the opposite direction from the arrows shown in FIG. 12Aiii, i.e., being slid away from the femur.

The Kirschner wire centering device 100 may then be removed, leaving the Kirschner wire 102 and 102' if used, in place.

Figure 12F:
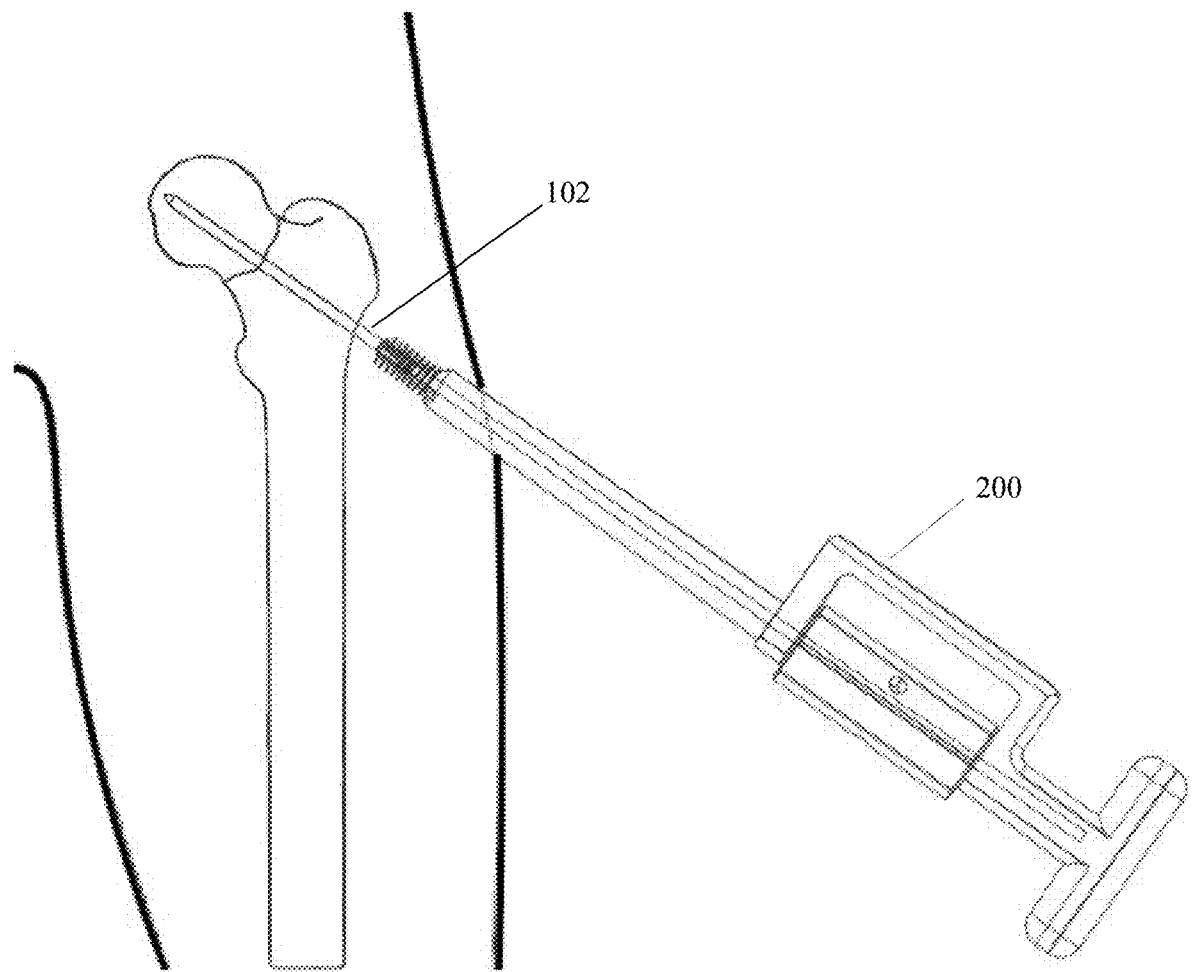
FIG. 12F is the front view of FIG. 12E, shown with the single Kirschner wire in position, and also shown after the cannulated extractor has been coupled to the wire by receiving the Kirschner wire through its axial hole.
Figure 12G:
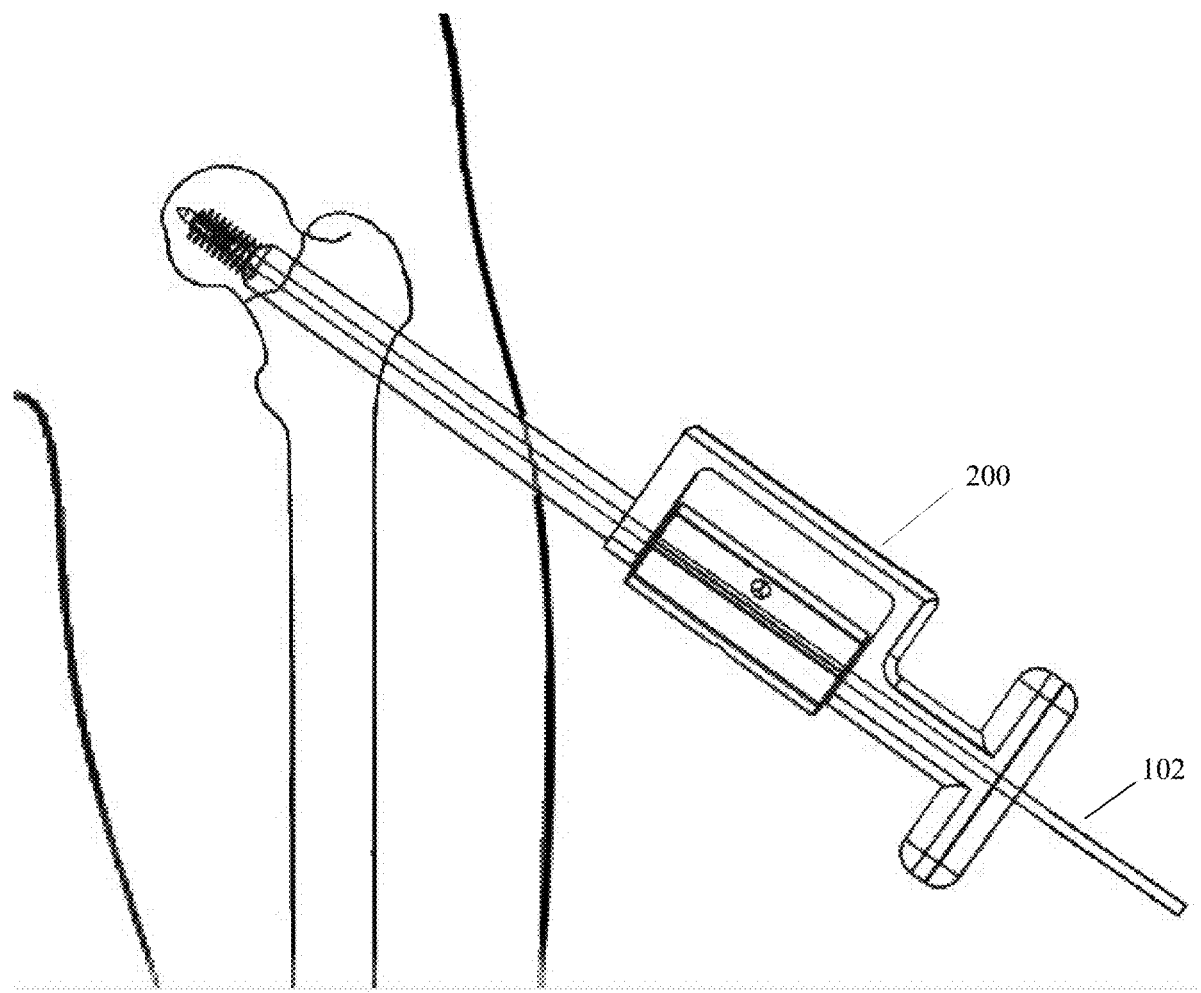
FIG. 12G is the front view of FIG. 12F, but shown after the handle member of the cannulated extractor has been rotated sufficiently to screw its external screw thread into the femur of the patient.
Figure 12H:
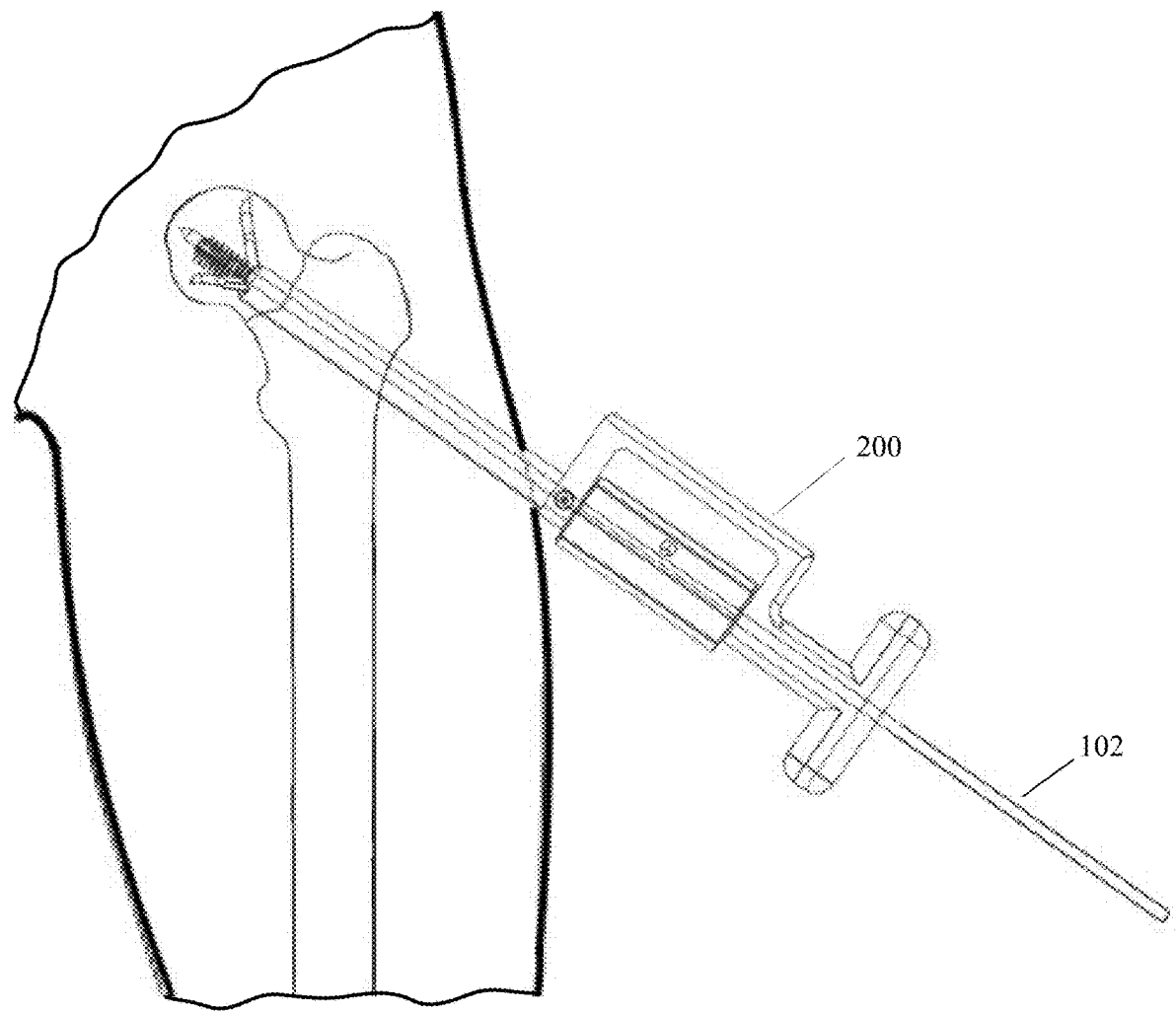
FIG. 12H is the front view of FIG. 12G, but shown after the actuation member of the cannulated extractor has been rotated sufficiently to translate and rotate its claws outwardly into the femur of the patient.
Figure 12I:
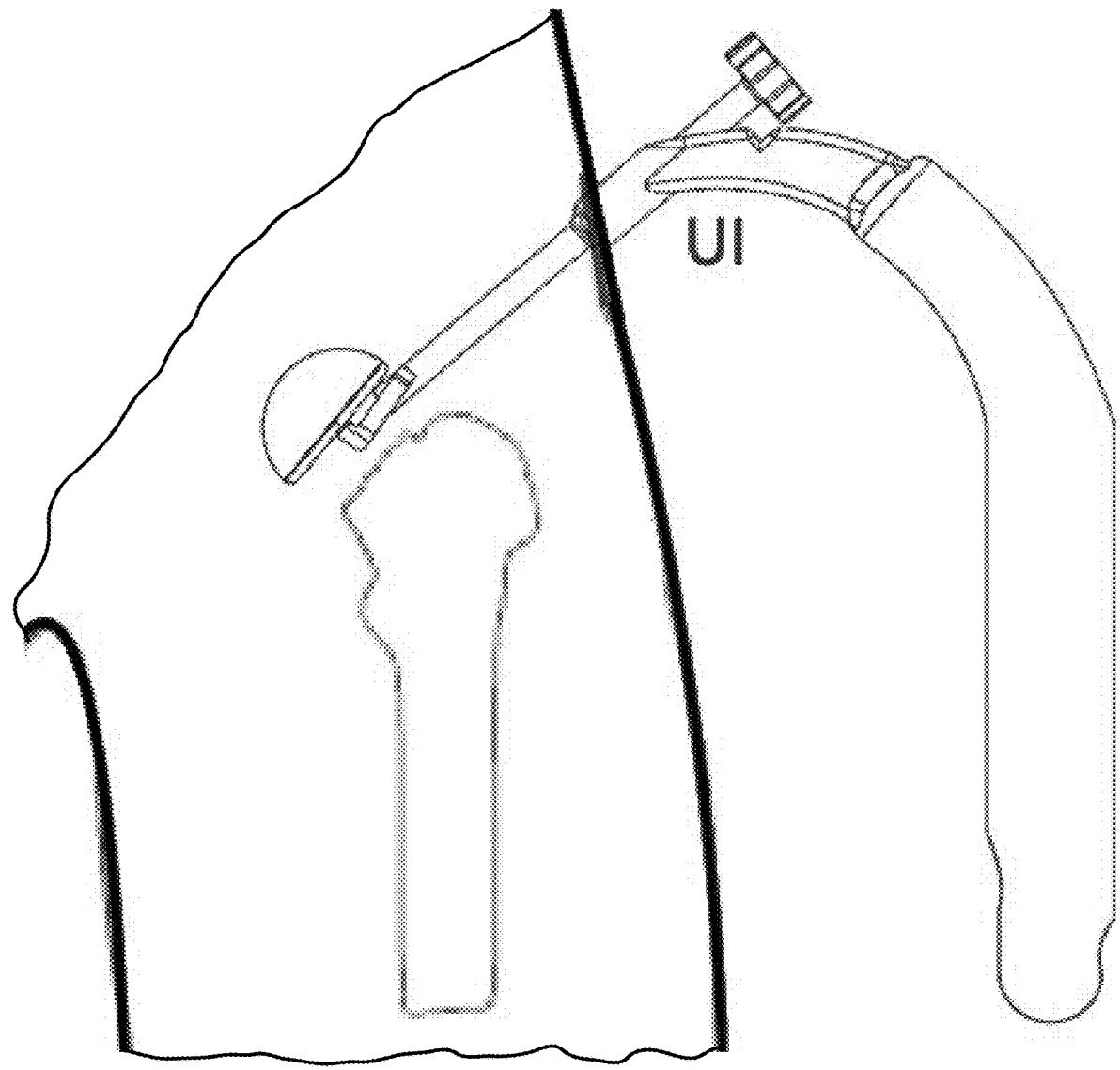
FIG. 12I is the front view of FIG. 12Hiii, but shown after the Head Component is introduced through the upper incision into its proper position using the Head Component Insertion Device.
Figure 12K:
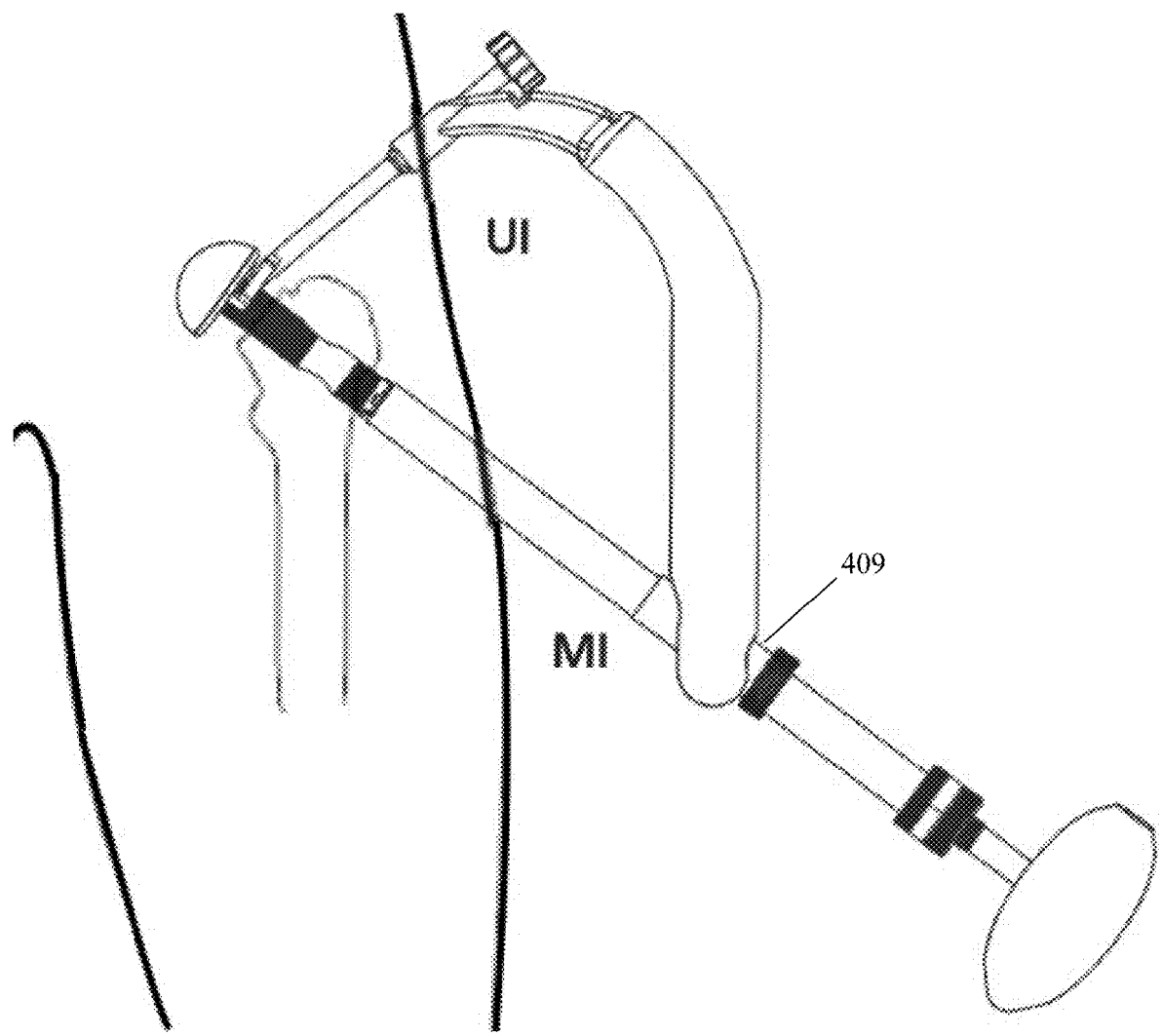
FIG. 12K is the front view of FIG. 12Jii, but showing the distal end of the Metaphyseal Component after being threaded into the bore of the Head Component using the Metaphyseal Component Insertion Device.
Figure 12L:
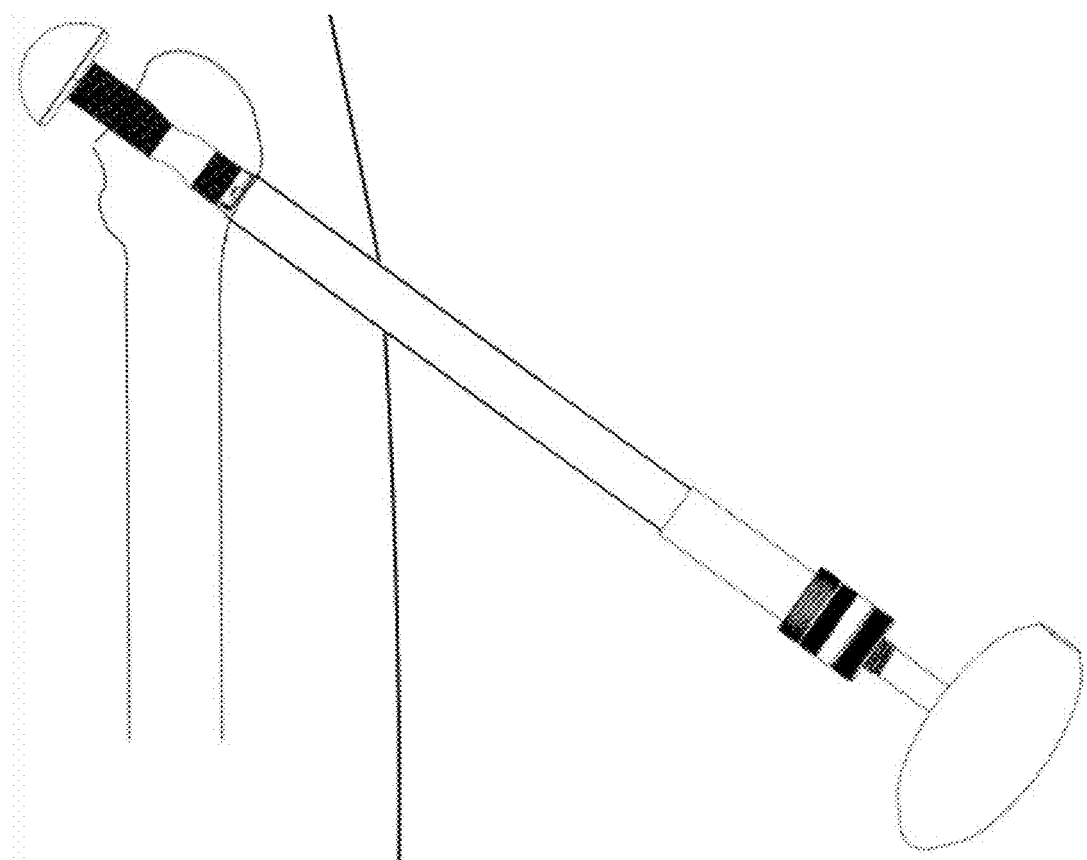
FIG. 12L is the front view of FIG. 12K, but shown after the sleeve of the Metaphyseal component is withdrawn away from the Handle Guide of the Head Component Insertion Device, and after the Head Component Insertion Device has been removed.

As noted above, a process that better enables removal of the femoral head or humeral head during the prosthesis implant procedure, and which utilizes at least one Kirschner wire and a cannulated head extractor 200, is shown in FIGS. 12F-12Hiv. To better understand the method of use of the head extractor 200, the extractor is first described in detail.

The cannulated head extractor 200 is shown assembled in FIGS. 18A-18C and 18E-18L, while the component parts are shown in an exploded view in FIG. 18D, which includes a cannulated screw member 210, a holder member 220, an inner screw member 230 with a plurality of claws 240 pivotally attached thereto, and a rotatable actuation member 250.

The cannulated screw member 210 is shown in detail in FIGS. 19A-19H. The cannulated screw member 210 may be formed to include an outer shaft 213 that extends from a first end 211 to a second end 212, with the first end of the outer shaft having an opening 214 defining a hollow interior cavity. The second end 212 of the outer shaft 213 may be formed to include a plurality of openings 215 interconnected with the hollow interior cavity. Two openings 215 may be formed to be clocked 180 degrees apart. In another embodiment, as shown in the figures, three openings 215 may be formed to be clocked 120 degrees apart. A protrusion may extend away from the second end 212 of the outer shaft 213 which may have an external screw thread 216 formed therein, with the external screw thread being configured to be screwed into a bored opening in the femoral or humeral head. The outer shaft 213 may have a first hole 217 and a second hole 218 formed in proximity to the first end 211, which may be used for mounting the cannulated screw member 210 to the handle member 220, using a first screw/bolt 200A (FIG. 18E) and a second bolt 200B, respectively (FIG. 18F).

The handle member 220 is shown in detail in FIGS. 20A-20H. The handle member 220 may be formed to include a rectangular-shaped body 223 with a rectangular-shaped recess 224 formed therein, resulting in a channel shape for the body, the center of which may be used as a handle. A first side 223A of the channel shape may have an elongated protrusion 225 protruding therefrom, the distal end of which may transition into a cross-wise member 226, which may also serve as a handle. The first side 223A of the channel shape may have a cylindrical opening 227 formed therein, which may be used for mounting one end of the actuation member 250 thereto (see FIG. 18C), and which may permit travel of the inner shaft member 230 therein. The second side 223B of the channel shape may also have a cylindrical opening 228 formed therein, which may be used for mounting the other end of the actuation member 250 thereto, and for also mounting/receiving the first end 211 of the outer shaft 213. Therefore, the second side 223B of the channel shape may also may have a first orifice 223Bi (FIG. 20B) and a second orifice 223Bii (FIG. 20C), which may permit insertion of the mounting screws/bolts 200A/200B, for securing of the second end 212 of the outer shaft 213 of the cannulated screw member 210 to the handle member 220.

Figure 21A:
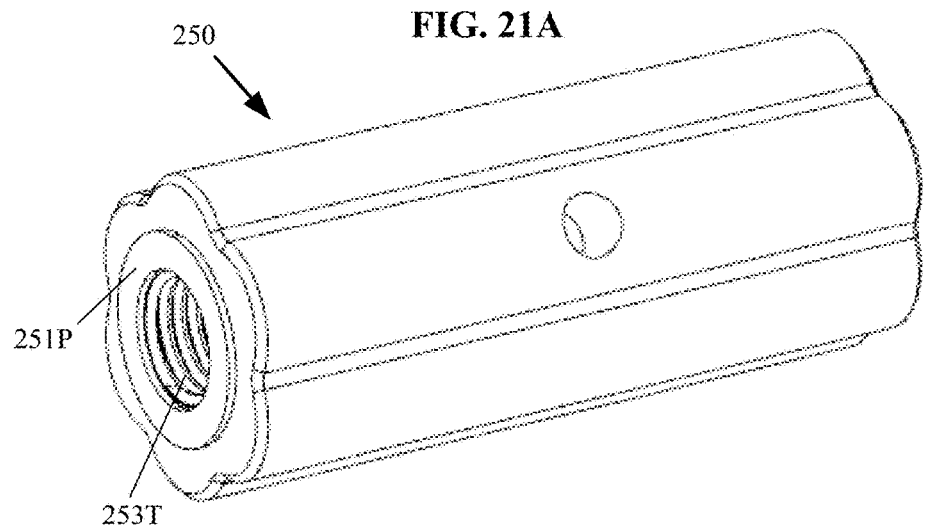
Figure 21C:
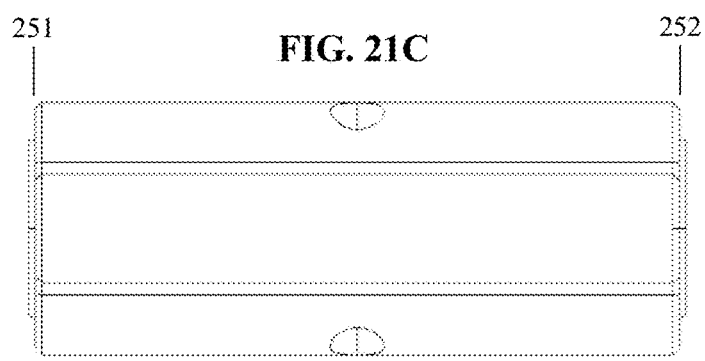
Figure 21B:
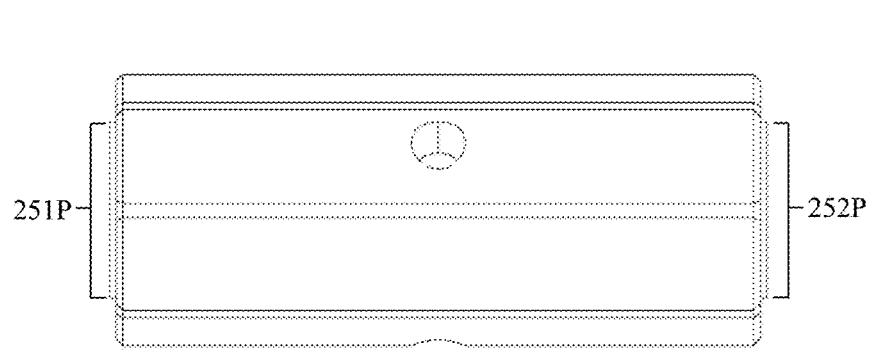
Figure 21D:
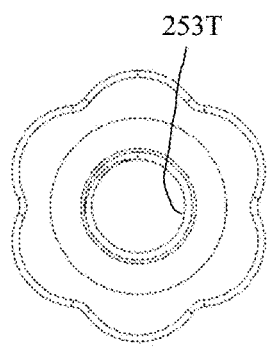
Figure 21E:
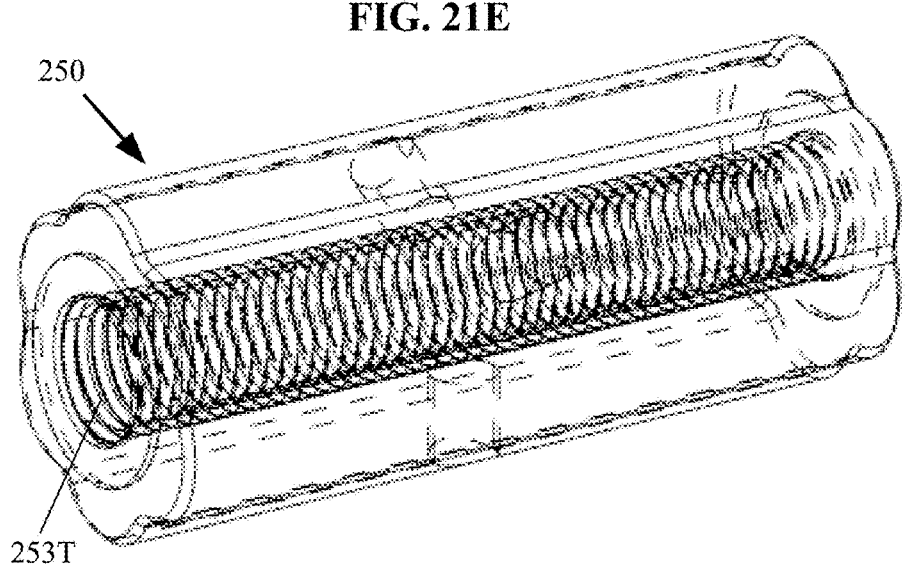
Figure 21G:
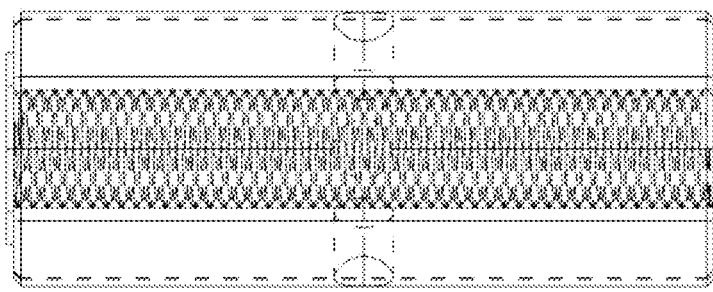
Figure 21G:
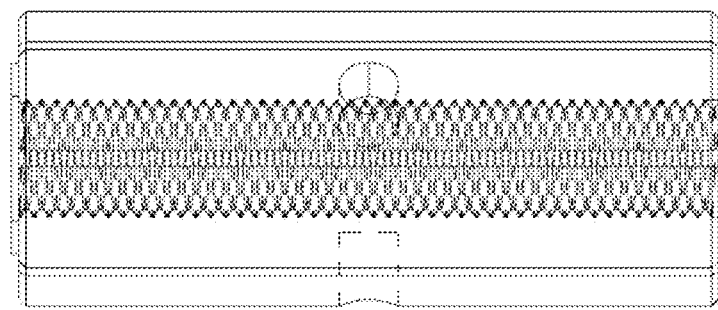
Figure 21G:
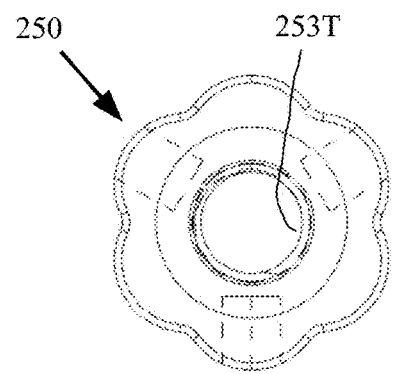

The actuation member 250 is shown in detail in FIGS. 21A-21H. The actuation member 250 may be generally cylindrical in shape, although other shapes may alternatively be used, and it may extend from a first end 251 to a second end 252. The outer surface of the actuation member 250 may be smooth, or may instead have a coarse surface texture to assist a user in rotating the member to actuate the inner shaft 230. In another embodiment, the outer surface of the actuation member 250 may have a series of regular undulations formed therein to provide for better gripping by the user's fingers, as seen in FIG. 21D. Protruding from each of the first and second ends 251/252 may be respective cylindrical protrusions 251P/252P, which may be used to rotatably mount the actuation member 250 to the cylindrical openings 227/228 of the handle member 220 as shown in FIG. 18E. A substantially concentric cylindrical through-opening 253T may be formed in the actuation member 250, and may be formed to include internal threading, as seen in FIG. 21A, and FIGS. 21E-21G.

Figure 18C:
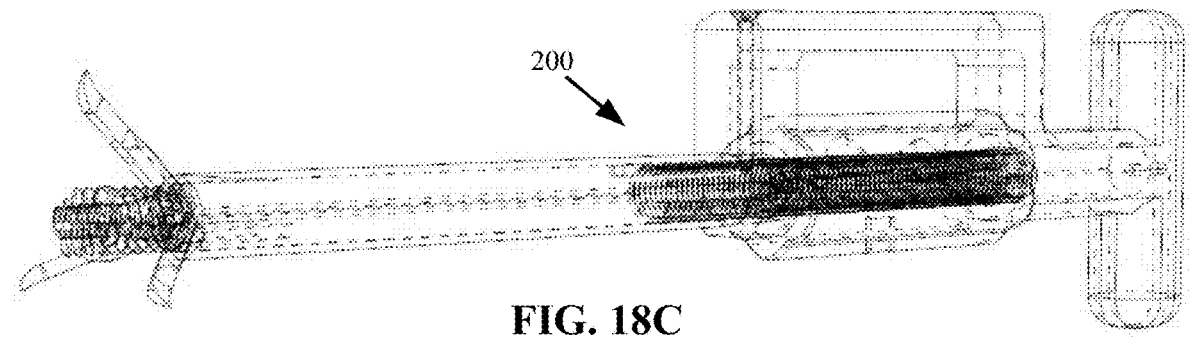
FIG. 18C is the perspective view of FIG. 18B, but with each of the hidden features of the component parts being shown with dashed lines.
Figure 18J:
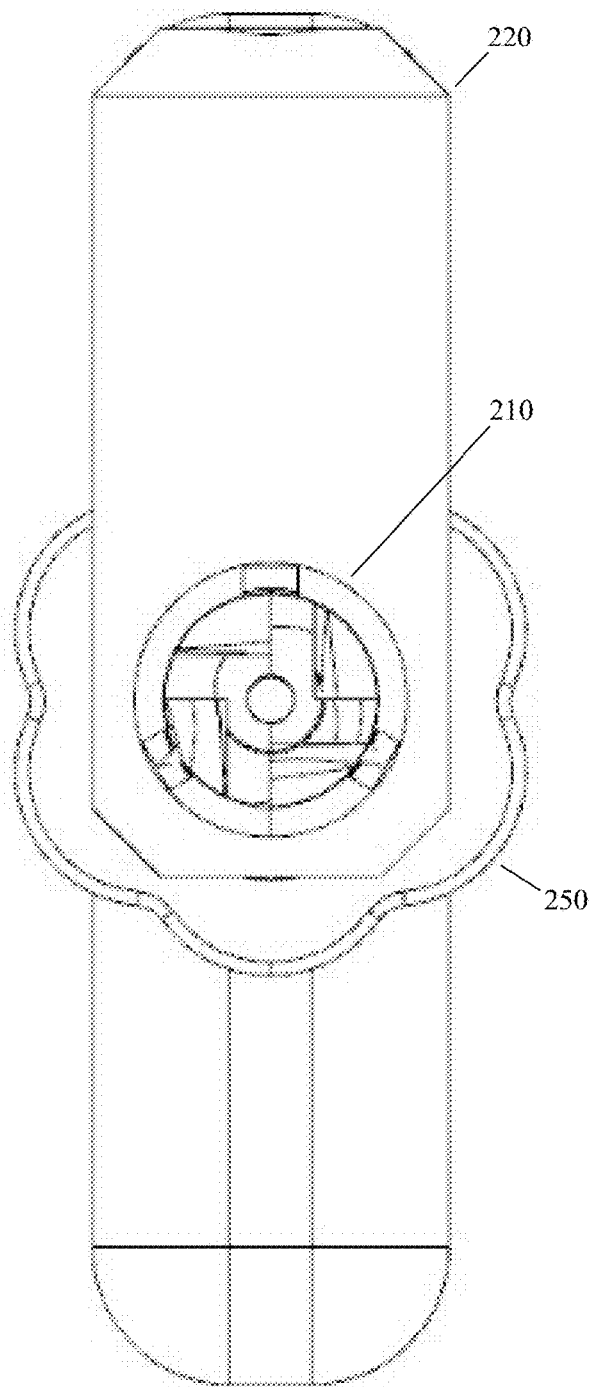
FIG. 18J is the front view of FIG. 18I, but shown enlarged.
Figure 18I:
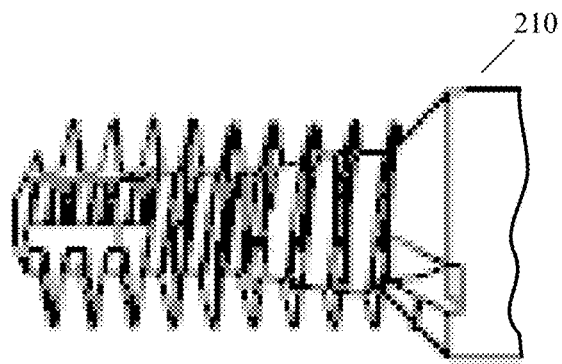
FIG. 18I is the side view of FIG. 18E, but showing the external screw thread of the cannulated screw member of the cannulated extractor of FIG. 18E greatly enlarged.
Figures 18K, 18L:
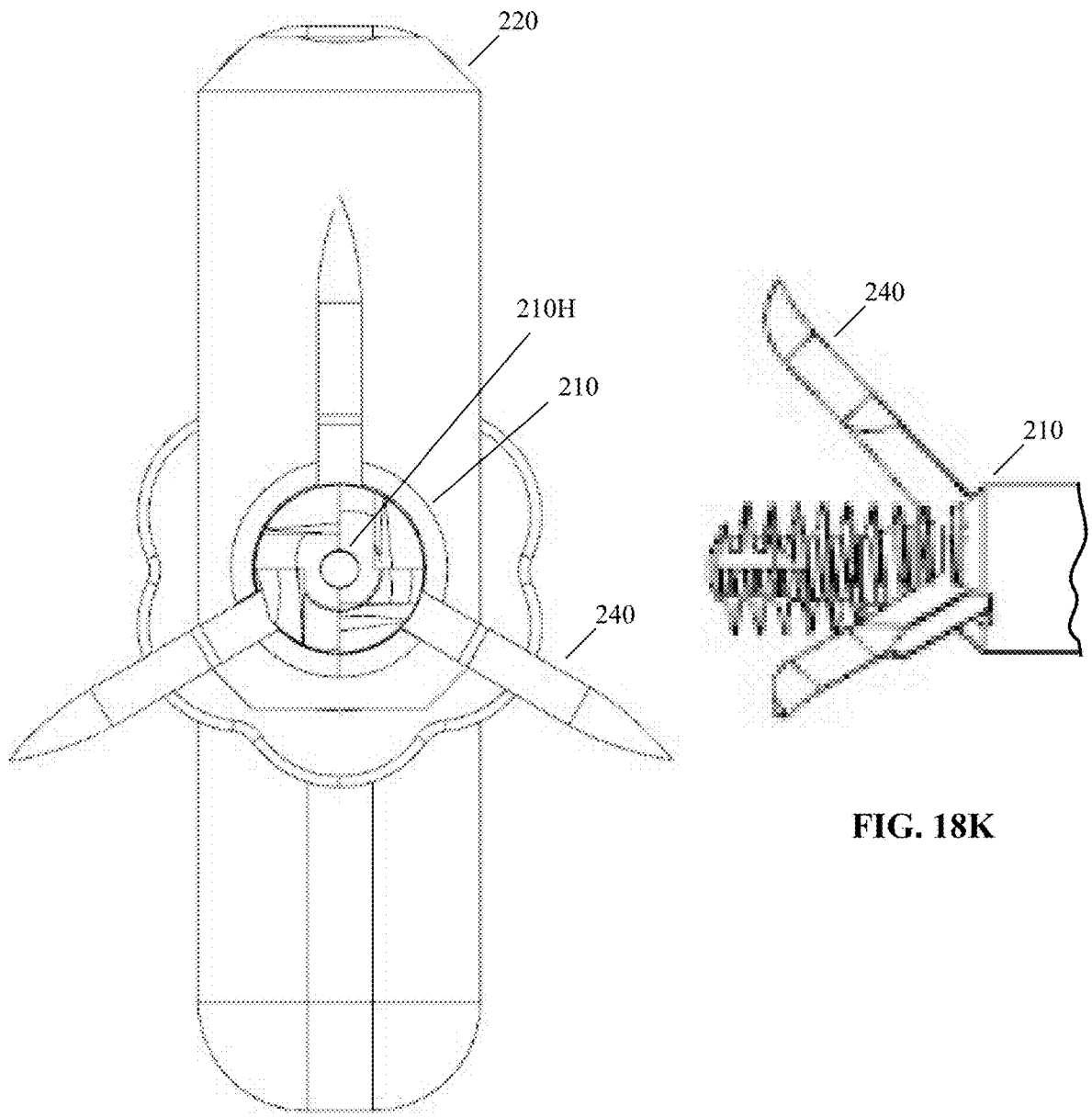
FIG. 18K is the side view of FIG. 18I, but shown with the claws in the extended position.
FIG. 18L is the front view of FIG. J, but shown with the claws in the extended position.

The inner shaft member 230 is shown in detail in FIGS. 23A-23J. The shaft 230 may be cylindrical, extending from a first end 231 to a second end 232. At least a portion of the inner shaft member beginning at or proximate to the second end 232 may be formed with external threading 233T that is configured to threadably engage the internal threading 253T of the actuation member 250. The first end of the inner shaft member 230 includes a plurality of openings 234, which plurality may number the same as the number of openings 215 in the cannulated screw member 210. The openings 234 may be formed as radial slots, into which the ends of the claws 240 (FIGS. 22A-22D) may be received, and may be pivotally attached thereto using pins 260 (FIG. 23J) through the holes 241 in the claws. The inner shaft member 230 also includes at least one cross-wise slotted through-opening 235 being elongated parallel to a center axis of the inner shaft member. A second slotted through opening 236 (FIG. 23A) may also be formed therein, being clocked 90 degrees to the first slotted opening. The slotted through-openings (235 and/or 236) are each configured to receive the first screw/bolt 200A therethrough, as seen in FIGS. 18C and 18D, which may act as an anti-rotation pin with respect to the inner shaft member 230 so that rotation of the actuation member 250 causes only translation of the inner shaft member 230 and no co-rotation.

Assembly of the cannulated head extractor 200 may proceed as follows. The actuation member 250 may first be rotatably mounted within the rectangular-shaped recess 224 of the handle member 220 (see FIG. 18D and FIG. 18E). Next the inner shaft member 230 may be mounted to (i.e., threadably engaged) with respect to the actuation member 250 (FIG. 18D and FIG. 18E), and the rotations to produce such threaded engagement may position the second end 232 of the inner shaft member proximate to the distal end of the opening 227 in the handle member 220, and may terminate when a portion of its slotted opening 235 is aligned with the first orifice 223Bi of the handle member 220. Next that cannulated screw member 210 may be slid over the jaws 240, which may be gathered together in a retracted position, and also be slid over a portion of the inner shaft member 230, until its end 211 is received in the opening 228 in the handle member 220, with its hole 217 being aligned with the first orifice 223*bi* of the handle member. As such, the axis of the first orifice 223*bi* of the handle member 220 will be substantially aligned with the axis of the hole 217 of the cannulated screw member 210, which coterminous axes will transect the slotted opening 235 in the inner shaft member 230, permitting the screw/bolt 200A to be inserted therein to join the assembly together.

Figure 18M:
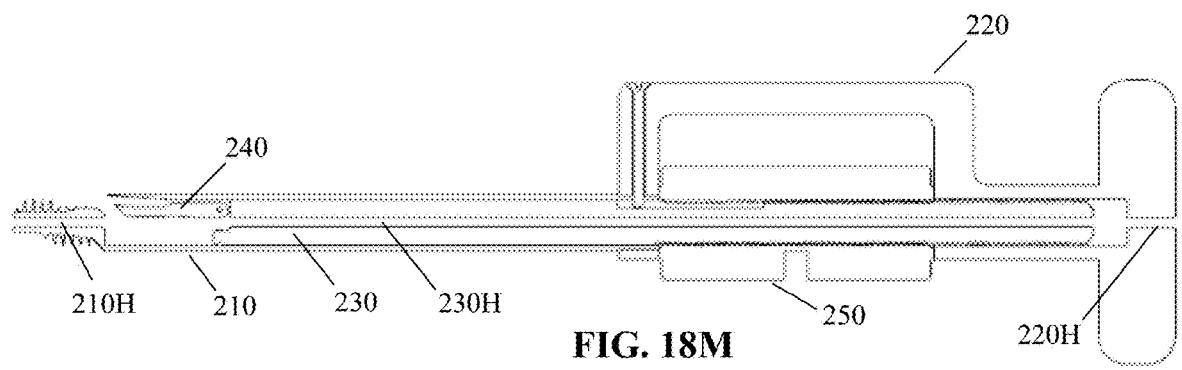
FIG. 18M is a side cross-sectional view through the cannulated extractor of FIG. 18A.
Figure 18N:
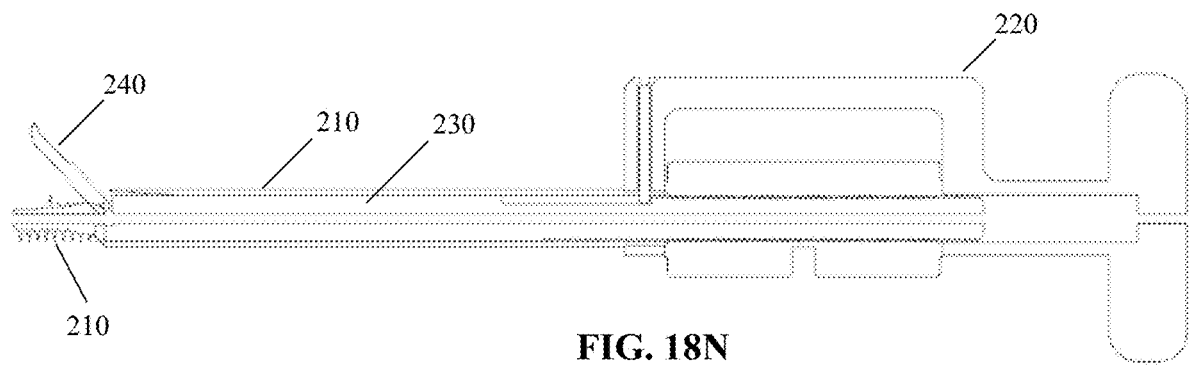
FIG. 18N is the side cross-sectional view of FIG. 18M, but shown with the claws in the extended position.
Figure 18P:
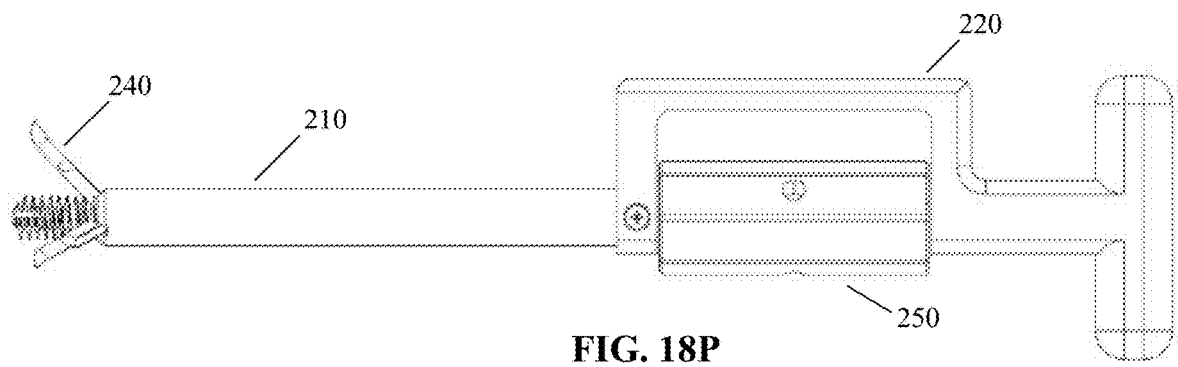
FIG. 18P is the side view of FIG. 18, but shown with the claws in the extended position.
Figure 19A:
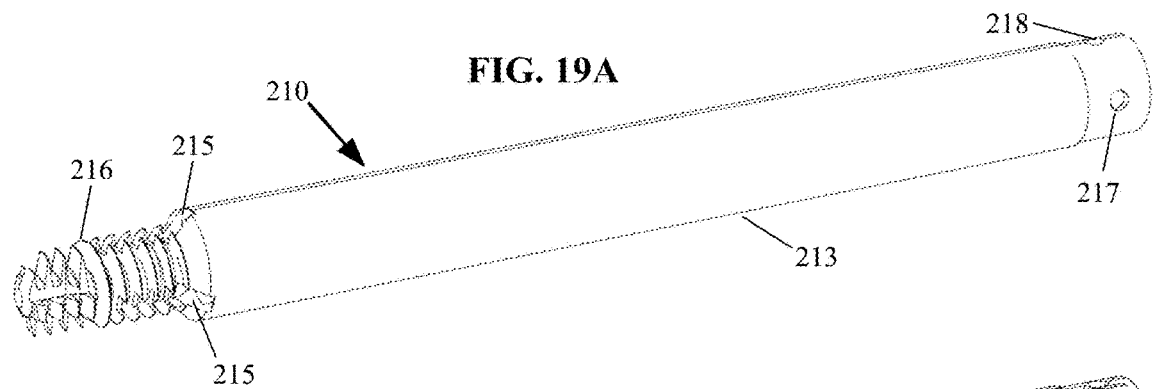
FIG. 19A is a first perspective view of the cannulated screw member of the cannulated extractor of FIG. 18A.
Figure 19B:
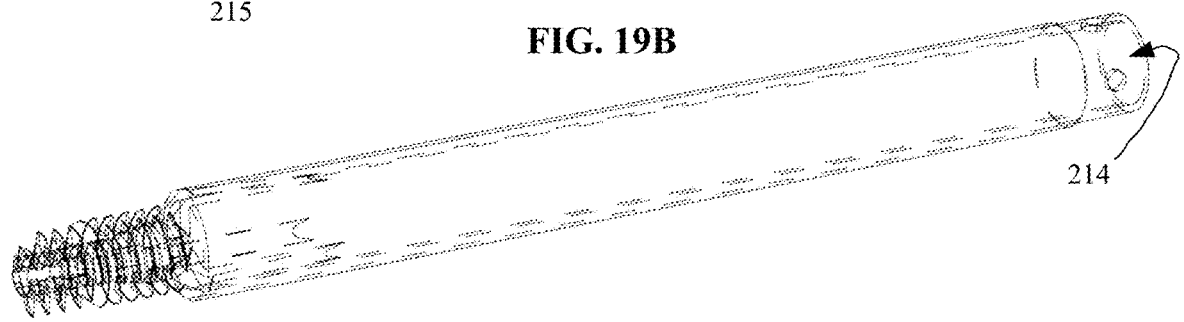
FIG. 19B is the perspective view of FIG. 19A, but with the interior features shown with dash lines.
Figure 19C:
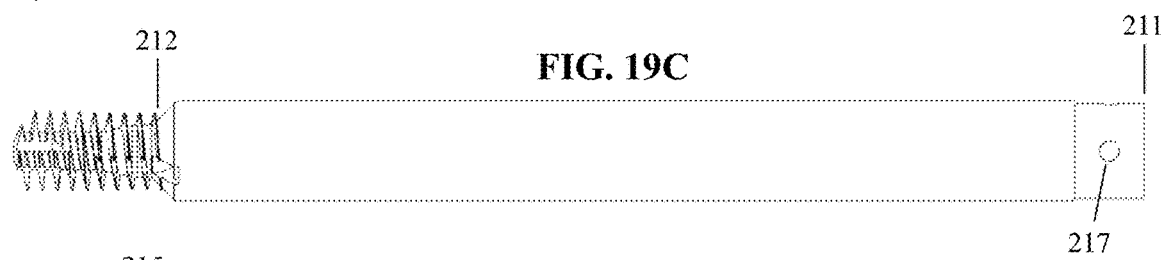
FIG. 19C is a side view of the cannulated screw member of the cannulated extractor of FIG. 18A.
Figure 19D:
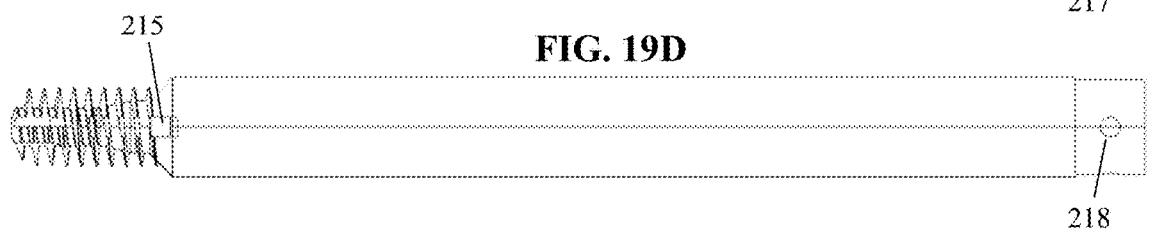
FIG. 19D is a top view of the cannulated screw member of the cannulated extractor of FIG. 18A.
Figure 19E:
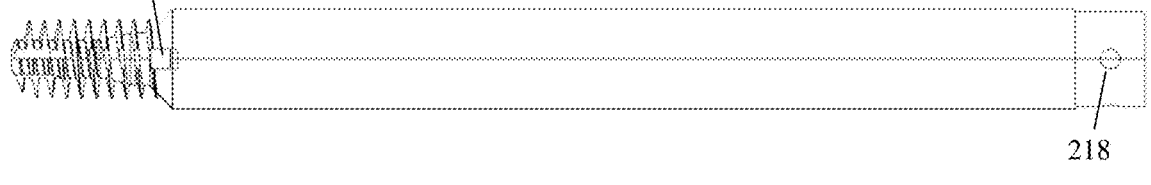
FIG. 19E is the side view of FIG. 19C, but with the interior features shown with dash lines.
Figure 19F:
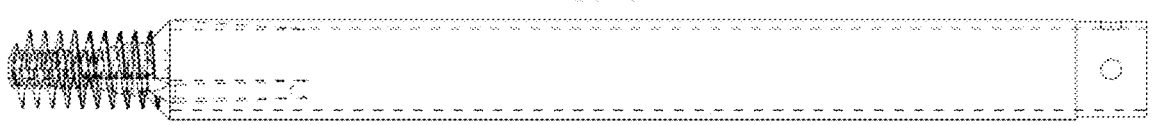
FIG. 19F is the top view of FIG. 19D, but with the interior features shown with dash lines.
Figure 19G:
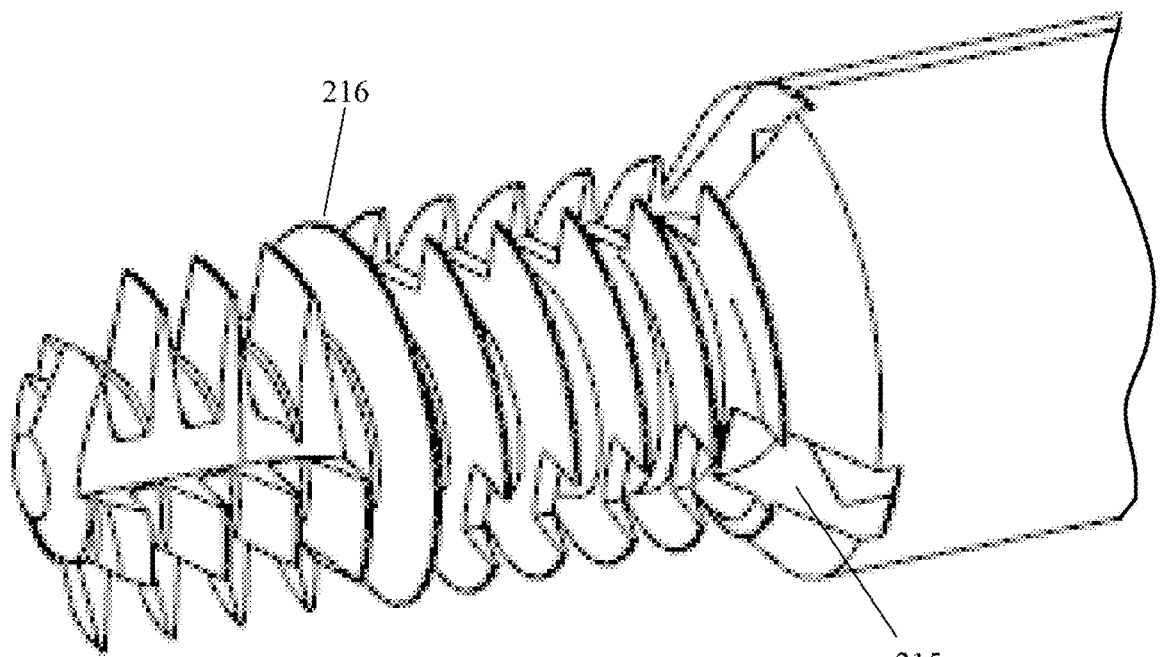
FIG. 19G is the perspective view of FIG. 19A, but showing the external screw thread of the cannulated screw member greatly enlarged.
Figure 19H:
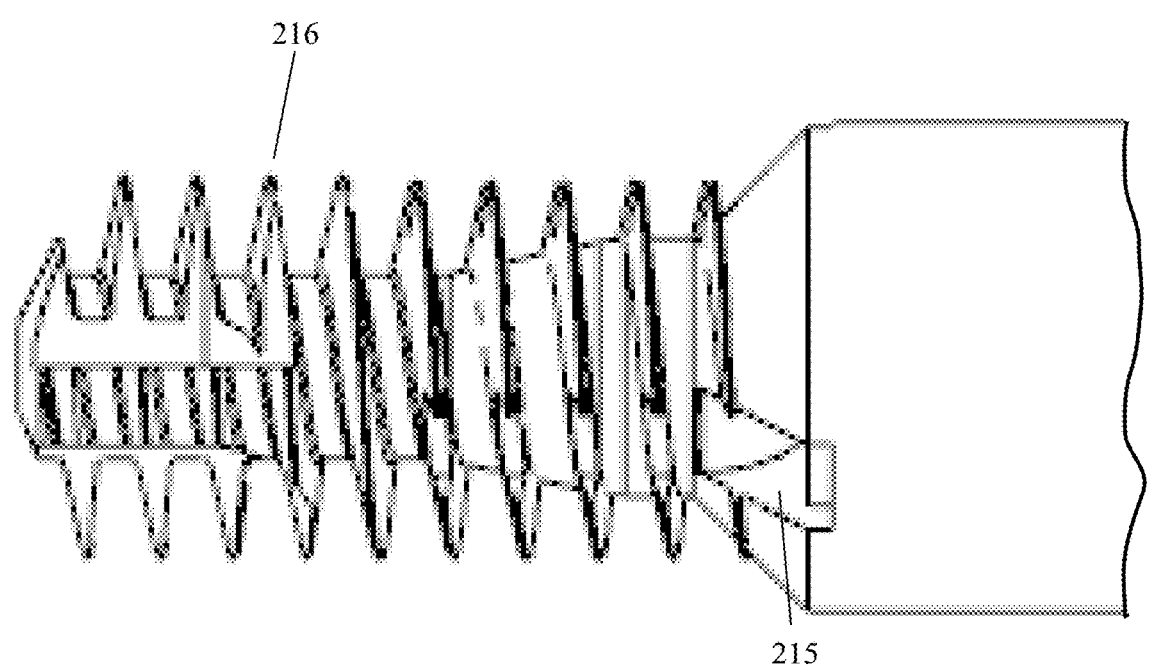
FIG. 19H is the side view of FIG. 19C, but showing the external screw thread of the cannulated screw member greatly enlarged.
Figure 20E:
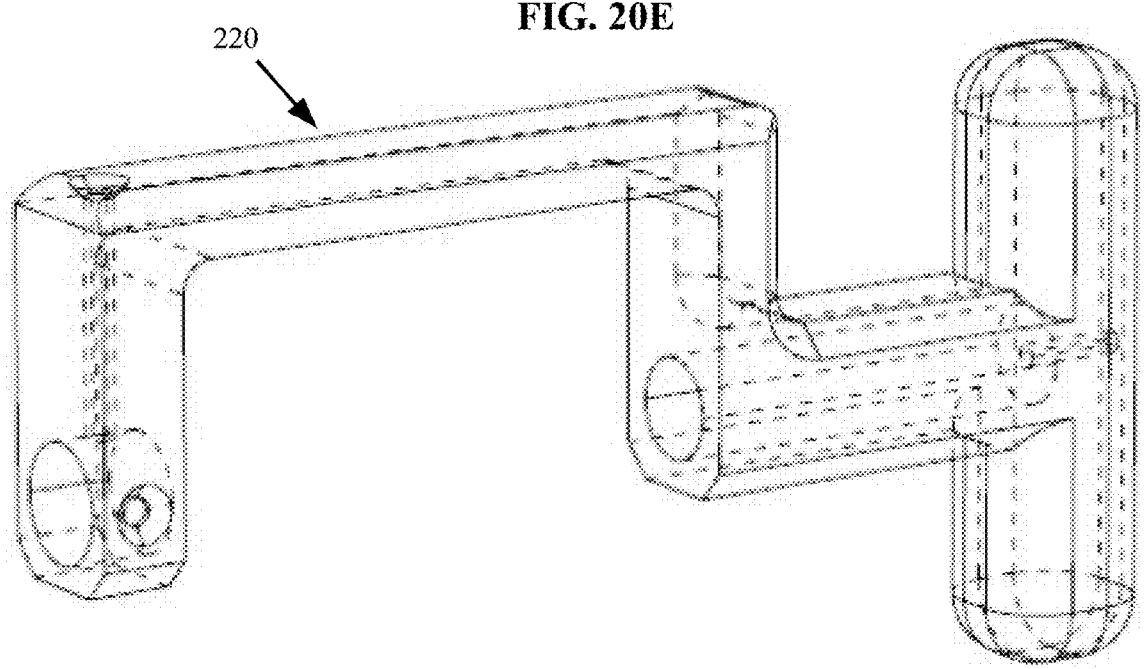
FIG. 20A is a perspective view of the handle member of the cannulated extractor of FIG. 18A.
FIG. 20B is a side view of the handle member of FIG. 20A.
FIG. 20C is a top view of the handle member of FIG. 20A.
FIG. 20D is a rear view of the handle member of FIG. 20A.
Figure 20G:
Figure 20G:
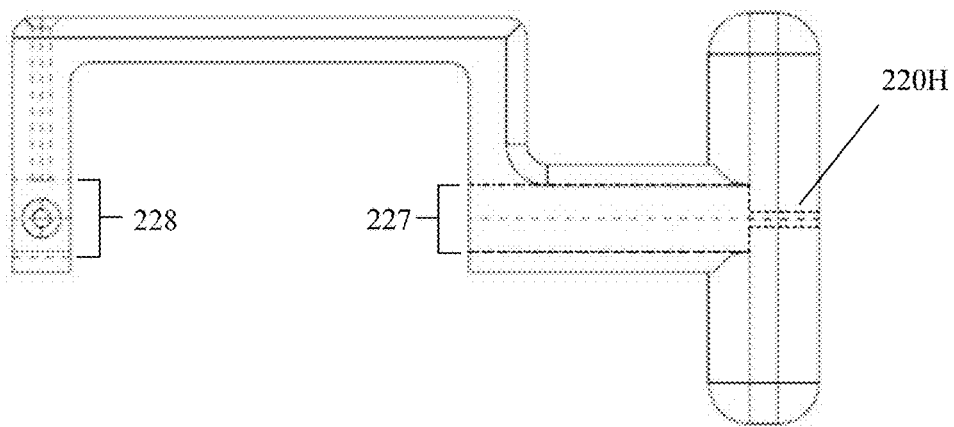
Figure 20G:
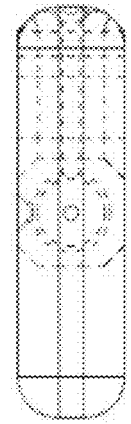

Mechanical operation of the cannulated head extractor 200 may proceed as follows. The rotation of the actuation member 250 in a first rotation direction (e.g. clockwise as seen when looking at the cannulated extractor 200 from the handle member 220 toward the external screw thread 216), may cause translation of the inner shaft member 230 toward the cross-wise member 226 of the handle member, which results in the claws 240 be in a retracted position (see FIG. 18M). The rotation of the actuation member 250 in a second rotation direction (i.e., clockwise as seen when looking at the cannulated extractor 200 from the handle member 220 toward the external screw thread 216), may cause translation of the inner shaft member 230 away from the cross-wise member 226 of the handle member, which causes the claws 240 to exit the openings 215 of the cannulated screw member 210, as they are clocked to be aligned therewith because of alignment of the axes of the first orifice 223*bi* of the handle member 220, the hole 217 of the cannulated screw member 210, and slotted opening 235 in the inner shaft member 230. The particular shape of the claws 240 and the shape of the outer shaft 213 of the cannulated screw member 210 around those openings 215 operates to drive each of the claws into an extended position as the inner shaft member 230 translates away from the cross-wise member 226 of the handle member (FIG. 18N), in the same manner as a cam and follower.

As to the formation of the component parts of the cannulated head extractor 200, it is further noted: that the external screw thread 216 of the cannulated screw member 210 may have an axial hole 210H formed substantially concentric with a central axis of the outer shah 213; that the inner shaft member 230 may have an axial hole 230H formed substantially concentric with the central axis of the inner shaft member; and that the handle member 220 may have an axial hole 220H formed to be substantially concentric with the central axes of the cannulated screw member 210 and the inner shaft member 230 when mounted thereto. The substantially concentric axial holes (210H, 230H, 220H) in each of the cannulated screw member 210, the inner shaft member 230, and the handle member 220 are configured to allow the passage of the first Kirschner wire 102 tightly therethrough (e.g., in a slight clearance fit, or a slight interference/friction fit). Thus, the cannulated head extractor 200 can be guided to the femoral head using the Kirschner wire 102 without the tolerance of that passage affecting the result.

The second Kirschner wire 102' will serve to anchor the femoral head to prevent the rotation thereof when the cannulated femoral head extractor 200 is inserted in the femoral head. It is therefore optional. In FIG. 12Ciii the second Kirschner wire 102' is shown situated beneath the first Kirschner wire 102, but the exact position may vary.

Before inserting the cannulated femoral head extractor 200 through the middle incision MI, the lateral cortical bone of the femur must have been drilled from the same middle incision using a drill bit of sufficient diameter to allow the external screw thread 216 of the cannulated extractor to pass through the aperture that is thereby made. A cannulated drill bit, which will use the same Kirschner wire as a guide, will be used for this drilling.

The next step is to insert the cannulated femoral head extractor 200 in the femoral head from the middle incision MI. When reaching the cancellous bone of the femoral head, as the bone becomes harder on approaching the subchondral bone, greater grip is achieved, with the rotations of the cannulated extractor 200. The second wire 102' if used prevents the rotation of the head within the acetabulum when inserting the cannulated extractor 200. The surgeon may increase the grip on the femoral or humeral head, in addition to that provided by the external screw thread 216 of the cannulated head extractor 200 being received in the drilled opening lateral cortical bone of the femur, by opening the retractable claws 240, which also prevents relative rotation.

Once the head extractor 200 is secured to the femoral head, an opening must be made in the upper area of the articular capsule of the hip using a scalpel introduced from the upper incision UI. Then the Kirschner wires 102, 102' are removed. Next, with the help of the cannulated femoral head extractor 200 the femoral head is rotated in the acetabulum until the femoral head is detached from the ligamentum teres. Then the femur is abducted and the femoral head is then dislocated by the upper portion of the joint through the opening already made in the upper area of the articular capsule (FIG. 12Hi). Once dislocated, the femoral head must be held with a forceps (e.g. Kocher forceps) introduced from the upper incision UI (FIG. 12Hii) and with counter-rotation of the holder 204 the retractable claws are retracted inwardly and the cannulated extractor 200 can be removed through the middle incision MI (FIG. 12Hiii). Then the femoral head is extracted using the forceps through the upper incision UI (FIG. 12Hiv).

Using this femoral head removal technique, the integrity of the articular capsule and of the acetabular labrum is preserved. This means that the hip retains its own stabilizing elements, providing the device with the correct stability and preventing dislocations. It also requires a smaller incision and less soft tissue dissection compared with any other prosthesis approach (hip arthroplasty), which therefore reduces bleeding during surgery.

Next, the head component 1 may be positioned in the patient using the head component insertion device 300, on which the head component will be mounted.

The head component insertion device 300 is shown assembled in FIG. 24A, and various views of the component parts are shown in FIG. 24B through FIG. 26D. The head component insertion device 300 may be formed to include a handle guide 301, a first prong 302A and a second prong 302B, and an actuation member 303. Each of the prongs 302A/302B may be movably mounted to the handle guide 301, and the actuation member 303 may also moveably mounted to the handle guide 301, such that movement of the actuation member in first and second directions causes the prongs 302A/302B to respectively move in first and second directions, permitting engagement and disengagement with respect to the head component 1. In one embodiment, the pair of prongs 302A/302B may be pivotally coupled to the handle guide 301, and the actuation member 303 may have external threading 303T that may rotatably engage internal threading 301T of the handle guide, to rotatably mount the actuation member to the handle guide. As such, in this embodiment, rotation of the actuation member 303 in a first rotation direction (e.g., clockwise) causes the pair of prongs 302A/302B to move apart for the distal ends to be able to engage the pair of recesses 14A/14B in the head component 1; and rotation of the actuation member 303 in a second rotation direction (i.e., counterclockwise) causes the pair of prongs 302A/302B to move towards each other to be able to disengage the distal ends from the pair of particularly shaped recesses 14A/14B in the prosthetic head 1. In this embodiment, the prongs 302A/302B may be spring biased towards each other, so that rotation of the actuation member 303 may cause contact between at least a portion of its tip 303P (FIG. 26C) and cam shaped portions of the prongs, causing them to be driven apart to become engaged within the recesses of the head component 1. In another embodiment, as seen at least in FIGS. 28E and 28F, the prongs may each be cantilevered from the handle guide 301, and inserting and rotating the actuation member 303 so that its external threading 303T rotatably engages the internal threading 301T of the handle guide may drive a portion of the tip 303P of the actuation member between the prongs, causing the prongs to elastically deform outwardly (FIG. 28F) for engagement of a portion of the tip of the prongs within the recesses 14A/14B of the head component 1.

The profiled shape of the ends of the prongs 302A/302B are formed to correspond to the profile shape of the recesses in the head component 1 (see FIG. 2A). Where the profile shape of the recesses in the head component 1 are rectangular, the profiled shape of the ends of the prongs 302A/302B may be rectangular, and may be slightly smaller so as to be received in the recesses in a clearance fit, and the actuator 303 may drive the sides of the prongs into engagement with the sides of the recesses, creating a frictional engagement therebetween. Where the profile shape of the recesses in the head component 1 are trapezoidal, as shown in FIG. 2A, the profiled shape of the ends of the prongs 302A/302B may be correspondingly shaped to have the exterior side be at an angle, which may become engaged with the angles side of the trapezoidal recess, when the actuator 303 may drive the sides of the prongs outwardly (see FIGS. 27B and 27C). Other shapes for the recesses and prongs may be used. For example, the recess may be stepped, and the prong may have a lateral protrusion configured to be received within the stepped recess.

The handle guide 301, may be formed to include a graspable handle on at least a portion of the U-shaped body. The U-shaped body (and/or a portion of the graspable handle) may include an opening configured to guide the metaphyseal component insertion device 400. The opening may simply be a hole of a suitable diameter (e.g., diameter $D_H$ shown in FIG. 25G) that is oriented at the proper angle, and which may be substantially centered with respect to a mid-plane of the U-shaped body, being configured to align the metaphyseal component insertion device 400 with the bore in the head component 1. Alternatively, the handle guide 301 may have opening 347 and an opening to form surface 346A and 346B that may be formed the same as the first opening 147 and second opening forming the parallel surfaces 146A and 146B of the multi-function handle guide 140, as may be seen in comparing in FIGS. 25D-25E to FIGS. 13D-13E.

The metaphyseal component insertion device 400, as shown in FIGS. 29A-29K, can be used to secure the metaphyseal component 2 to the head component 1. The metaphyseal component insertion device 400 may include a hollow outer tubular body 401 (FIGS. 31A-31F), and an inner cylindrical body 402 (FIGS. 32A-32G) that may be received in the hollow outer tubular body 401 and be coaxial therewith, which coupling therebetween may be controlled by a nut 407 and a flanged washer 408 (which nut may act as a jam nut when the outer tubular body 401 is formed with internal threading to which the external threading 402T on the inner tubular body 402 may be threadably coupled thereto). A first end 401A of the outer tubular body 401 and one end of the metaphyseal component 2 may be formed to releasably couple to each other in any suitable manner, and in one embodiment, a bayonet mounting arrangement may be used for attachment of the metaphyseal component 2 to that end of the tubular body. The bayonet arrangement may include L-shaped protrusions 403 that extend from a flange 401F (FIG. 31C) with an opening 401P formed on the first end 401A of the outer tubular body 401. Each L-shaped protrusion 403 may be received in a corresponding recess in the second end of the metaphyseal component 2, which recess may be formed to have a slotted recess portion 27S and an annular recess portion 27A (see FIG. 5C). Note the annular flange 401F at the first end 401A of the outer tubular body 401 may act as a stop to limit axial travel of the inner tubular body 402 when inserted therein: as such, any shape other than the annular flange (e.g., a simple protrusion) may similarly be utilized to act as a stop to limit such travel.

The inner tubular body 402 may be formed to have one or two projections 405 on one end, which are shaped and positioned to enter the corresponding notches 25 in the second end of metaphyseal component 2 (FIG. 5D), while the opposite end of the inner body may be formed with a gripper handle 404. (Note, the inner body 402 may also be tubular, being formed with the central orifice 402F shown in FIG. 32D configured in terms of its size and position for the passage of the locking device 24 and of a corresponding tool used to secure the locking device to the metaphyseal component, as discussed hereinafter and shown in FIGS. 12P-12R).

To releasable couple the metaphyseal component insertion device 400 to the metaphyseal component 2, the metaphyseal component insertion device 400 is axially aligned with the metaphyseal component 2 and moved axially into engagement therewith, whereby the protrusions 403 on the outer tubular body 401 (FIG. 31F) are first received in the corresponding slotted recess portions 27S of the metaphyseal component (see FIG. 5F), and the two projections 405 on the inner tubular body 402 are simultaneously received in the corresponding notches 25 of the metaphyseal component; then the inner tubular body 402 may then be held static while the outer tubular body 401 may be rotated (e.g., clockwise) to cause the L-shaped protrusions 406 of the outer tubular body 401 to rotate into the annular recess portions 27A of the metaphyseal component 2.

The threaded nut 407 rotatably positioned on the inner tubular body 402 close to the gripper 404 can inhibit the relative movement between the coaxial bodies 401, 402, upon tightening of the nut 407 against a flanged washer 408 that protrudes from the end of the outer tubular body 401, which can slide relative to the bodies 401, 402, but which cannot rotate relative to the inner tubular body 402, because of the engagement of the tab 408T of the flanged washer 408 (FIG. 33B) within the axial slot 402S (FIG. 32B) that is formed transverse to the external threading 402T of the inner tubular body 402. (See FIG. 29J, and FIGS. 29G-29I). The closeness of the nut 407 to the flanged washer 408 prevents the outer tubular body 401 from rotating, once the flange 408F of the washer (FIG. 33B) has been slid into the recess 401R at the second end 401B of the outer tubular body (FIG. 31B), and the nut 407 has been threaded into contact with the flanged washer (compare the positioning of the flanged washer 408 and the nut 407 as seen within FIGS. 29G, 29H, and FIG. 29I).

Thereafter, with the metaphyseal component 2 releasably secured to the outer tubular body 401, when both bodies 401, 402 are rotated together, such rotation causes the metaphyseal component 2 to rotate as well.

Figure 12M:
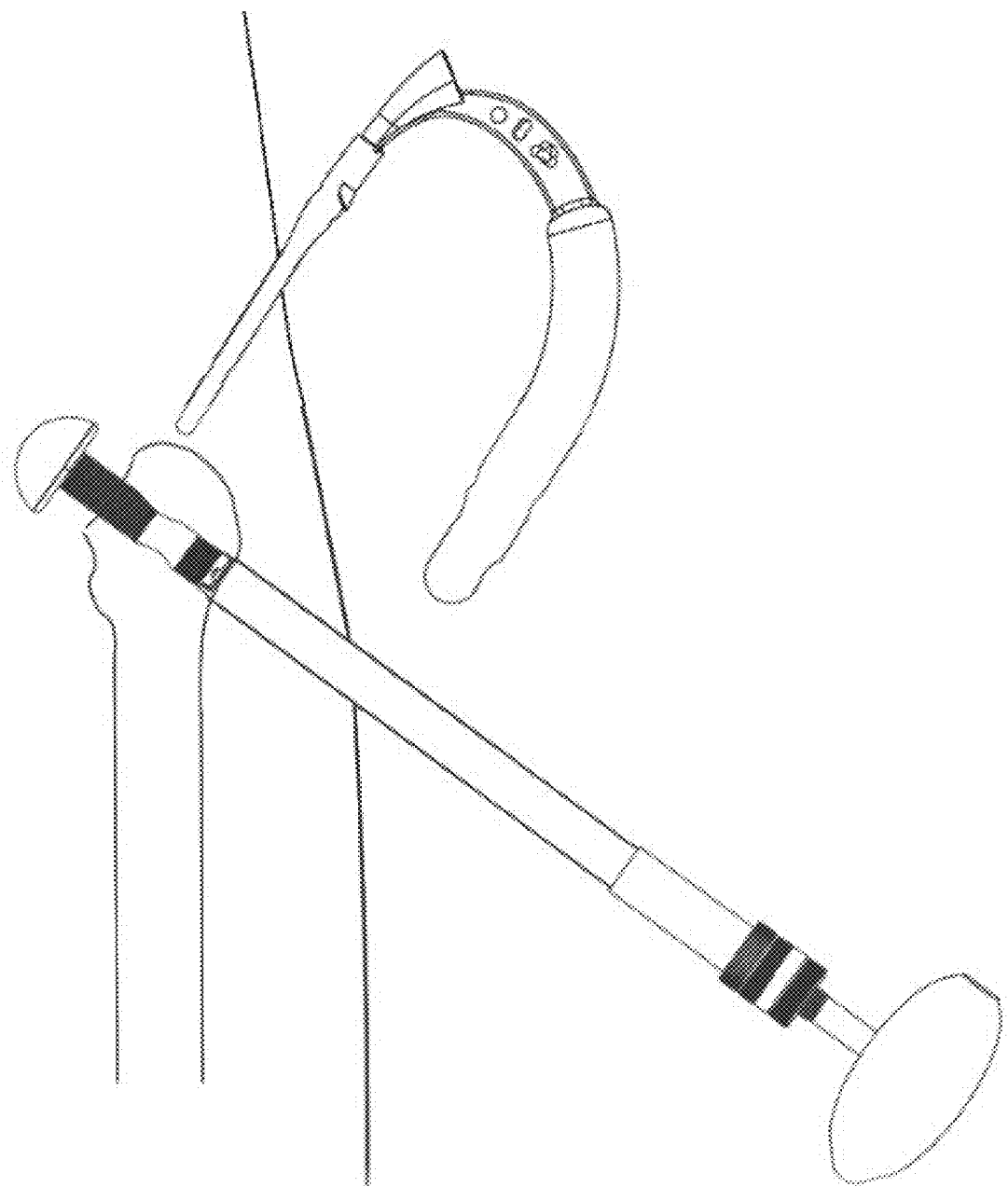
FIG. 12M is the front view of FIG. 12L, but showing the Diaphyseal Nail releasably coupled to the Handle Guide, and initially being introduced through the upper incision.
Figure 12N:
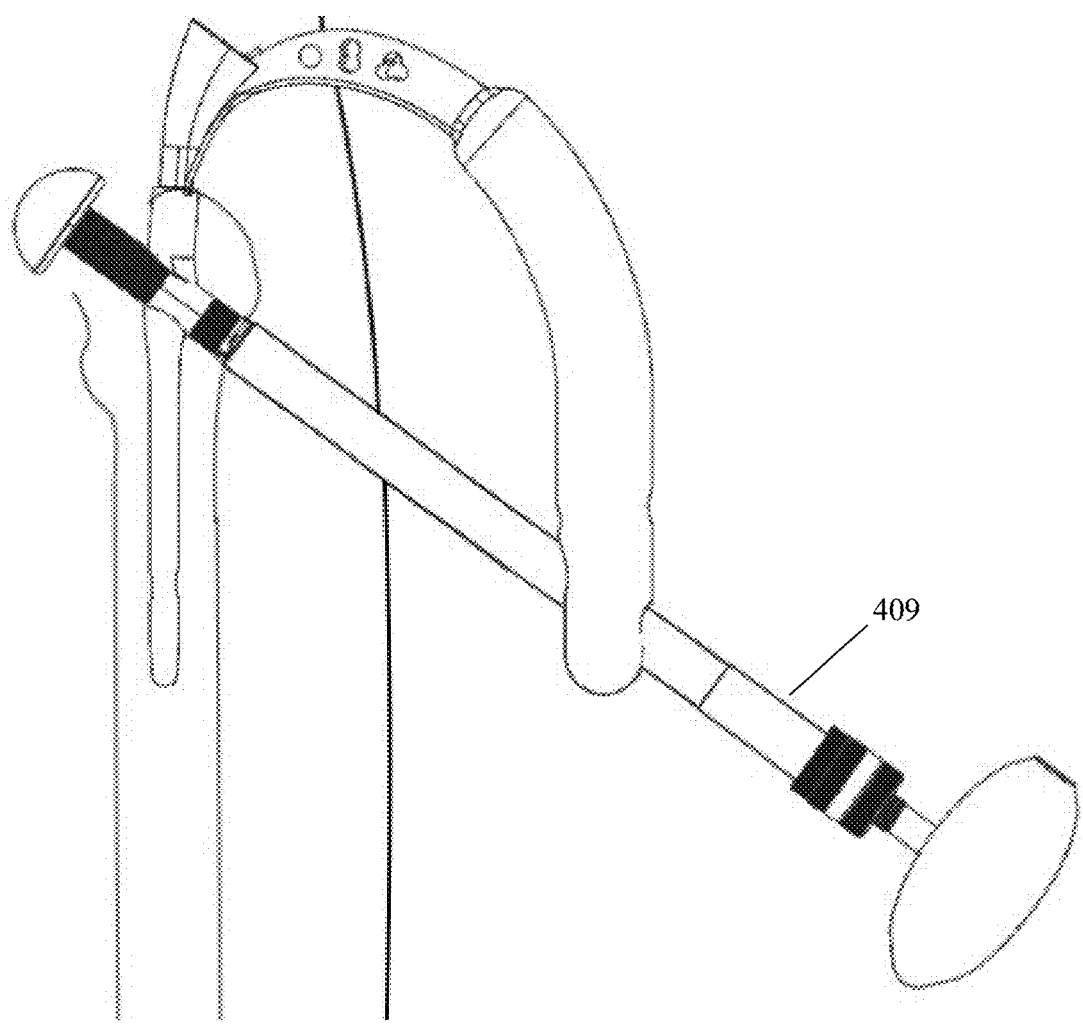
FIG. 12N is the front view of FIG. 12M, but shown after the distal end of the Diaphyseal Nail has been inserted through the tip of the greater trochanter of the femur, and through the transverse aperture of the Metaphyseal component, with the body of the nail placed into the femoral canal.
Figure 12P:
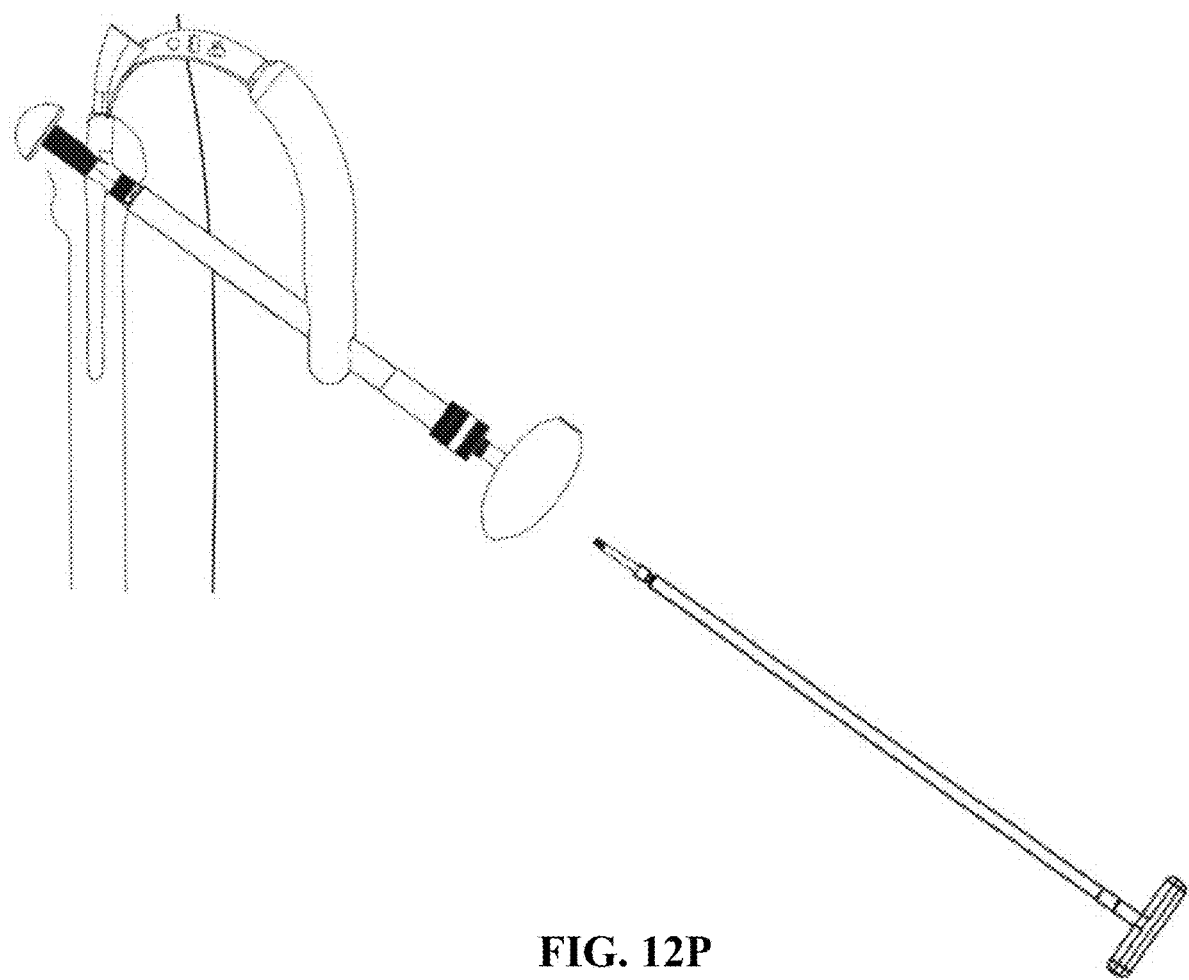
FIG. 12P is the front view of FIG. 12N, but shown after the Locking Device is releasably coupled to the Locking Device Screw Driver, just prior to being introduced into the Metaphyseal Component Insertion Device.

As seen in FIG. 12Ji, the surgeon may insert the metaphyseal component 2 through the middle incision MI while it is so mounted to the metaphyseal component insertion device 400, and may rotate both bodies 401, 402 together to fasten the externally threaded shank portion 22 of the metaphyseal component 2 to the internally threaded bore 13 of the head component 1. Note that an indicator (e.g., a marking) on the metaphyseal component insertion device 400 that is coordinated with (i.e., clocked with respect to) the bayonet mounting, may indicate to the surgeon when the metaphyseal component 2 is correctly positioned for its aperture 21 to be able to receive the diaphyseal nail 3 therethrough, as shown in FIGS. 12M-12N.

Subsequently, the inner tubular body 402 may be held static while the threaded nut 407 is counter-rotated and the flange washer 408 moved backwards allowing relative rotations between both tubular bodies. Then, the L-shaped protrusions 406 of the outer tubular body 401 may be disengaged from the annular recess portions 27A. Thereafter, the metaphyseal component insertion device 400 may be backed away from the metaphyseal component 2, removing the protrusions 406 from the slotted recess portion 27S and removing the projections 405 from the corresponding notches 25.

To facilitate stable positioning of the metaphyseal component insertion device 400 during installation of the metaphyseal component 2, a sleeve 409 (FIGS. 35A-35C) may be slidably received over the outer tubular body 401 (see FIG. 29). The outer diameter D1 (FIG. 30) of the outer tubular body 401 may be small enough to slide between the parallel surfaces 346A and 346B and also freely slide laterally into the opening 347. However, the diameter D2 of the sleeve 409 may be too large to slide between the parallel surfaces 346A and 346B, and may be sized to only permit it, when slid along the outer tubular body 401 (compare the sleeve positions in FIGS. 12N and 12K), to be slidably received in the opening 347 in a small clearance fit or a slight friction fit. This engagement between the sleeve 409 and the opening 347 in the handle guide 301 may serve to properly position the angular position of the metaphyseal component insertion device 400, and properly guide the introduction of the metaphyseal component 2 with perfect alignment into the bore 13 (FIGS. 12Ji-12K).

Once the head component 1 is fastened to the metaphyseal component 2, the sleeve 409 may be slid away from the handle guide 301, and the head component insertion device 300 can be removed, leaving the arrangement shown in FIG. 12L (i.e., with the metaphyseal component insertion device 400 still coupled to the metaphyseal component 2).

Next, the diaphyseal nail 3 may be positioned using a diaphyseal nail insertion device 500, which is shown in FIG. 36A-36F. As may be seen in the exploded view of FIG. 37, the diaphyseal nail insertion device 500 may be the assembly of a handle guide, and a releasably coupling arrangement for coupling of the diaphyseal nail 3 to the handle guide (e.g., the threaded arrangement that uses bolt 107).

The handle guide used for the diaphyseal nail insertion device 500 may be identical to the handle guide 140 used for the Kirschner wire centering device 100; or more aptly stated, because the handle guide used for the diaphyseal nail insertion device 500 ultimately requires use of the hole 148 whereas that hole is not utilized for the Kirschner wire centering device 100, the Kirschner wire centering device 100 may use the same handle guide as is used for the diaphyseal nail insertion device 500. Also, the first opening 147 and second opening that forms surfaces 146A and 146B in the handle guide of the Kirschner wire centering device 100 to receive the sleeve 103 (FIG. 12Aii-12B) need not utilize the same cross-sectional shape as the openings in the handle guide of the diaphyseal nail insertion device 500, which accommodate the metaphyseal component insertion device 400 the same as the handle guide 301 for the head component insertion device 300. However, such commonality may be advantageous, and for ease of discussion herein, the same handle guide 140 is described as being utilized for both the Kirschner wire centering device 100 and the diaphyseal nail insertion device 500, with the understanding that they may be different handle guides, and that the openings are the same for the handle guides 140 and 301.

Since the first opening 147 and second opening that forms surfaces 146A and 146B in the handle guide 140 are the same as the opening 347 and the opening that form surface 346A and 346B in the head component insertion device 300, the diaphyseal nail insertion device 500 may be used to place the diaphyseal nail 3, as shown in FIGS. 12M to 12N, and also have the sleeve 409 of the metaphyseal component insertion device 400 thereafter slide into engagement within the hole 147.

The diaphyseal nail 3 is then inserted through the upper incision UI, using the diaphyseal nail insertion device 500, and passes through the aperture 21 of the metaphyseal component 2, until the diaphyseal nail 3 is engaged therewith (e.g., in a slight friction fit) because of the size of its second portion 33 being particularly formed in relation to that of the aperture 21, and may be further limited as to such relative movement if the diaphyseal nail 3 is configured to include the protruding stop 34.

Figure 12Q:
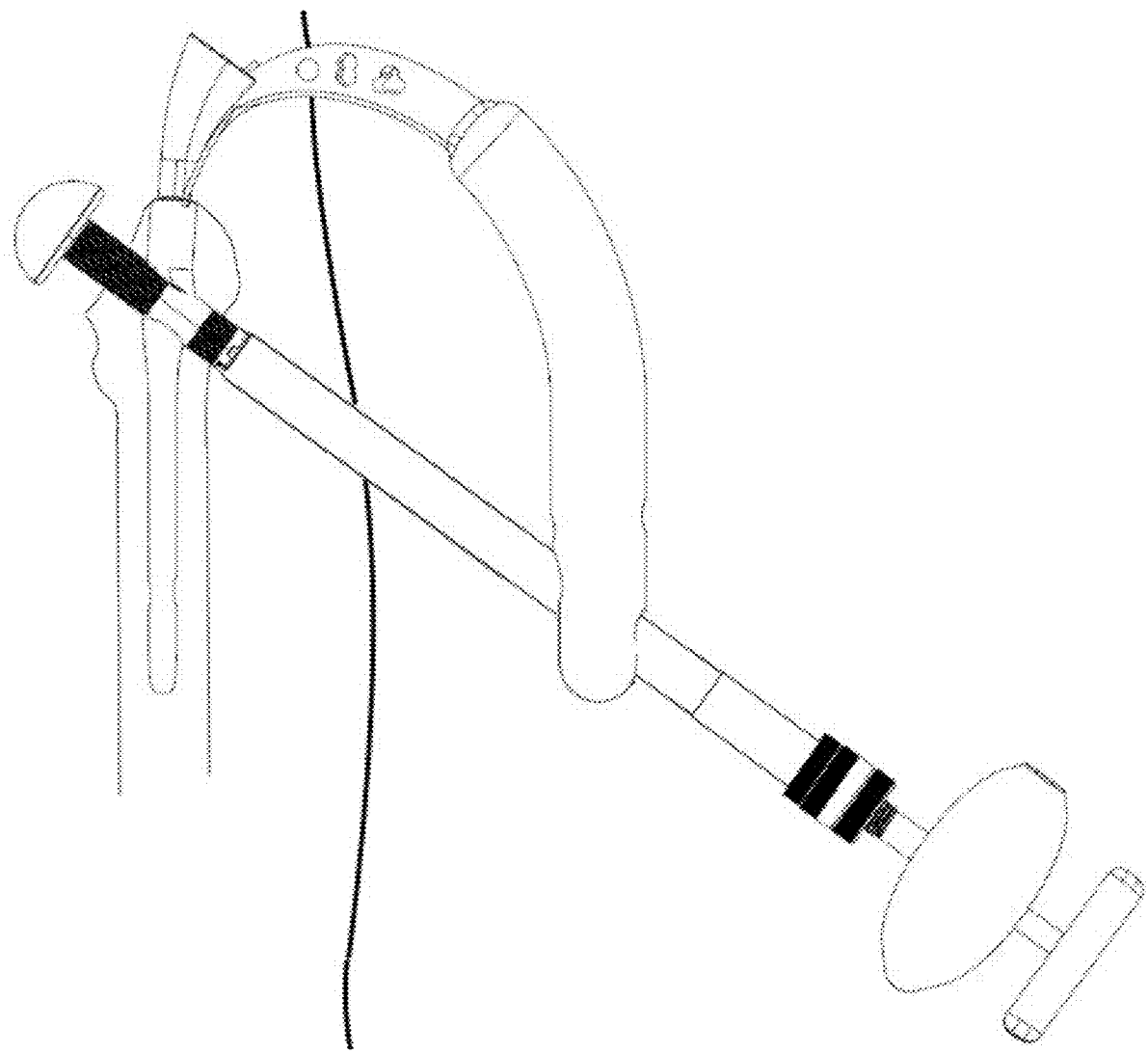
FIG. 12Q is the front view of FIG. 12P, but shown after the Locking Device Screw Driver has been used in combination with the Metaphyseal Component Insertion Device to secure the Locking Screw to the Metaphyseal Component.
Figure 12R:
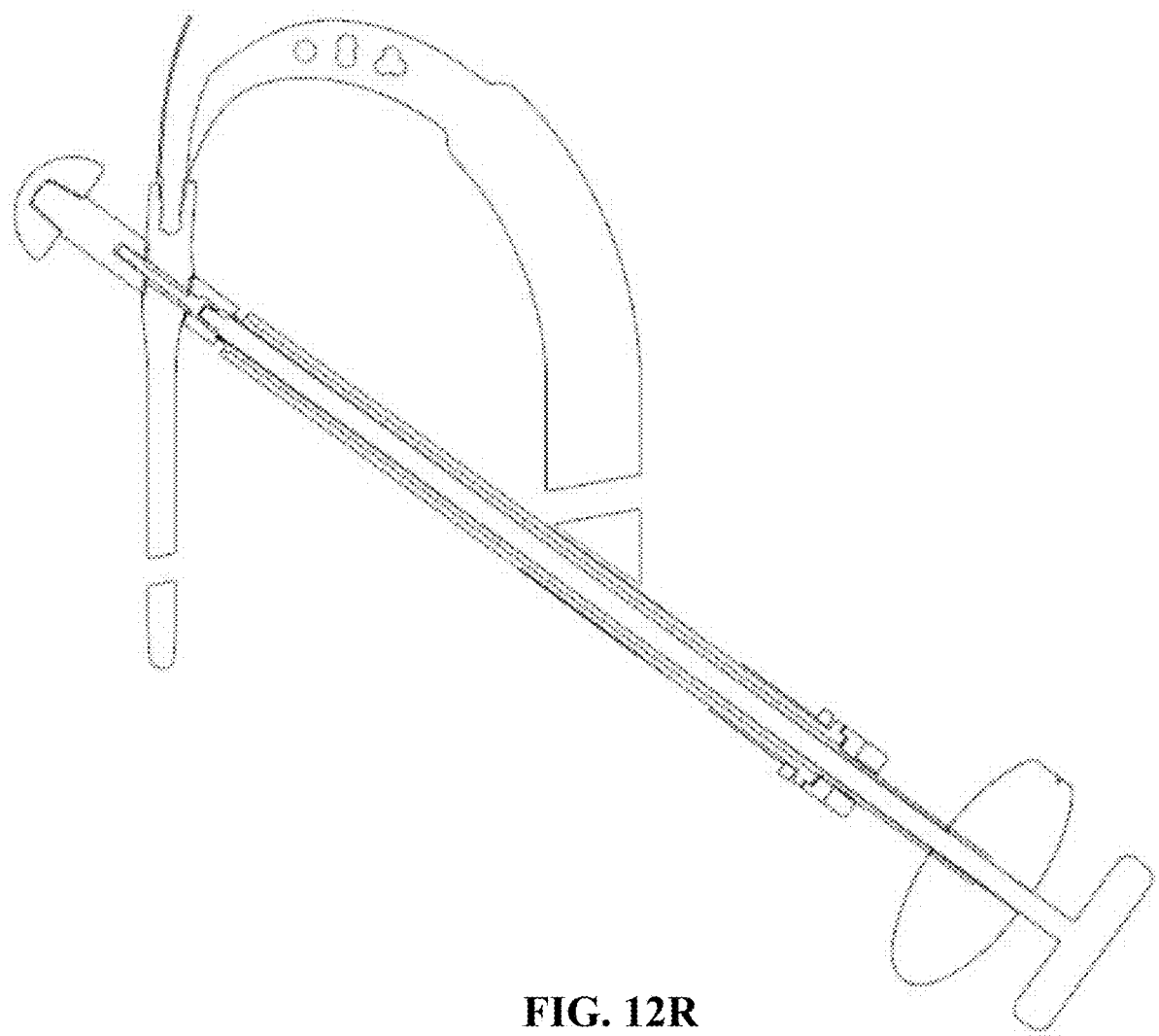
FIG. 12R is a cross-sectional view through the arrangement shown in FIG. 12Q.

Next, the locking device 24 (FIG. 7A) may be installed to secure the diaphyseal nail 3 to the metaphyseal component 2. The locking device 24 may be installed using any suitable device, including, but not limited to, an ordinary screwdriver, where the head of the locking device may have a slotted or Philips head formed thereon. In one embodiment, the locking device 24 may be formed to be installed using the torqueing device 600 shown in FIGS. 38A-38D. The torqueing device 600 may have a rod 601 that may be formed to be slidably received in the central orifice 402F of the inner tubular body 402 of the metaphyseal component insertion device 400 (FIG. 32D). One end of the rod 601 may be formed to have a handle 602, while the other end may be formed to have a shaped engagement protrusion 603. The shaped engagement protrusion 603 may be any suitable protrusion, including but not limited to, a blade, a cruciform, and Allen key, etc. The head of the locking device 24 may be formed to have a recess that corresponds to the shaped engagement protrusion 603. The locking device 24 may be mounted onto the shaped engagement protrusion 603 of the torqueing device 600 (FIG. 12P), both of which may then be inserted into the inner tubular body 402 of the metaphyseal component insertion device 400, and the handle 602 may be rotated to threadably secure the external threads of the locking device with respect to the internal threading of the metaphyseal component 2 (FIGS. 12Q-12R). The torqueing device 600 with the locking device 24 placed thereon may be pre-installed in the metaphyseal component insertion device 400.

Figure 12S:
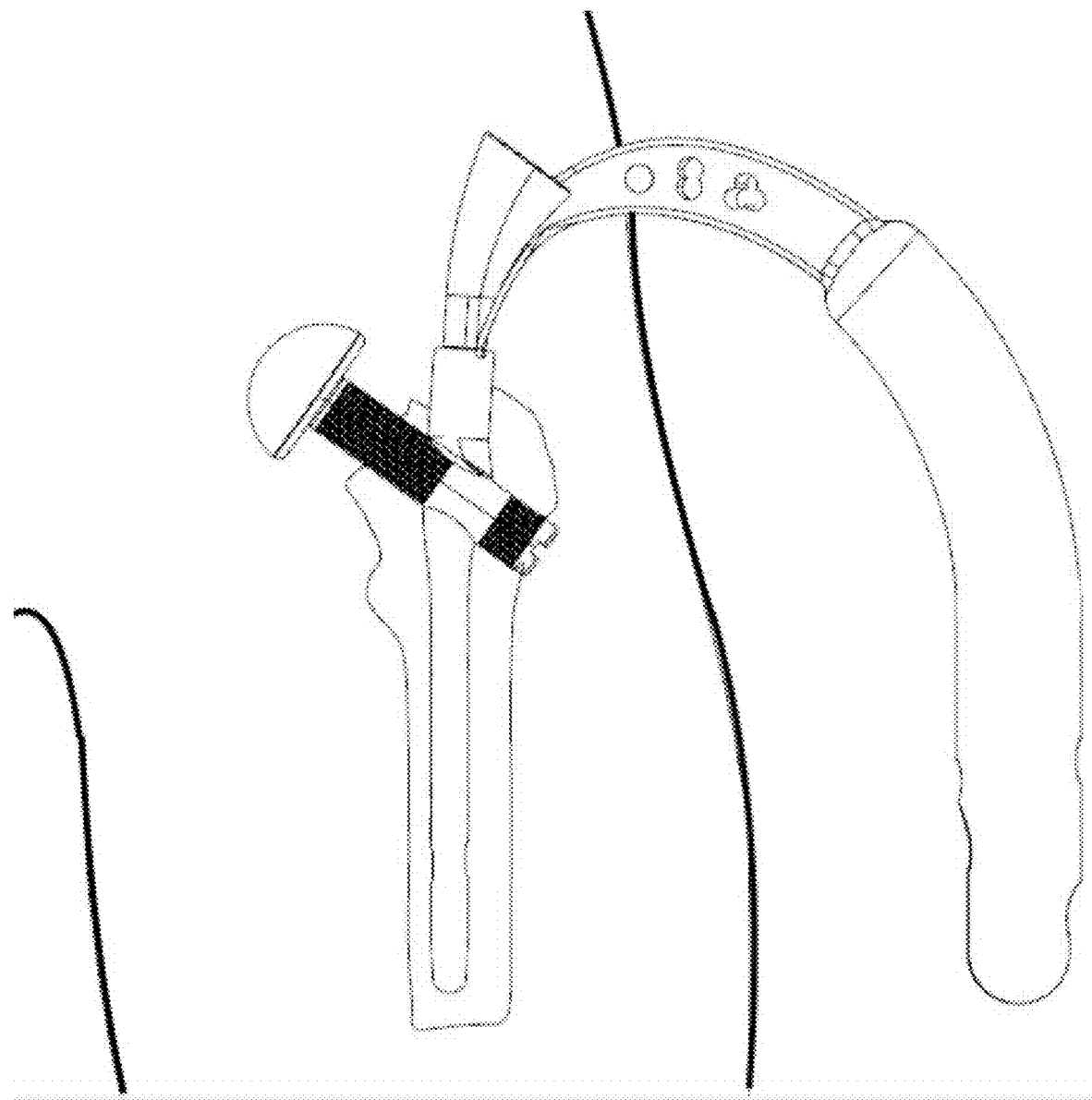
FIG. 12S is the front view of FIG. 12R, but shown after the Metaphyseal Component Insertion Device and the Locking Device Screw Driver have been removed from the Handle Guide.
Figure 12T:
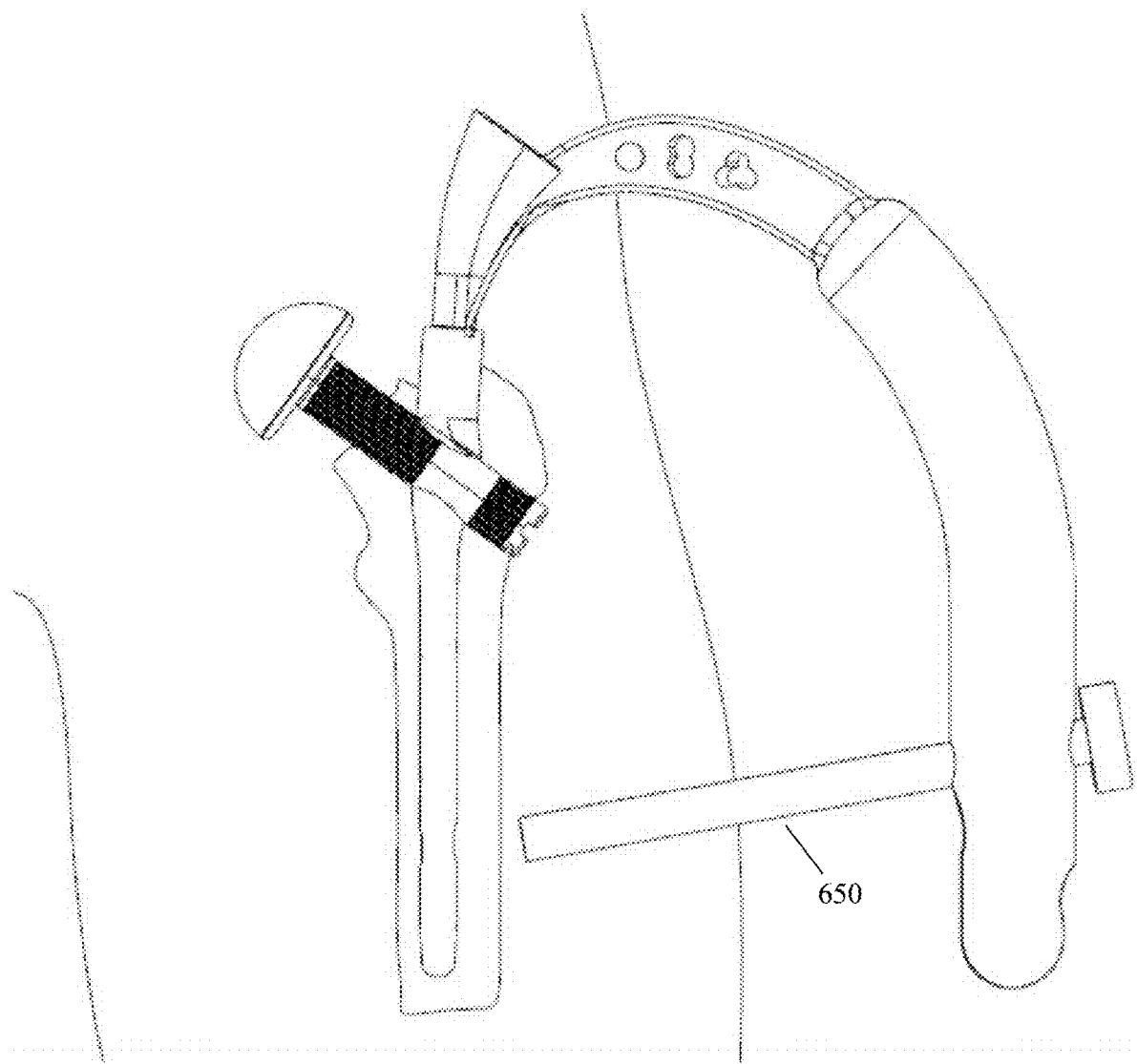
FIG. 12T is the front view of FIG. 12S, but shown after a Screw Sleeve has been used in combination with the Handle Guide to drive a hole in the femur that is used to receive a screw.
Figure 12U:
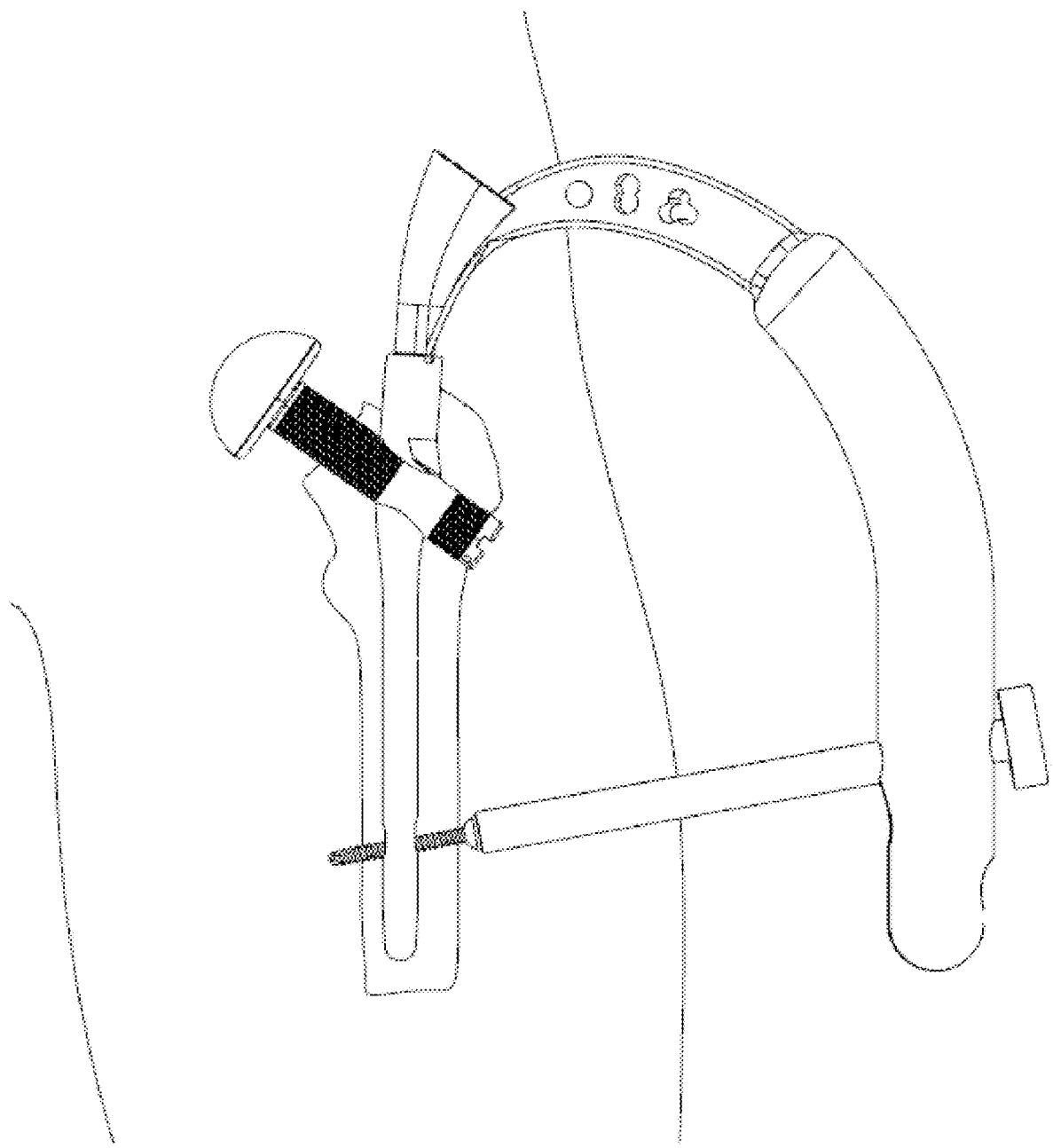
FIG. 12U is the front view of FIG. 12T, but shown after the Screw Sleeve has been used in combination with the Handle Guide to install a Screw to secure the Diaphyseal Nail to the femur.
Figure 12V:
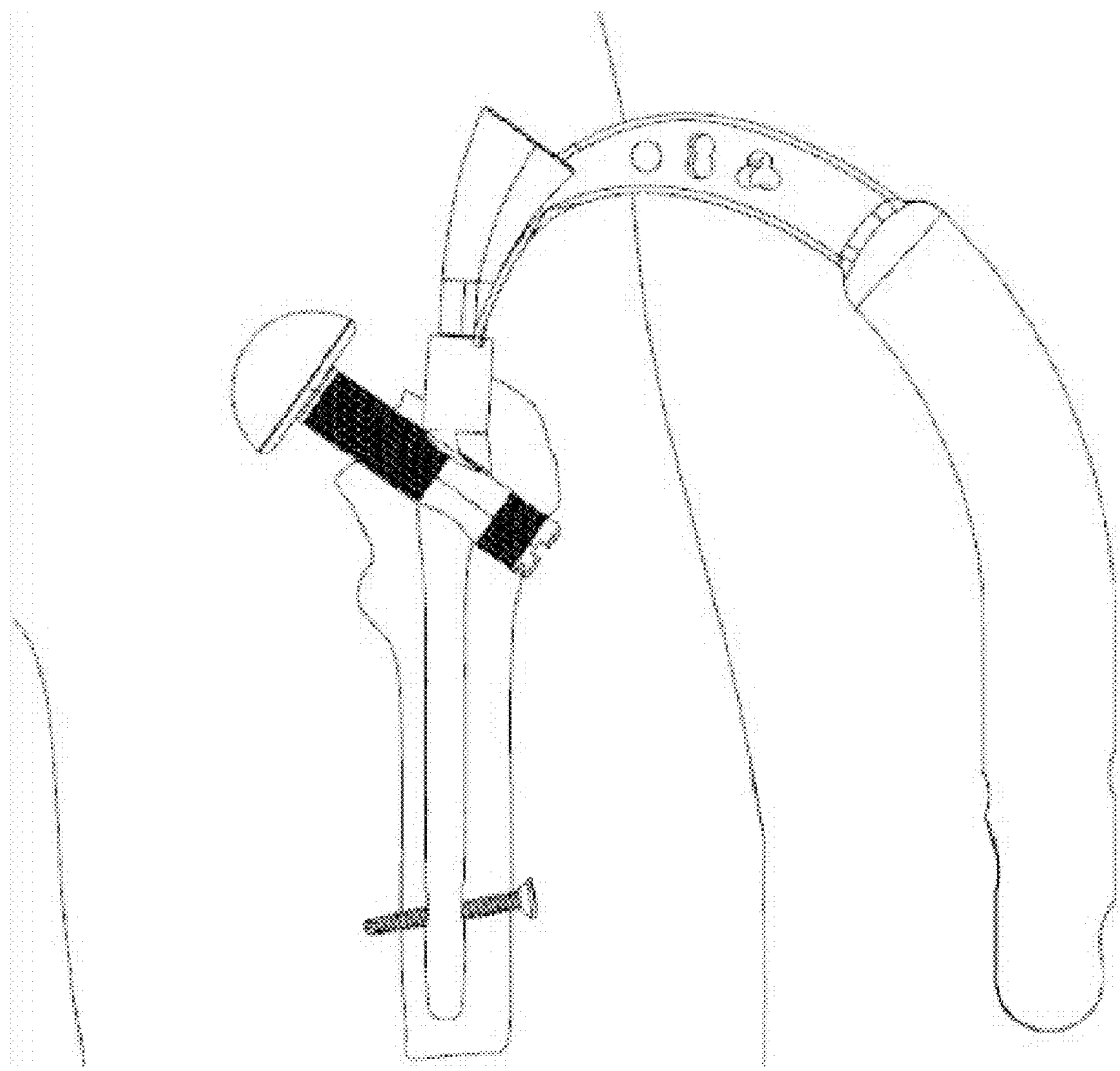
FIG. 12V is the front view of FIG. 12U, but shown after the Screw Sleeve has been withdrawn from the opening in the Handle Guide.
Figure 12W:
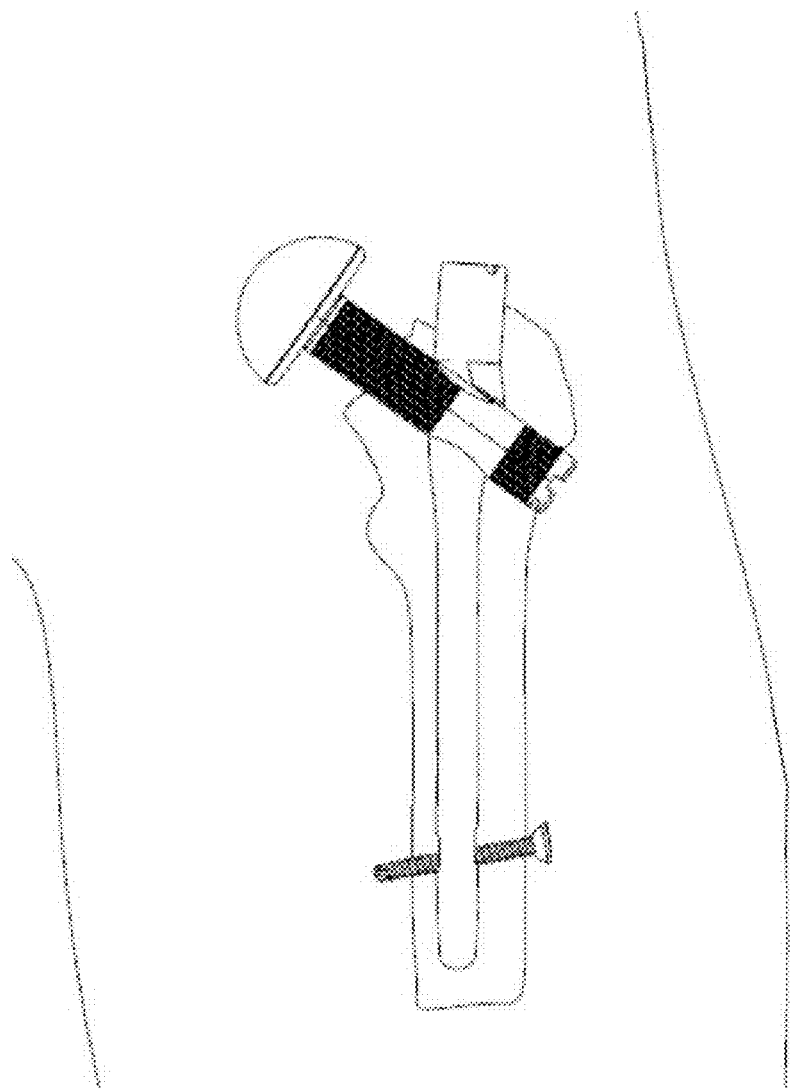
FIG. 12W is the front view of FIG. 12V, but shown after the Handle Guide has been detached from the Diaphyseal Nail and withdrawn out of the upper incision.
Figure 13A:
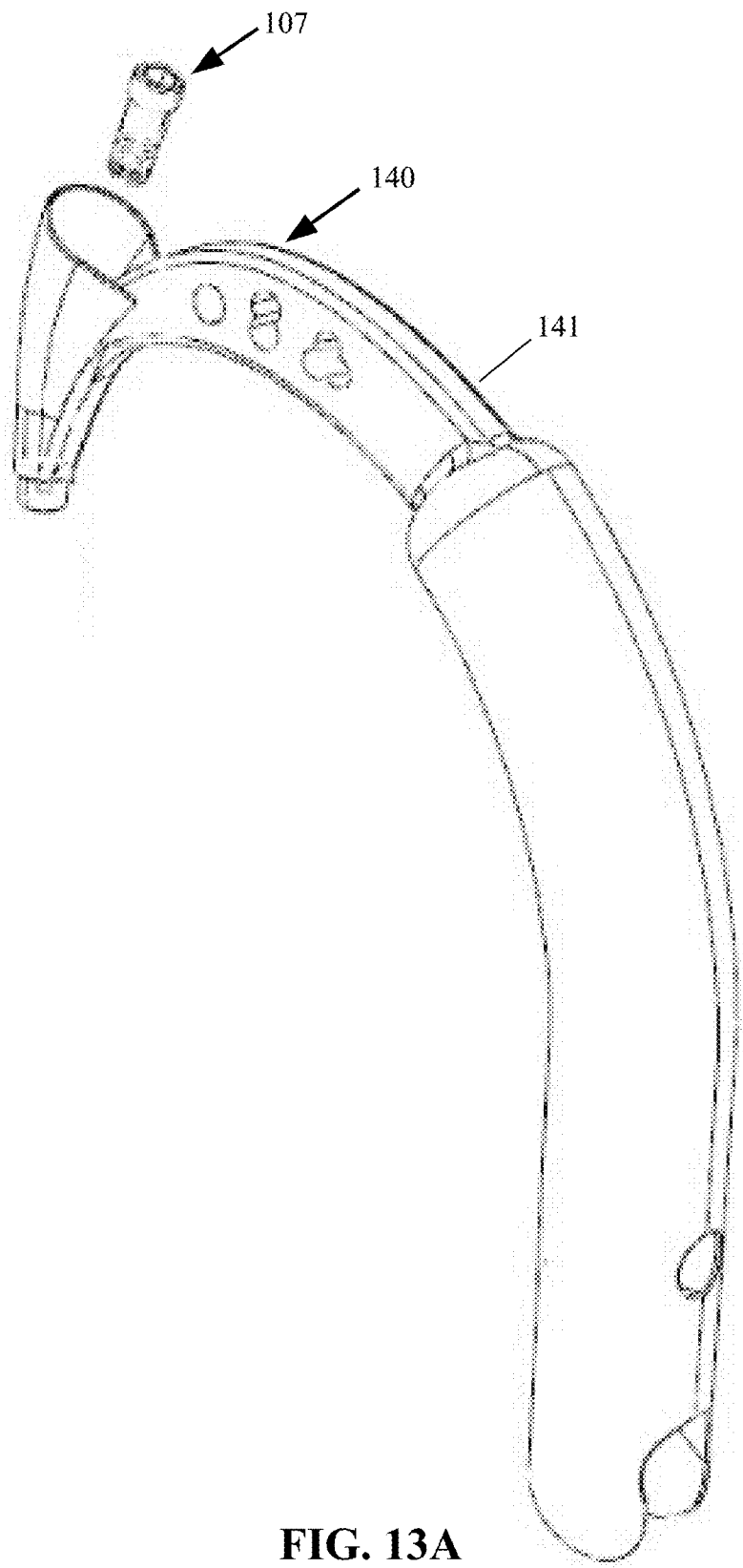
FIG. 13A is a perspective view of a multifunction handle guide, usable with other different pieces of equipment for completing different aspects of placing the prosthesis, including: use in placing a centering nail as seen in FIGS. 12Ai-12Aii, and in combination with the centering nail for placing one or more Kirschner wires as seen in FIGS. 12Aiii-12Ei; use in placing the diaphyseal nail as seen in FIGS. 12M-12N, and in combination with the Diaphyseal Nail and the Metaphyseal Component Insertion Device and the Locking Device Screw Driver for placing the Locking Device as shown in FIGS. 12P-12S; and use in combination with the diaphyseal nail and a Sleeve for placing one or more screws for fastening the diaphyseal nail to the femur or humerus as seen in FIGS. 12U-12W.
Figure 13B:
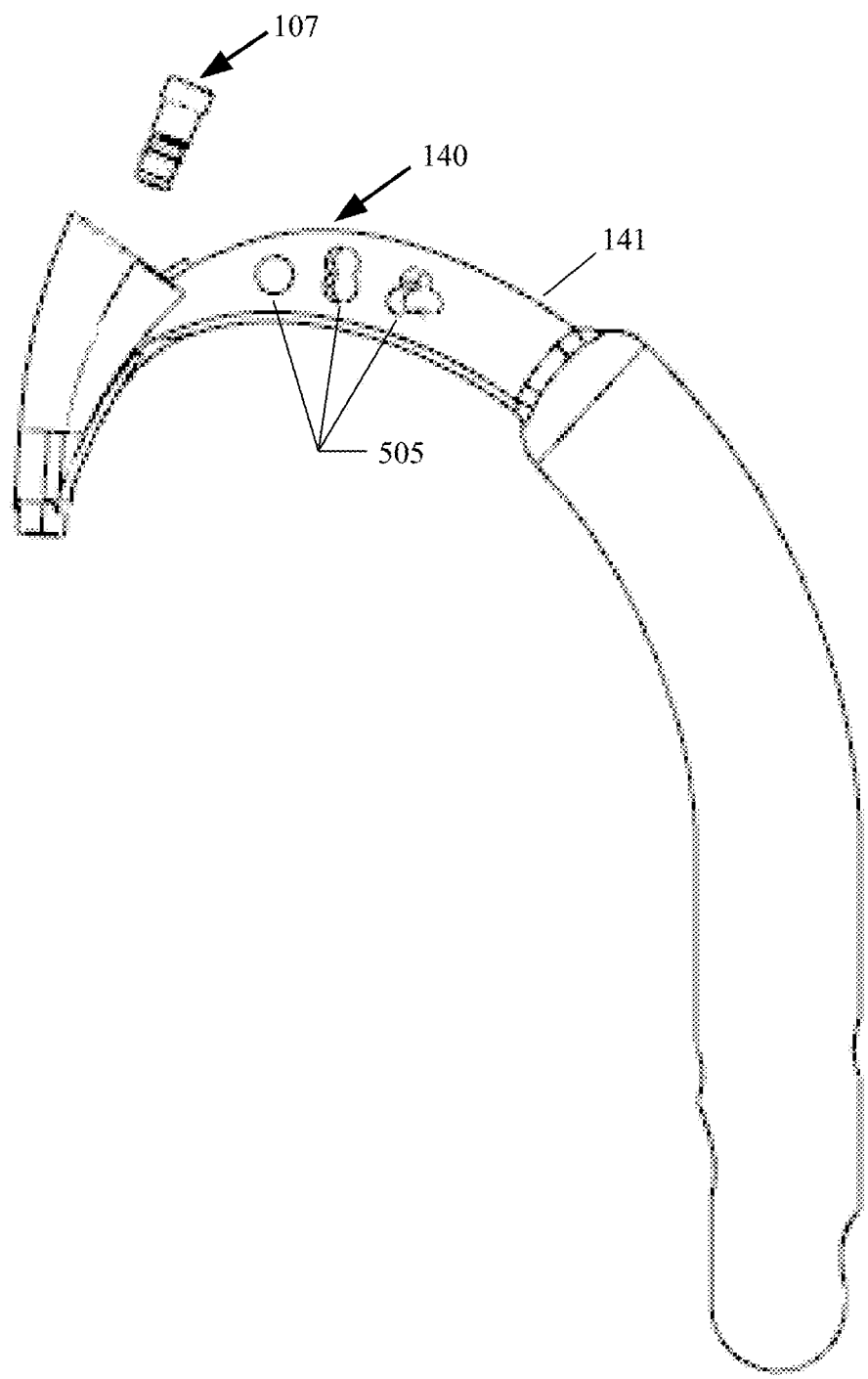
FIG. 13B is a side view of the prosthesis placement apparatus of FIG. 13A.

Once the locking device 24 is threadably engaged within the first section of the metaphyseal component 2, the metaphyseal component insertion device 400 is disconnected from the metaphyseal component 2 (see FIG. 12S). At that moment the anteversion of the hip arthroplasty device relative to the femur is selected.

The U-shaped body of the handle-guide 140 (and also the handle guide 301) may have series of orientation marks 505 which allow the surgeon to ascertain the angular orientation (anteversion) of the diaphyseal nail insertion device 500 and/or the Kirschner wire centering device 100 and the head component insertion device 300. The series of marks may consist of objects (apertures, inserts, etc.) with a transparency to X-rays that is different from that of the rest of the instrument. Each object will have a different angle ("0°, 8° and 16°;" "0°, 10° and 20°;" "0°, 5°, 10° and 15°"', etc.). As may be seen in FIG. 13B, each orientation may be uniquely shaped to provide for easier identification on the image intensifier. With the orientation marks 505 shown in the figures, one first mark that is cylindrical creates two circular edges which when aligned while viewed on the image intensifier indicate 0° of anteversion; a second mark formed as two intersecting cylinders creates two sets of marks being circle portions which when aligned indicates 10° of anteversion; and a third mark formed as three intersecting cylinders three created three sets of marks being circle portion which when aligned indicates 20° of anteversion (see FIG. 13F). Other shapes to create different marks or openings may alternatively be used; however, the circular shapes are very visible and useful to the surgeon. The chosen anteversion is preferable between 15-20 degrees.

Thus, when the surgeon uses the image intensifier, the one of the three marks 505 that is not deformed (i.e., the one that appears to be in plane) will indicate the angle of anteversion applied relative to the femur. FIG. 12 has been produced with an angle corresponding to the first mark 505, and therefore the mark is not angled (out of plane), but the others are.

Once the anteversion has been selected, the diaphyseal nail 3 may be fastened to the femur by positioning the distal screws 31S. In the lower portion of the diaphyseal nail 3 one or more distal screws are arranged in each fastening aperture 37. This insertion may be by any known method of the prior art, whether through the lower incision or through the middle incision MI, depending on the position or orientation of the fastening apertures 32. The distal screws 31S may be installed using the screw sleeve 650 shown in FIGS. 12T-12U, which screw sleeve may be received in the hole 148. The screw sleeve 650 may be a hollow cylinder that can be used to guide the drill bit while drilling a hole in the femur, and may support and guide a screwdriver while introducing the screw with the screwdriver. In one method, two different sized concentric sleeves may be used while blocking femoral nails: the first one (smaller) may be placed inside the second one (bigger). So, the drill introduces the drill bit through the small sleeve, and once the femur is drilled the small sleeve is removed, leaving the bigger sleeve, which is used to introduce and guide the screw with the screwdriver. The sleeve(s) is/are not only used to guide the drill and screwdriver, but also protect the surrounding soil tissue.

Once this has been done, the diaphyseal nail insertion device 500 is withdrawn, leaving the hip arthroplasty device now placed in its final position.

The invention therefore comprises, in addition to the prosthesis, an entire series of preferred instruments which are designed to assist in its positioning and to remove the femoral head:

a Kirschner wire centering device 100;
a cannulated femoral or humeral head extractor 200;
a head component insertion device 300;
a metaphyseal component insertion device 400;
a diaphyseal nail insertion device 500.

It can be seen that the first two insertion devices 300, 400 serve as guide for the insertion of the next insertion device. In other words, the head component insertion device 300 serves as a guide for inserting the metaphyseal component insertion device 400, and this in turn serves as a guide for inserting the diaphyseal nail insertion device 500 (FIG. 10), thus minimizing error and facilitating manipulation by the surgeon.

However, other different instruments may be used which would allow the prosthesis to be assembled at the site of use, but without facilitating the work of the surgeon, for example, always using straight insertion devices.

Moreover, the transmission of the load from the prosthesis to the femur is distributed at various points: the metaphyseal component 2 transmits its load to the calcar, whilst the diaphyseal nail 3 transmits the load to the diaphysis. All this provides sufficient stability and cementing is therefore not mandatory, which avoids the complications of cementing the hip arthroplasty.

However, if cementing is preferred, the metaphyseal component 2 and/or the diaphyseal nail 3 may have a channel to allow the introduction of cement from the outside, once in position, through a cannula, syringe, etc., in order to increase the contact between the different portions of the prosthesis and the femur.

All the materials must be biocompatible, particularly those that remain inside the patient's body.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. An extractor, said extractor configured to assist in removal of a femoral head or a humeral head from a patient's body, said extractor comprising:

a handle member (220);
a cannulated screw member (210); said cannulated screw member comprising:
an outer shaft with a first end and a second end, said first end of said outer shaft having an opening defining a hollow interior cavity; said second end of said outer shaft comprising a plurality of openings interconnected with said hollow interior cavity;
an external screw thread configured to protrude away from a portion of said second end of said outer shaft, said external screw thread configured to be screwed into a bored opening in the femoral or humeral head;
an inner shaft member (230), at least a portion of said inner shaft member comprising external threading; said inner shaft member comprising a slotted opening (235) being elongated parallel to a central axis of said inner shaft member;
a plurality of claws (240), each of said plurality of claws being pivotally attached proximate to a first end of said inner shaft member, being configured to pivot between an extended position where each said claw is angled radially with respect to the central axis of said inner shaft member, and a retracted position where each said claw is oriented substantially parallel to the central axis of said inner shaft member;
an actuation member (250), said actuation member comprising internal threading;
wherein said inner shaft member with said plurality of claws is slidably received in said hollow interior cavity of said cannulated screw member, being slidable therein from a first position where said claws are in said retracted position, and a second position where said claws exit a respective said opening of said plurality of openings at said second end of said outer shaft and are driven into said extended position;
wherein said inner shaft member is rotatably mounted to said actuation member with said internal threading of said actuation member threadably coupled to said external threading of said inner shaft member;
an anti-rotation pin; and
wherein said cannulated screw member is secured to said handle member, with said anti-rotation pin received through said slotted opening in said inner shaft member to inhibit rotation of said inner shaft member.

2. The extractor according to claim 1,
wherein said external screw thread of said cannulated screw member comprises an axial hole formed substantially concentric with a central axis of said outer shaft and being interconnected with said hollow interior cavity;
wherein said inner shaft member comprises an axial hole formed substantially concentric with the central axis of said inner shaft member;
wherein said handle member comprises an axial hole, said axial hole in said handle member being substantially concentric with the central axes of said cannulated screw member and said inner shaft member; and
wherein said substantially concentric axial hole in each of said cannulated screw member, said shaft member, and said handle member is configured to receive a Kirschner wire in at least a close clearance fit.

* * * * *